(12) United States Patent
Iguchi et al.

(10) Patent No.: US 9,580,432 B2
(45) Date of Patent: Feb. 28, 2017

(54) FUSED PYRIMIDINE COMPOUND OR SALT THEREOF

(71) Applicant: TAIHO PHARMACEUTICAL CO., LTD., Chiyoda-ku (JP)

(72) Inventors: Satoru Iguchi, Tsukuba (JP); Fumihito Hosoi, Tsukuba (JP); Takeshi Sagara, Tsukuba (JP)

(73) Assignee: TAIHO PHARMACEUTICAL CO., LTD., Chiyoda-ku (JP)

( * ) Notice: Subject to any disclaimer, the term of this patent is extended or adjusted under 35 U.S.C. 154(b) by 0 days.

(21) Appl. No.: 14/784,239

(22) PCT Filed: Aug. 11, 2014

(86) PCT No.: PCT/JP2014/071158
§ 371 (c)(1),
(2) Date: Oct. 13, 2015

(87) PCT Pub. No.: WO2015/022926
PCT Pub. Date: Feb. 19, 2015

(65) Prior Publication Data
US 2016/0115168 A1    Apr. 28, 2016

(30) Foreign Application Priority Data

Aug. 12, 2013 (JP) ................. 2013-167600

(51) Int. Cl.
| | | |
|---|---|---|
| A01N 43/90 | (2006.01) | |
| A61K 31/519 | (2006.01) | |
| C07D 487/00 | (2006.01) | |
| C07D 487/04 | (2006.01) | |
| C07D 519/00 | (2006.01) | |
| C07F 5/02 | (2006.01) | |

(52) U.S. Cl.
CPC .......... *C07D 487/04* (2013.01); *A61K 31/519* (2013.01); *C07D 519/00* (2013.01); *C07F 5/02* (2013.01)

(58) Field of Classification Search
None
See application file for complete search history.

(56) References Cited

U.S. PATENT DOCUMENTS

| | | |
|---|---|---|
| 2007/0135387 A1 | 6/2007 | Michaelides et al. |
| 2008/0214501 A1 | 9/2008 | Pan et al. |
| 2013/0018032 A1 | 1/2013 | Chen et al. |
| 2013/0225812 A1 | 8/2013 | Pan et al. |
| 2014/0343035 A1 | 11/2014 | Sagara et al. |

FOREIGN PATENT DOCUMENTS

| | | |
|---|---|---|
| JP | 2009-518434 A | 5/2009 |
| WO | 20091057733 A1 | 5/2009 |
| WO | 2009/158571 A1 | 12/2009 |
| WO | 2011/090760 A1 | 7/2011 |
| WO | 2011/090760 A4 | 7/2011 |
| WO | 2013/010136 A2 | 1/2013 |
| WO | 2013/108809 A1 | 7/2013 |

OTHER PUBLICATIONS

Edward M Schaeffer, et al., "Tec family kinases in lymphocyte signaling and function", Curr Op Imm, Total 7 Pages, (2000).
Lee A. Honigberg, et al., "The Bruton tyrosine kinase inhibitor PCI-32765 blocks B-cell activation and is efficacious in models of autoimmune disease and B-cell malignancy", PNAS, vol. 107, No. 29, pp. 13075-13080, (Jul. 20, 2010).
Mario E. Lacouture, "Mechanisms of cutaneous toxicities to EGFR inhibitors", Nature Reviews Cancer, vol. 6, pp. 803-812, (Oct. 2006).
Dorothy M. K. Keefe, et al., "Tumor control versus adverse events with targeted anticancer therapies", Nature Reviews Clinical Oncology, vol. 9, pp. 98-109, (Feb. 2012).
Betty Y. Chang, et al., "PCI-45292, a Novel Btk Inhibitor with Optimized Pharmaceutical Properties, Demonstrates Potent Activities in Rodent Models of Arthritis", Pharmacyclics, American College of Rheumatology Annual Meeting, Total 1 Page, (Nov. 6-11, 2010).
International Search Report and Written Opinion of the International Searching Authority Issued Nov. 4, 2014 in PCT/JP14/071158 Filed Aug. 11, 2014.

*Primary Examiner* — Jeffrey H Murray
(74) *Attorney, Agent, or Firm* — Oblon, McClelland, Maier & Neustadt, L.L.P.

(57) ABSTRACT

Provided is a novel compound having BTK inhibitory action and a cell proliferation suppressing effect. Also provided is a medicine useful for the prevention and/or treatment of a disease associated with BTK, particularly cancer, based on BTK inhibitory action. A compound represented by formula (I) [wherein $R_1$ to $R_3$, W, A, Y and Z respectively have the meanings as defined in the specification], or a salt thereof is disclosed.

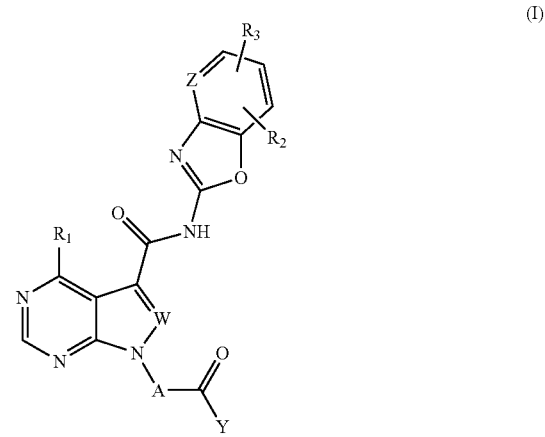

24 Claims, 1 Drawing Sheet

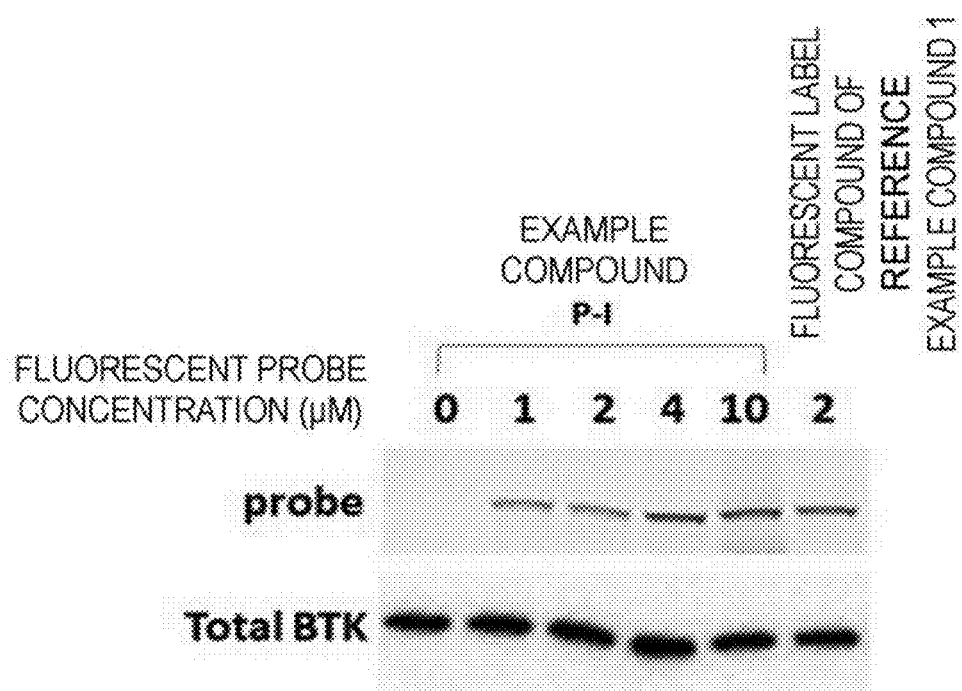

FUSED PYRIMIDINE COMPOUND OR SALT THEREOF

TECHNICAL FIELD

The present invention relates to a novel fused pyrimidine compound or a salt thereof, which has Bruton's tyrosine kinase (BTK) inhibitory action, and a pharmaceutical composition containing the same.

BACKGROUND ART

It is known that various protein kinases exist in in vivo and are involved in the regulation of a variety of functions. Bruton's tyrosine kinase (BTK) is a protein kinase that belongs to the Tec family kinases, and is a non-receptor tyrosine kinase that plays an important role related to the control of, for example, proliferation, survival, differentiation and activation of B-cells in the downstream of the B cell receptor (BCR) signal (Non-Patent Document 1). An inhibitor capable of controlling the activity of BTK is considered to be useful as a therapeutic agent for diseases associated with abnormal hyperactivity of BTK signaling pathway (for example, cancer).

Regarding a compound having BTK inhibitory activity, PCI-32765 (Non-Patent Document 2) and the compounds described in Patent Documents 1 and 2 are known.

The compounds disclosed in Patent Documents 1 and 2 are also known to exhibit high inhibitory activity for EGFR (Epidermal Growth Factor Receptor) and JAK3 (Janus kinase 3) for example, in addition to BTK. However, since such a multikinase inhibitor suppresses, for example, cell proliferation by inhibiting various signaling pathways, there is a concern about a variety of side effects. For example, it is known that EGFR binds to its ligand, for example, the epidermal growth factor (EGF), and participates in the proliferation and survival (for example, inhibition of apoptosis) of various cells (Non-Patent Document 3). However, it is known that inhibitors targeting EGFR cause side effects such as skin disorders and gastrointestinal dysfunction in common, and it is widely supposed that these side effects may be related to the inhibition of the wild type EGFR signaling pathway (Non-Patent Document 4).

Thus, PCI-45292 is known as a compound, which has an inhibitory activity against BTK with a weak inhibitory activity against EGFR (Non-Patent Document 5).

As described above, from the viewpoint of reducing side effects, a highly selective BTK inhibitor, that has a high inhibitory activity against BTK with low inhibitory activities against other kinases such as EGFR, is desired.

CITATION LIST

Patent Document

Patent Document 1: WO 2011/090760
Patent Document 2: WO 2009/158571

Non-Patent Document

Non-Patent Document 1: Schaeffer and Schwartzberg, Curr. Op. Imm., 2000, 282-288
Non-Patent Document 2: Proc. Natl. Acad. Sci. USA., 2010 Jul. 20; 107(29):13075-80
Non-Patent Document 3: Nature Rev. Cancer, Vol. 6, pp. 803-811 (2006)
Non-Patent Document 4: Nature Rev. Clin. Oncol., Vol. 6, pp. 98-109 (2012)
Non-Patent Document 5: American College of Rheumatology Annual Meeting, Atlanta, Ga., 6-11 Nov. 2010)

SUMMARY OF INVENTION

Technical Problem

An object of the present invention is to provide a novel compound that strongly inhibits BTK selectively over EGFR, or a salt thereof, and a pharmaceutical composition including this compound.

Solution to Problem

The inventors of the present invention conducted extensive investigations in order to achieve the problems described above, and as a result, the inventors found that a group of compounds represented by the following formula (I) exhibit an excellent inhibitory activity against BTK and excellent kinase selectivity, and are useful as medicines for treating diseases involving BTK, such as cancer. Thus, the inventors completed the present invention.

That is, the present invention is to provide a compound represented by the following general formula (I), or a salt thereof:

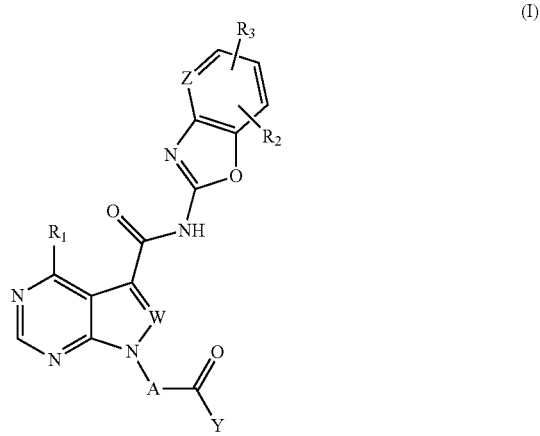

wherein A represents $-(CH_2)_n-X-$, $-(CH_2)_m-NH-$, or $-(C3-C7 \text{ cycloalkylene})-NH-$;

n represents an integer from 0 to 2;

m represents an integer from 1 to 4;

X represents a nitrogen-containing C3-C10 heterocycloalkylene which may have one or more substituents;

Y represents $-C(R_4)=C(R_5)(R_6)$ or $-C\equiv C-R_7$;

W and Z each independently represent N or CH;

$R_1$ represents an amino group which may have one or more substituents;

$R_2$ and $R_3$, which may be identical or different, each represent a hydrogen atom, a halogen atom, a C1-C6 alkyl group which may have one or more substituents, a C1-C6 alkoxy group which may have one or more substituents, a C3-C7 cycloalkyl group which may have one or more substituents, a C6-C14 aromatic hydrocarbon group which may have one or more substituents, a 4-membered to 10-membered monocyclic or polycyclic unsaturated heterocyclic group containing 1 to 3 heteroatoms of the same kind or different kinds selected from a nitrogen atom, an oxygen atom and a sulfur atom, which may have one or more substituents, or a cyano group; and $R_4$, $R_5$, $R_6$ and $R_7$, which may be identical or different, each represent a hydrogen atom, or a C1-C6 alkyl group which may have one or more substituents.

Furthermore, the present invention is to provide a probe compound containing a compound represented by the above general formula (I) or a salt thereof, a detectable label or affinity tag, and a linker, in which the linker links the compound to the label or the tag.

Furthermore, the present invention is to provide a BTK inhibitor containing a compound represented by the above general formula (I) or a salt thereof as an active ingredient.

Also, the present invention is to provide a pharmaceutical composition containing a compound represented by the above general formula (I) or a salt thereof.

Furthermore, the present invention is to provide an anti-tumor agent containing a compound represented by the above general formula (I) or a salt thereof as an active ingredient.

Furthermore, the present invention is to provide a compound represented by the above general formula (I) or a salt thereof, intended for tumor therapy.

Also, the present invention is to provide use of a compound represented by the above formula (I) or a salt thereof, for the production of an anti-tumor agent.

Furthermore, the present invention is to provide a method for treating a tumor, the method including administering a compound represented by the above general formula (I) or a salt thereof.

As a compound related to the present invention, PCI-32765 that is in a clinical stage is known as a BTK inhibitor. PCI-32765 has a phenoxyphenyl group; however, this compound is significantly different from the compound of the present invention in view of not having a benzoxazole group or an oxazolopyridine group, which represents a feature of the compound of the present invention. Furthermore, the compound of the present invention is characterized by having higher BTK selectivity compared to PCI-32765 (reference compound 1), as described later.

Furthermore, the compounds described in Patent Documents 1 and 2 also do not have a benzoxazole group or an oxazolopyridine group, which is a feature of the compound of the present invention, and their structures are significantly different.

Furthermore, the compound disclosed in WO 2007/067781 is known as a compound having the structure related to the compound of the present invention. However, the compound disclosed therein is a compound which inhibits aurora kinases, and there is no description on the presence or absence of the BTK inhibitory activity. Also, there is no disclosure on specific compounds having a benzoxazole group or an oxazolopyridine group.

Advantageous Effects of Invention

According to the present invention, there is provided a novel compound represented by the above formula (I) or a salt thereof, which is useful as a BTK inhibitor.

It has been made clear that the compound of the present invention or a salt thereof has excellent selective BTK inhibitory activity and exhibits a proliferation suppressing effect on cancer cell lines. Furthermore, since the compound of the present invention or a salt thereof strongly inhibits BTK selectively over EGFR, adverse side effects can be reduced, and enhancement of safety can be expected.

The compound of the present invention or a salt thereof has an advantage that the compound or salt not only exhibits excellent metabolic stability compared with conventional BTK inhibitors, but good exposure to plasma can be expected, and in addition Cyp inhibitory risk can be avoided.

The compound of the present invention or a salt thereof is useful as a prophylactic and/or therapeutic agent for cancer.

The compound of the present invention or a salt thereof can suppress bone metastasis of cancer or tumors.

BRIEF DESCRIPTION OF DRAWING

FIG. 1 shows the results of detection by BTK labeling using a fluorescent label compound.

DESCRIPTION OF EMBODIMENT

The compound represented of the above-described formula (I) of the present invention is a compound having a 1H-pyrazolo[3,4-d]pyrimidine skeleton or a 7H-pyrrolo[2,3-d]pyrimidine skeleton, which is substituted with a benzoxazole group or an oxazolopyridine group as one or more substituents linked via an amide bond, and the compound is a novel compound that has never been described in any of the prior art citations mentioned above.

According to the present specification, examples of the "substituent(s)" include a halogen atom, a hydroxyl group, a cyano group, a nitro group, an alkyl group, a halogenoalkyl group, a cycloalkyl group, a cycloalkyl-alkyl group, an aralkyl group, an alkenyl group, an alkynyl group, an alkoxy group, a halogenoalkoxy group, a cycloalkoxy group, a cycloalkyl-alkoxy group, an aralkyloxy group, an alkylthio group, a cycloalkyl-alkylthio group, an amino group, a mono- or dialkylamio group, a cycloalkyl-alkylamino group, an acyl group, an acyloxy group, an oxo group, a carboxyl group, an alkoxycarbonyl group, an aralkyloxycarbonyl group, a carbamoyl group, a saturated or unsaturated heterocyclic group, an aromatic hydrocarbon group, and a saturated heterocyclic oxy group. When the above-mentioned substituents are present, the number of the substituents is typically 1, 2 or 3.

Examples of the "halogen atom" according to the present specification include a fluorine atom, a chlorine atom, a bromine atom, and an iodine atom.

The "alkyl group" according to the present specification may be any of a linear group or a branched group, and examples thereof include C1-C6 alkyl groups such as a methyl group, an ethyl group, an n-propyl group, an isopropyl group, an n-butyl group, an isobutyl group, a tert-butyl group, an n-pentyl group, an isopentyl group, and a hexyl group.

The "halogenoalkyl group" according to the present specification is a linear or branched alkyl group having 1 to 6 carbon atoms and 1 to 13 halogen atoms (halogeno-C1-C6 alkyl group), and examples thereof include halogeno-C1-C6 alkyl groups such as a fluoromethyl group, a difluoromethyl group, a trifluoromethyl group, a trichloromethyl group, a fluoroethyl group, a 1,1,1-trifluoroethyl group, a monofluoro-n-propyl group, a perfluoro-n-propyl group, and a perfluoroisopropyl group, while preferred examples include halogeno-C1-C4 alkyl groups.

Specific examples of the "cycloalkyl group" according to the present specification include C3-C7 cycloalkyl groups such as cyclopropyl, cyclobutyl, cyclopentyl, cyclohexyl, and cycloheptyl. The "cycloalkylene" according to the present specification represents a divalent cycloalkyl.

Examples of the "cycloalkyl-alkyl group" according to the present specification include C3-C7 cyloalkyl-substituted C1-C4 alkyl groups such as a cyclopropylmethyl group, a cyclobutylmethyl group, a cyclopentylmethyl group, a cyclohexylmethyl group, and a cycloheptylmethyl group.

Examples of the "aralkyl group" according to the present specification include C7-C13 aralkyl groups such as a benzyl group, a phenethyl group, a naphthylmethyl group, and a fluorenylmethyl group.

The "alkenyl group" according to the present specification means an unsaturated hydrocarbon group which may be any of a linear group, a branched group or a cyclic group, and has at least one double bond. Examples thereof include C2-C6 alkenyl groups such as a vinyl group, an allyl group, a 1-propenyl group, a 2-methyl-2-propenyl group, an isopropenyl group, a 1-, 2- or 3-butenyl group, a 2-, 3- or 4-pentenyl group, a 2-methyl-2-butenyl group, a 3-methyl-2-butenyl group, a 5-hexenyl group, a 1-cyclopentenyl group, a 1-cyclohexenyl group, and a 3-methyl-3-butenyl group.

The "alkynyl group" according to the present specification means an unsaturated hydrocarbon group which may be any of a linear group, a branched group or a cyclic group, and has at least one triple bond. Examples thereof include C2-C6 alkynyl groups such as an ethynyl group, a 1- or 2-propynyl group, a 1-, 2- or 3-butynyl group, and a 1-methyl-2-propynyl group.

The "alkoxy group" according to the present specification may be any of a linear group or a branched group, and examples thereof include C1-C6 alkoxy groups such as a methoxy group, an ethoxy group, a propoxy group, an isopropoxy group, a butoxy group, an isobutoxy group, a tert-butoxy group, a pentyloxy group, an isopentyloxy group, and a hexyloxy group.

The "halogenoalkoxy group" according to the present specification is a linear or branched alkoxy group having 1 to 6 carbon atoms and 1 to 13 halogen atoms (halogeno-C1-C6 alkoxy group), and examples thereof include halogeno-C1-C6 alkoxy groups such as a fluoromethoxy group, a difluoromethoxy group, a trifluoromethoxy group, a trichloromethoxy group, a fluoroethoxy group, a 1,1,1-trifluoroethoxy group, a monofluoro-n-propoxy group, a perfluoro-n-propoxy group, and a perfluoro-isopropoxy group, while preferred examples include halogeno-C1-C4 alkoxy groups.

Specific examples of the "cycloalkoxy group" according to the present specification include C3-C7 cycloalkoxy groups such as a cyclopropoxy group, a cyclobutoxy group, a cyclopentyloxy group, a cyclohexyloxy group, and a cycloheptyloxy group.

Examples of the "cycloalkyl-alkoxy group" according to the present specification include C3-C7 cycloalkyl-substituted C1-C4 alkoxy groups such as a cyclopropylmethoxy group, a cyclobutylmethoxy group, a cyclopentylmethoxy group, a cyclohexylmethoxy group, and a cycloheptylmethoxy group.

Examples of the "aralkyloxy group" according to the present specification include C7-C13 aralkyloxy groups such as a benzyloxy group, a phenethyloxy group, a naphthylmethyloxy group, and a fluorenylmethyloxy group.

The "alkylthio group" according to the present specification may be any of a linear group or a branched group, and examples thereof include C1-C6 alkylthio groups such as a methylthio group, an ethylthio group, an n-propylthio group, an isopropylthio group, an n-butylthio group, an isobutylthio group, a tert-butylthio group, an n-pentylthio group, an isopentylthio group, and a hexylthio group.

Examples of the "cycloalkyl-alkylthio group" according to the present specification include C3-C7 cycloalkyl-substituted C1-C4 alkylthio groups such as a cyclopropylmethylthio group, a cyclobutylmethylthio group, a cyclopentylmethylthio group, a cyclohexylmethylthio group, and a cycloheptylmethylthio group.

Examples of the "monoalkylamino group" according to the present specification include amino groups that are monosubstituted with linear or branched C1-C6 alkyl groups, such as a methylamino group, an ethylamino group, an n-propylamino group, an isopropylamino group, an n-butylamino group, an isobutylamino group, a tert-butylamino group, an n-pentylamino group, an isopentylamino group, and a hexylamino group.

Examples of the "dialkylamino group" according to the present specification include amino groups that are disubstituted with linear or branched C1-C6 alkyl groups, such as a dimethylamino group, a diethylamino group, a di(n-propyl)amino group, a diisopropylamino group, a di(n-butyl)amino group, an isobutylamino group, a di(tert-butyl)amino group, a di(n-pentyl)amino group, a diisopentylamino group, and a dihexylamino group.

Examples of the "cycloalkyl-alkylamino group" according to the present specification include C3-C7 cycloalkyl-substituted C1-C4 alkylamino groups such as a cyclopropylmethylamino group, a cyclobutylmethylamino group, a cyclopentylmethylamino group, a cyclohexylmethylamino group, and a cycloheptylmethylamino group.

The "acyl group" according to the present specification means an alkylcarbonyl group or an arylcarbonyl group.

Examples of the "alkylcarbonyl group" according to the present specification include linear or branched (C1-C6 alkyl)carbonyl groups such as methylcarbonyl, ethylcarbonyl, n-propylcarbonyl, isopropylcarbonyl, n-butylcarbonyl, isobutylcarbonyl, tert-butylcarbonyl, n-pentylcarbonyl, isopentylcarbonyl, and hexylcarbonyl.

Examples of the "arylcarbonyl group" according to the present specification include (C6-C14 aryl)carbonyl groups such as phenylcarbonyl, naphthylcarbonyl, fluorenylcarbonyl, anthrylcarbonyl, biphenylcarbonyl, tetrahydronaphthylcarbonyl, chromanylcarbonyl, 2,3-dihydro-1,4-dioxanaphthalenylcarbonyl, indanylcarbonyl, and phenanthrylcarbonyl.

The "acyloxy group" according to the present specification means an alkylcarbonyloxy group or an arylcarbonyloxy group.

Examples of the "alkylcarbonyloxy group" according to the present specification include linear or branched (C1-C6 alkyl)carbonyloxy groups such as methylcarbonyloxy, ethylcarbonyloxy, n-propylcarbonyloxy, isopropylcarbonyloxy, n-butylcarbonyloxy, isobutylcarbonyloxy, tert-butylcarbonyloxy, n-pentylcarbonyloxy, isopentylcarbonyloxy, and hexylcarbonyloxy.

Examples of the "arylcarbonyloxy group" according to the present specification include (C6-C14 aryl)carbonyloxy groups such as phenylcarbonyloxy, naphthylcarbonyloxy, fluorenylcarbonyloxy, anthrylcarbonyloxy, biphenylcarbonyloxy, tetrahydronaphthylcarbonyloxy, chromanylcarbonyloxy, 2,3-dihydro-1,4-dioxanaphthalenylcarbonyloxy, indanylcarbonyloxy, and phenanthrylcarbonyloxy.

The "alkoxycarbonyl group" according to the present specification may be any of a linear group or a branched group, and examples thereof include (C1-C6 alkoxy)carbonyl groups such as a methoxycarbonyl group, an ethoxycarbonyl group, a propoxycarbonyl group, an isopropoxycarbonyl group, a butoxycarbonyl group, an isobutoxycarbonyl group, a tert-butoxycarbonyl group, a pentyloxycarbonyl group, an isopentyloxycarbonyl group, and a hexyloxycarbonyl group.

Examples of the "aralkyloxycarbonyl group" according to the present specification include (C7-C13 aralkyl)oxycarbonyl groups such as a benzyloxycarbonyl group, a phenethyloxycarbonyl group, a naphthylmethyloxycarbonyl group, and a fluorenylmethyloxycarbonyl group.

The "saturated heterocyclic group" according to the present specification may be a saturated heterocyclic group having heteroatoms selected from a nitrogen atom, an oxygen atom and a sulfur atom, and specific examples thereof include a morpholino group, a 1-pyrrolidinyl group, a piperidino group, a piperazinyl group, a 4-methyl-1-piperazinyl group, a tetrahydrofuranyl group, a tetrahydropyranyl group, a tetrahydrothiophenyl group, and a thiazolidinyl group, and an oxazolidinyl group.

The "unsaturated heterocyclic group" according to the present specification is a monocyclic or polycyclic, fully unsaturated or partially unsaturated heterocyclic group having heteroatoms selected from a nitrogen atom, an oxygen atom and a sulfur atom, and specific examples thereof include an imidazolyl group, a thienyl group, a furyl group, a pyrrolyl group, an oxazolyl group, an isoxazolyl group, a triazolyl group, an isothiazolyl group, a thiadiazolyl group, a pyrazolyl group, a triazolyl group, a tetrazolyl group, a pyridyl group, a pyrazyl group, a pyrimidinyl group, a pyridazinyl group, an indolyl group, an isoindolyl group, an indazolyl group, a triazolopyridyl group, a benzimidazolyl group, a benzoxazolyl group, a benzothiazolyl group, a benzothienyl group, a benzofuranyl group, a purinyl group, a quinolyl group, an isoquinolyl group, a quinazolinyl group, a quinoxalyl group, a methylenedioxyphenyl group, an ethylenedioxyphenyl group, and a dihydrobenzofuranyl group.

Examples of the "aromatic hydrocarbon group" according to the present specification include C6-C14 aromatic hydrocarbon groups such as a phenyl group, a toluyl group, a xylyl group, a naphthyl group, an anthracenyl group, a phenanthryl group, a fluorenyl group, and a tetrahydronaphthyl group.

The "saturated heterocyclic oxy group" according to the present specification is a saturated heterocyclic oxy group having heteroatoms selected from a nitrogen atom, an oxygen atom and a sulfur atom, and specific examples thereof include a morpholinyloxy group, a 1-pyrrolidinyloxy group, a piperidinoxy group, a piperazinyloxy group, a 4-methyl-1-piperazinyloxy group, a tetrahydrofuranyloxy group, a tetrahydropyranyloxy group, a tetrahydrothiophenyloxy group, a thiazolidinyloxy group, and an oxazolidinyloxy group.

Meanwhile, the expression "CA-CB" in the description on one or more substituents in the present specification indicates that the substituent is one or more substituents whose carbon number is A to B. For example, "C1-C6 alkyl group" indicates an alkyl group having 1 to 6 carbon atoms, and "C6-C14 aromatic hydrocarbon oxy group" indicates an oxy group to which an aromatic hydrocarbon group having 6 to 14 carbon atoms is bonded. Also, the expression "A-membered to B-membered" indicates that the number of atoms that constitute a ring (number of ring members) is A to B. For example, "4-membered to 10-membered saturated heterocyclic group" means a saturated heterocyclic group whose number of ring members is 4 to 10.

In general formula (I), A represents —$(CH_2)_n$—X—, —$(CH_2)_m$—NH—, or —(C3-C7 cycloalkylene)-NH—.

n represents an integer from 0 to 2, but n is more preferably 0. Furthermore, m represents an integer from 1 to 4, but m is more preferably 2 or 3, and even more preferably 2. Examples of the C3-C7 cycloalkylene include cyclopropylene, cyclobutylene, cyclopentylene, and cyclohexylene, while cyclohexylene is more preferred.

X represents a nitrogen-containing C3-C10 heterocycloalkylene which may have one or more substituents; however, more specifically, X represents a divalent heterocycloalkyl having 3 to 10 carbon atoms, which may have one or more substituents, contains at least one nitrogen atom in the ring, and contains 0 to 2 heteroatoms of the same kind or different kinds selected from an oxygen atom and a sulfur atom (nitrogen-containing C3-C10 heterocycloalkylene). More specific examples thereof include azetidinylene, pyrrolidinylene, piperidinylene, piperazinylene, morpholinylene, octahydroquinolinylene, and octahydroindolylene.

Preferably, X represents a heterocycloalkylene having 3 to 5 carbon atoms, which may have one or more substituents and contains one nitrogen atom in the ring (nitrogen-containing C3-C5 heterocycloalkylene), and X is more preferably azetidinylene, pyrrolidinylene, or piperidinylene, and even more preferably 1,3-azetidinylene, 1,3-pyrrolidinylene, or 1,3-piperidinylene.

Regarding the substituents on these heterocycloalkylenes, examples include substituents such as those described above; however, it is preferable that the heterocycloalkylenes are unsubstituted.

It is preferable that the nitrogen atom of a nitrogen-containing C3-C10 heterocycloalkylene group represented by X is bonded to the carbonyl group of —COY in general formula (I). Furthermore, it is preferable that the nitrogen atom of a nitrogen-containing C3-C5 heterocycloalkylene group represented by X is bonded to the carbonyl group of —COY in general formula (I).

A is more preferably —$(CH_2)_n$—X—.

In general formula (I), Y represents —$C(R_4)$=$C(R_5)(R_6)$ or —C≡C—$R_7$.

In general formula (I), W and Z each independently represent N or CH. Preferably, when Z is N, W is N, or when Z is CH, W is N or CH.

In general formula (I), regarding the "substituent(s)" for the "amino group which may have one or more substituents" represented by $R_1$, examples include substituents such as those described above; however, it is preferable that the amino group is unsubstituted.

The "amino group which may have one or more substituents" represented by $R_1$ is preferably an amino group.

In general formula (I), the "halogen atom" represented by $R_2$ or $R_3$ is preferably a fluorine atom, a chlorine atom, or a bromine atom.

In general formula (I), the "C1-C6 alkyl group" for the "C1-C6 alkyl group which may have one or more substituents" represented by $R_2$ or $R_3$ is preferably a C1-C4 alkyl group, and the C1-C6 alkyl group is more preferably a methyl group, an ethyl group, an n-propyl group, an isopropyl group, an n-butyl group, an isobutyl group, or a tert-butyl group, and even more preferably a methyl group or an ethyl group.

Regarding the "substituent(s)" for the "C1-C6 alkyl group which may have one or more substituents" represented by $R_2$ or $R_3$, it is preferable that the C1-C6 alkyl group is unsubstituted, or has one or more substituents such as a halogen atom or a C1-C4 alkoxy group. It is more preferable that the C1-C6 alkyl group is unsubstituted, or has one or more substituents such as a fluorine atom or a methoxy group. In a case in which the alkyl group has one or more substituents the number of substituents is not particularly limited; however, when the substituent is a halogen atom, the number of substituents is preferably 1 to 3, while when the one or more substituents is a C1-C4 alkoxy group, the number of substituents is preferably 1.

The "C1-C6 alkyl group which may have one or more substituents" represented by $R_2$ or $R_3$ is preferably a C1-C6 alkyl group, a halogeno-C1-C6 alkyl group, or a C1-C4 alkoxy-substituted C1-C6 alkyl group; more preferably a C1-C4 alkyl group, a halogeno-C1-C4 alkyl group, or a C1-C4 alkoxy-substituted C1-C4 alkyl group; even more preferably a methyl group, an ethyl group, an n-propyl group, an isopropyl group, an n-butyl group, an isobutyl group, a tert-butyl group, a trifluoromethyl group, a trichloromethyl group, a methoxyethyl group, or an ethoxyethyl group; and still more preferably a methyl group, a trifluoromethyl group, or a methoxyethyl group.

In general formula (I), the "C1-C6 alkoxy group" for the "C1-C6 alkoxy group which may have one or more substituents" represented by $R_2$ or $R_3$ is preferably a "C1-C4 alkoxy group", and the "C1-C6 alkoxy group" is more preferably a methoxy group, an ethoxy group, an isopropoxy group, or an n-butoxy group, and even more preferably a methoxy group.

Regarding the "substituent(s)" for the "C1-C6 alkoxy group which may have one or more substituents" represented by $R_2$ or $R_3$, examples include substituents such as those described above; however, it is preferable that the C1-C6 alkoxy group is unsubstituted.

The "C1-C6 alkoxy group which may have one or more substituents" represented by $R_2$ or $R_3$ is preferably a C1-C6 alkoxy group; more preferably a C1 to C4 alkoxy group; even more preferably a methoxy group, an ethoxy group, an isopropoxy group, or an n-butoxy group; and still more preferably a methoxy group.

In general formula (I), The "C3-C7 cycloalkyl group" for the "C3-C7 cycloalkyl group which may have one or more substituents" represented by $R_2$ or $R_3$ is preferably a C3-C6 cycloalkyl group, and more preferably a cyclopropyl group, a cyclobutyl group, a cyclopentyl group, or a cyclohexyl group.

Regarding the "substituent(s)" for the "C3-C7 cycloalkyl group which may have one or more substituents" represented by $R_2$ or $R_3$, examples include substituents such as those described above; however, it is preferable that the C3-C7 cycloalkyl group is unsubstituted.

The "C3-C7 cycloalkyl group which may have one or more substituents" represented by $R_2$ or $R_3$ is preferably a C3-C6 cycloalkyl group, and more preferably a cyclopropyl group, a cyclobutyl group, a cyclopentyl group, or a cyclohexyl group.

In general formula (I), the "C6-C14 aromatic hydrocarbon group" for the "C6-C14 aromatic hydrocarbon group which may have one or more substituents" represented by $R_2$ or $R_3$ is preferably a phenyl group or a naphthyl group, and more preferably a phenyl group.

Regarding the "substituent(s)" for the "C6-C14 aromatic hydrocarbon group which may have one or more substituents" represented by $R_2$ or $R_3$, it is preferable that the C6-C14 aromatic hydrocarbon group is unsubstituted, or has a halogen atom. It is more preferable that the C6-C14 aromatic hydrocarbon group is unsubstituted, or has a chlorine atom or a fluorine atom. When the C6-C14 aromatic hydrocarbon group has one or more substituents, the number of substituents is not particularly limited; however, the number of substituents is preferably 1 to 3.

The "C6-C14 aromatic hydrocarbon group which may have one or more substituents" represented by $R_2$ or $R_3$ is preferably a phenyl group or a naphthyl group, which is unsubstituted or may have one or more substituents with a halogen atom, and is more preferably a phenyl group, a chlorophenyl group, a fluorophenyl group, a dichlorophenyl group, or a trichlorophenyl group; even more preferably a phenyl group or a chlorophenyl group; and particularly preferably a phenyl group or a 4-chlorophenyl group.

In general formula (I), the "4-membered to 10-membered monocyclic or polycyclic unsaturated heterocyclic group containing 1 to 3 heteroatoms of the same kind or different kinds selected from a nitrogen atom, an oxygen atom and a sulfur atom" for the "4-membered to 10-membered monocyclic or polycyclic unsaturated heterocyclic group containing 1 to 3 heteroatoms of the same kind or different kinds selected from a nitrogen atom, an oxygen atom and a sulfur atom, which may have one or more substituents" represented by $R_2$ or $R_3$ is preferably a 4-membered to 6-membered monocyclic unsaturated heterocyclic group containing one nitrogen atom, oxygen atom or sulfur atom; more preferably a 4-membered to 6-membered monocyclic unsaturated heterocyclic group containing one sulfur atom; even more preferably a thienyl group; and still more preferably a 2-thienyl group.

Regarding the "substituent(s)" for the "4-membered to 10-membered monocyclic or polycyclic unsaturated heterocyclic group containing 1 to 3 heteroatoms of the same kind or different kinds selected from a nitrogen atom, an oxygen atom and a sulfur atom, which may have one or more substituents" represented by $R_2$ or $R_3$, examples include substituents such as those described above; however, it is preferable that the unsaturated heterocyclic group is unsubstituted.

The "4-membered to 10-membered monocyclic or polycyclic unsaturated heterocyclic group containing 1 to 3 heteroatoms of the same kind or different kinds selected from a nitrogen atom, an oxygen atom and a sulfur atom, which may have one or more substituents" represented by $R_2$ or $R_3$ is preferably a 4-membered to 6-membered monocyclic unsaturated heterocyclic group containing one of a nitrogen atom, an oxygen atom or a sulfur atom; more preferably a 4-membered to 6-membered monocyclic unsaturated heterocyclic group containing one sulfur atom; even more preferably a thienyl group; and still more preferably a 2-thienyl group.

In general formula (I), the "C1-C6 alkyl group" for the "C1-C6 alkyl group which may have one or more substituents" represented by $R_4$, $R_5$ or $R_6$ is preferably a C1-C4 alkyl group; more preferably a methyl group, an ethyl group, an n-propyl group, an isopropyl group, an n-butyl group, an isobutyl group, or a tert-butyl group; and even more preferably a methyl group.

Regarding the "substituent(s)" for the "C1-C6 alkyl group which may have one or more substituents" represented by $R_4$, $R_5$ or $R_6$, it is preferable that the C1-C6 alkyl group is unsubstituted, or has an amino group substituted with two C1-C4 alkyl groups (the C1-C4 alkyl groups may also form a heterocycloalkyl group having a 4-membered to 8-membered ring, together with the nitrogen atom to which these alkyl groups are bonded). It is more preferable that the C1-C6 alkyl group is unsubstituted, or has a dimethylamino group, a methylethylamino group, a diethylamino group, a methylisopropylamino group, a 1-piperidinyl group, or a 1-pyrrolidinyl group. When the "C1-C6 alkyl group which may have one or more substituents" has one or more substituents, the number of substituents is not particularly limited; however, the number of substituents is preferably 1.

The "C1-C6 alkyl group which may have one or more substituents" represented by $R_4$, $R_5$ or $R_6$ is preferably a C1-C4 alkyl group, or a C1-C4 alkyl group that is substituted with an amino group substituted with two C1-C4 alkyl groups (the C1-C4 alkyl groups may form a heterocycloalkyl group having a 4-membered to 8-membered ring, together with the nitrogen atom to which these alkyl groups are bonded). More preferred examples thereof include a methyl group, an ethyl group, an n-propyl group, an isopropyl group, an n-butyl group, a dimethylaminomethyl group, a methylethylaminomethyl group, a diethylaminomethyl group, a methylisopropylaminomethyl group, a dimethylaminoethyl group, a diethylaminoethyl group, a 1-piperidinylmethyl group, and a 1-pyrrolidinylmethyl group.

In general formula (I), the "C1-C6 alkyl group" for the "C1-C6 alkyl group which may have one or more substituents" represented by $R_7$ is preferably a C1-C4 alkyl group; more preferably a methyl group, an ethyl group, an n-propyl group, an isopropyl group, or an n-butyl group; and even more preferably a methyl group.

Regarding the "substituent(s)" for the "C1-C6 alkyl group which may have one or more substituents" represented by $R_7$, examples include substituents such as those described above; however, it is preferable that the C1-C6 alkyl group is unsubstituted.

The "C1-C6 alkyl group which may have one or more substituents" represented by $R_7$ is preferably a C1-C4 alkyl group; more preferably a methyl group, an ethyl group, an n-propyl group, an isopropyl group, or an n-butyl group; and even more preferably a methyl group.

In general formula (I), $—C(R_4)=C(R_5)(R_6)$ or $—C\equiv C—R_7$ represented by Y is particularly preferably any one selected from:

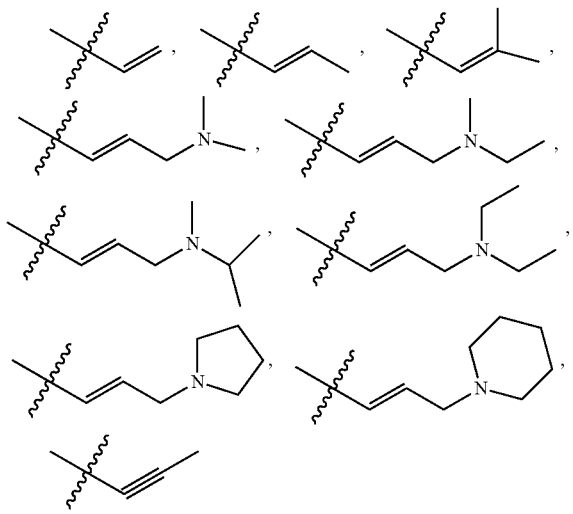

In regard to the compound of the present invention represented by general formula (I), preferred is a compound, or a salt thereof, in which:
A represents $—(CH_2)_n—X—$;
n represents 0;
X represents a nitrogen-containing C3-C10 heterocycloalkylene;
Y represents $—C(R_4)=C(R_5)(R_6)$ or $—C\equiv C—R_7$;
W and Z each independently represent N or CH;
$R_1$ represents an amino group;
$R_2$ and $R_3$, which may be identical or different, each represent a hydrogen atom, a halogen atom, a C1-C6 alkyl group which may have one or more substituents, a C1-C6 alkoxy group which may have one or more substituents, a C3-C7 cycloalkyl group which may have one or more substituents, a C6-C14 aromatic hydrocarbon group which may have one or more substituents, a 4-membered to 10-membered, monocyclic or polycyclic unsaturated heterocyclic group containing 1 to 3 heteroatoms of the same kind or different kinds selected from a nitrogen atom, an oxygen atom and a sulfur atom, which may have one or more substituents, or a cyano group; and
$R_4$, $R_5$, $R_6$ and $R_7$, which may be identical or different, each represent a hydrogen atom, or a C1-C6 alkyl group which may have one or more substituents.

In this case, in regard to the compound of the present invention represented by general formula (I), more preferred is a compound, or a salt thereof, in which:
A represents $—(CH_2)_n—X—$;
n represents 0;
X represents a nitrogen-containing C3-C10 heterocycloalkylene (here, the nitrogen atom is bonded to the carbonyl group of —COY in the general formula (I));
Y represents $—C(R_4)=C(R_5)(R_6)$ or $—C\equiv C—R_7$;
W and Z each independently represent N or CH;
$R_1$ represents an amino group;
$R_2$ and $R_3$, which may be identical or different, each represent a hydrogen atom, a halogen atom, a C1-C6 alkyl group which may have one or more substituents, a C1-C6 alkoxy group which may have one or more substituents, a C3-C7 cycloalkyl group which may have one or more substituents, a C6-C14 aromatic hydrocarbon group which may have one or more substituents, a 4-membered to 10-membered, monocyclic or polycyclic unsaturated heterocyclic group containing 1 to 3 heteroatoms of the same kind or different kinds selected from a nitrogen atom, an oxygen atom and a sulfur atom, which may have one or more substituents, or a cyano group; and
$R_4$, $R_5$, $R_6$ and $R_7$, which may be identical or different, each represent a hydrogen atom or a C1-C6 alkyl group which may have one or more substituents.

In regard to the compound of the present invention represented by general formula (I), more preferred is a compound, or a salt thereof, in which:
A represents $—(CH_2)_n—X—$;
n represents 0;
X represents azetidinylene, pyrrolidinylene, or piperidinylene;
Y represents $—C(R_4)=C(R_5)(R_6)$ or $—C\equiv C—R_7$;
W and Z each independently represent N or CH;
$R_1$ represents an amino group;
$R_2$ and $R_3$, which may be identical or different, each represent a hydrogen atom, a halogen atom, a C1-C6 alkyl group which may have one or more substituents, a C1-C6 alkoxy group which may have one or more substituents, a C3-C7 cycloalkyl group which may have one or more substituents, a C6-C14 aromatic hydrocarbon group which may have one or more substituents, a 4-membered to 10-membered, monocyclic or polycyclic unsaturated heterocyclic group containing 1 to 3 heteroatoms of the same kind or different kinds selected from a nitrogen atom, an oxygen atom and a sulfur atom, which may have one or more substituents, or a cyano group; and
$R_4$, $R_5$, $R_6$ and $R_7$, which may be identical or different, each represent a hydrogen atom or a C1-C6 alkyl group which may have one or more substituents.

In this case, in regard to the compound of the present invention represented by general formula (I), more preferred is a compound, or a salt thereof, in which:

A represents —(CH$_2$)$_n$—X—;

n represents 0;

X represents azetidinylene, pyrrolidinylene, or piperdinylene (here, the nitrogen atom is bonded to the carbonyl group of —COY in the general formula (I));

Y represents —C(R$_4$)=C(R$_5$)(R$_6$) or —C≡C—R$_7$;

W and Z each independently represent N or CH;

R$_1$ represents an amino group;

R$_2$ and R$_3$, which may be identical or different, each represent a hydrogen atom, a halogen atom, a C1-C6 alkyl group which may have one or more substituents, a C1-C6 alkoxy group which may have one or more substituents, a C3-C7 cycloalkyl group which may have one or more substituents, a C6-C14 aromatic hydrocarbon group which may have one or more substituents, a 4-membered to 10-membered monocyclic or polycyclic unsaturated heterocyclic group containing 1 to 3 heteroatoms of the same kind or different kinds selected from a nitrogen atom, an oxygen atom and a sulfur atom, which may have one or more substituents, or a cyano group; and R$_4$, R$_5$, R$_6$ and R$_7$, which may be identical or different, each represent a hydrogen atom or a C1-C6 alkyl group which may have one or more substituents.

In regard to the compound of the present invention represented by general formula (I), more preferred is a compound, or a salt thereof, in which:

A represents —(CH$_2$)$_n$—X—;

n represents 0;

X represents azetidinylene, pyrrolidinylene, or piperdinylene;

Y represents —C(R$_4$)=C(R$_5$)(R$_6$) or —C≡C—R$_7$;

W and Z each independently represent N or CH;

R$_1$ represents an amino group;

any one of R$_2$ and R$_3$ represents a hydrogen atom or a C1-C6 alkyl group, while the other represents a hydrogen atom, a halogen atom, a C1-C6 alkyl group, a halogeno-C1-C6 alkyl group, a C1-C4 alkoxy-substituted C1-C6 alkyl group, a C1-C6 alkoxy group, a phenyl group which may have one or more substituents with a halogen atom, a 4-membered to 6-membered monocyclic unsaturated heterocyclic group containing a sulfur atom, or a cyano group; and when Y represents —C(R$_4$)=C(R$_5$)(R$_6$), R$_4$, R$_5$ and R$_6$, which may be identical or different, each represent a hydrogen atom, a C1-C6 alkyl group, or a C1-C6 alkyl group that is substituted with an amino group substituted with two C1-C6 alkyl groups (the C1-C6 alkyl groups may form a heterocycloalkyl group having a 4-membered to 8-membered ring, together with the nitrogen atom to which these alkyl groups are bonded);

when Y represents —C≡C—R$_7$,

R$_7$ represents a hydrogen atom or a C1-C6 alkyl group.

In this case, in regard to the compound of the present invention represented by general formula (I), more preferred is a compound, or a salt thereof, in which:

A represents —(CH$_2$)$_n$—X—;

n represents 0;

X represents azetidinylene, pyrrolidinylene, or piperdinylene (here, the nitrogen atom is bonded to the carbonyl group of —COY in the general formula (I));

Y represents —C(R$_4$)=C(R$_5$)(R$_6$) or —C≡C—R$_7$;

W and Z each independently represent N or CH;

R$_1$ represents an amino group;

any one of R$_2$ and R$_3$ represents a hydrogen atom or a C1-C6 alkyl group, while the other represents a hydrogen atom, a halogen atom, a C1-C6 alkyl group, a halogeno-C1-C6 alkyl group, a C1-C4 alkoxy-substituted C1-C6 alkyl group, a C1-C6 alkoxy group, a phenyl group which may have one or more substituents with a halogen atom, a 4-membered to 6-membered monocyclic unsaturated heterocyclic group containing a sulfur atom, or a cyano group; and when Y represents —C(R$_4$)=C(R$_5$)(R$_6$), R$_4$, R$_5$ and R$_6$, which may be identical or different, each represent a hydrogen atom, a C1-C6 alkyl group, or a C1-C6 alkyl group that is substituted with an amino group substituted with two C1-C6 alkyl groups (the C1-C6 alkyl groups may form a heterocycloalkyl group having a 4-membered to 8-membered ring, together with the nitrogen atom to which these alkyl groups are bonded);

when Y represents —C≡C—R$_7$,

R$_7$ represents a hydrogen atom or a C1-C6 alkyl group.

In regard to the compound of the present invention represented by general formula (I), more preferred is a compound, or a salt thereof, in which:

A represents —(CH$_2$)$_n$—X—;

n represents 0;

X represents 1,3-azetidinylene, 1,3-pyrrolidinylene, or 1,3-piperdinylene;

Y represents —C(R$_4$)=C(R$_5$)(R$_6$) or —C≡C—R$_7$;

when Z represents N, W represents N, while when Z represents CH, W represents N or CH;

R$_1$ represents an amino group;

any one of R$_2$ and R$_3$ represents a hydrogen atom or a C1-C4 alkyl group, while the other represents a hydrogen atom, a halogen atom, a C1-C4 alkyl group, a halogeno-C1-C4 alkyl group, a C1-C4 alkoxy-substituted C1-C4 alkyl group, a C1-C4 alkoxy group, a phenyl group which may have one or more substituents with a halogen atom, a 4-membered to 6-membered monocyclic unsaturated heterocyclic group containing a sulfur atom, or a cyano group; and when Y represents —C(R$_4$)=C(R$_5$)(R$_6$), R$_4$, R$_5$ and R$_6$, which may be identical or different, each represent a hydrogen atom, a C1-C6 alkyl group, or a C1-C6 alkyl group that is substituted with an amino group substituted with two C1-C6 alkyl groups (the C1-C6 alkyl groups may form a heterocycloalkyl group having a 4-membered to 8-membered ring, together with the nitrogen atom to which these alkyl groups are bonded);

when Y represents —C≡C—R$_7$,

R$_7$ represents a hydrogen atom or a C1-C4 alkyl group.

In this case, in regard to the compound of the present invention represented by general formula (I), more preferred is a compound, or a salt thereof, in which:

A represents —(CH$_2$)$_n$—X—;

n represents 0;

X represents 1,3-azetidinylene, 1,3-pyrrolidinylene, or 1,3-piperdinylene (here, the nitrogen atom is bonded to the carbonyl group of —COY in the general formula (I));

Y represents —C(R$_4$)=C(R$_5$)(R$_6$) or —C≡C—R$_7$;

when Z represents N, W represents N, while when Z represents CH, W represents N or CH;

R$_1$ represents an amino group;

any one of R$_2$ and R$_3$ represents a hydrogen atom or a C1-C4 alkyl group, while the other represents a hydrogen atom, a halogen atom, a C1-C4 alkyl group, a halogeno- C1-C4 alkyl group, a C1-C4 alkoxy-substituted C1-C4 alkyl group, a C1-C4 alkoxy group, a phenyl group which may have one or more substituents with a halogen atom, a 4-membered to 6-membered monocyclic unsaturated heterocyclic group containing a sulfur atom, or a cyano group; and when Y represents —C($R_4$)=C($R_5$)($R_6$), $R_4$, $R_5$ and $R_6$, which may be identical or different, each represent a hydrogen atom, a C1-C6 alkyl group, or a C1-C6 alkyl group that is substituted with an amino group substituted with two C1-C6 alkyl groups (the C1-C6 alkyl groups may form a heterocycloalkyl group having a 4-membered to 8-membered ring, together with the nitrogen atom to which these alkyl groups are bonded);

when Y represents —C≡C—$R_7$, $R_7$ represents a hydrogen atom or a C1-C4 alkyl group.

In regard to the compound of the present invention represented by general formula (I), more preferred is a compound, or a salt thereof, in which:

A represents —(CH$_2$)$_n$—X—;

n represents 0;

X represents 1,3-azetidinylene, 1,3-pyrrolidinylene, or 1,3-piperdinylene;

Y represents —C($R_4$)=C($R_5$)($R_6$) or —C≡C—$R_7$;

when Z represents N, W represents N, while when Z represents CH, W represents N or CH;

$R_1$ represents an amino group;

any one of $R_2$ and $R_3$ represents a hydrogen atom or a methyl group, while the other represents a hydrogen atom, a halogen atom, a methyl group, a trifluoromethyl group, a methoxyethyl group, a methoxy group, a phenyl group, a 4-chlorophenyl group, a 2-thienyl group, or a cyano group; and when Y represents —C($R_4$)=C($R_5$)($R_6$), $R_4$, $R_5$ and $R_6$, which may be identical or different, each represent a hydrogen atom, a methyl group, a dimethylaminomethyl group, a methylethylaminomethyl group, a diethylaminomethyl group, a methylisopropylaminomethyl group, a 1-piperidinylmethyl group, or a 1-pyrrolidinylmethyl group;

when Y represents —C≡C—$R_7$, $R_7$ represents a methyl group.

In this case, in regard to the compound of the present invention represented by general formula (I), more preferred is a compound, or a salt thereof, in which:

A represents —(CH$_2$)$_n$—X—;

n represents 0;

X represents 1,3-azetidinylene, 1,3-pyrrolidinylene, or 1,3-piperdinylene (here, the nitrogen atom is bonded to the carbonyl group of —COY in the general formula (I));

Y represents —C($R_4$)=C($R_5$)($R_6$) or —C≡C—$R_7$;

when Z represents N, W represents N, while when Z represents CH, W represents N or CH;

$R_1$ represents an amino group;

any one of $R_2$ and $R_3$ represents a hydrogen atom or a methyl group, while the other represents a hydrogen atom, a halogen atom, a methyl group, a trifluoromethyl group, a methoxyethyl group, a methoxy group, a phenyl group, a 4-chlorophenyl group, a 2-thienyl group, or a cyano group; and when Y represents —C($R_4$)=C($R_5$)($R_6$), $R_4$, $R_5$ and $R_6$, which may be identical or different, each represent a hydrogen atom, a methyl group, a dimethylaminomethyl group, a methylethylaminomethyl group, a diethylaminomethyl group, a methylisopropylaminomethyl group, a 1-piperidinylmethyl group, or a 1-pyrrolidinylmethyl group;

when Y represents —C≡C—$R_7$, $R_7$ represents a methyl group.

In regard to the compound of the present invention represented by general formula (I), more preferred is a compound, or a salt thereof, in which:

A represents —(CH$_2$)$_n$—X—;

n represents 0;

$R_1$ represents an amino group;

any one of $R_2$ and $R_3$ represents a hydrogen atom or a methyl group, while the other represents a hydrogen atom, a halogen atom, a trifluoromethyl group, a methoxyethyl group, a phenyl group, a 2-thienyl group, or a cyano group;

(1) when Z represent N, and W represents N,

X represents 1,3-piperidinylene, and

Y represents a vinyl group;

(2) when Z represents CH, and W represents N,

X represents 1,3-pyrrolidinylene or 1,3-piperidinylene,

Y represents —C($R_4$)=C($R_5$)($R_6$) or —C≡C—($R_7$), and when Y represents —C($R_4$)=C($R_5$)($R_6$), $R_4$, $R_5$ and $R_6$, which may be identical or different, each represent a hydrogen atom, a methyl group, a dimethylaminomethyl group, a methylethylaminomethyl group, a diethylaminomethyl group, a methylisopropylaminomethyl group, a 1-piperidinylmethyl group, or a 1-pyrrolidinylmethyl group, when Y represents —C≡C—($R_7$), $R_7$ represents a methyl group; and (3) when Z represents CH, and W represents CH, X represents 1,3-azetidinylene or 1,3-pyrrolidinylene, Y represents —C($R_4$)=C($R_5$)($R_6$), and $R_4$, $R_5$ and $R_6$, which may be identical or different, each represent a hydrogen atom, a dimethylaminomethyl group, a methylethylaminomethyl group, a diethylaminomethyl group, a methylisopropylaminomethyl group, a 1-piperidinylmethyl group, or a 1-pyrrolidinylmethyl group.

In this case, in regard to the compound of the present invention represented by general formula (I), more preferred is a compound, or a salt thereof, in which:

A represents —(CH$_2$)$_n$—X—;

n represents 0;

$R_1$ represents an amino group;

any one of $R_2$ and $R_3$ represents a hydrogen atom or a methyl group, while the other represents a hydrogen atom, a halogen atom, a trifluoromethyl group, a methoxyethyl group, a phenyl group, a 2-thienyl group, or a cyano group;

(1) when Z represents N, and W represents N,

X represents 1,3-piperidinylene (here, the nitrogen atom is bonded to the carbonyl group of —COY in the general formula (I)), and Y represents a vinyl group;

(2) when Z represents CH, and W represents N,

X represents 1,3-pyrrolidinylene or 1,3-piperidinylene (here, the nitrogen atom is bonded to the carbonyl group of —COY in the general formula (I)), Y represents —C($R_4$)=C($R_5$)($R_6$) or —C≡C—($R_7$), and when Y represents —C($R_4$)=C($R_5$)($R_6$), $R_4$, $R_5$ and $R_6$, which may be identical or different, each represent a hydrogen atom, a methyl group, a dimethylaminomethyl group, a methylethylaminomethyl group, a diethylaminomethyl group, a methylisopropylaminomethyl group, a 1-piperidinylmethyl group, or a 1-pyrrolidinylmethyl group, e when Y represents —C≡C—($R_7$), $R_7$ represents a methyl group; and (3) when Z represents CH, and W represents CH,
X represents 1,3-azetidinylene or 1,3-pyrrolidinylene (here, the nitrogen atom is bonded to the carbonyl group of —COY in the general formula (I)),
Y represents —C($R_4$)=C($R_5$)($R_6$), and
$R_4$, $R_5$ and $R_6$, which may be identical or different, each represent a hydrogen atom, a dimethylaminomethyl group, a methylethylaminomethyl group, a diethylaminomethyl group, a methylisopropylaminomethyl group, a 1-piperidinylmethyl group, or a 1-pyrrolidinylmethyl group.

In regard to the compound of the present invention represented by general formula (I), more preferred is a compound, or a salt thereof, in which:
A represents —$(CH_2)_n$—X—;
n represents 0;
X represents 1,3-piperidinylene;
Y represents a vinyl group;
Z represents CH;
W represents N;
$R_1$ represents an amino group; and
any one of $R_2$ and $R_3$ represents a hydrogen atom, while the other represents a hydrogen atom, a halogen atom, or a cyano group.

In this case, in regard to the compound of the present invention represented by general formula (I), more preferred is a compound, or a salt thereof, in which:
A represents —$(CH_2)_n$—X—;
n represents 0;
X represents 1,3-piperidinylene (here, the nitrogen atom is bonded to the carbonyl group of —COY in the general formula (I));
Y represents a vinyl group;
Z represents CH;
W represents N;
$R_1$ represents an amino group; and
any one of $R_2$ and $R_3$ represents a hydrogen atom, while the other represents a hydrogen atom, a halogen atom, or a cyano group.

In regard to the compound of the present invention represented by general formula (I), more preferred is a compound, or a salt thereof, in which:
A represents —$(CH_2)_n$—X—;
n represents 0;
X represents 1,3-piperidinylene;
Y represents a vinyl group;
Z represents CH;
W represents N;
$R_1$ represents an amino group; and
any one of $R_2$ and $R_3$ represents a hydrogen atom, while the other represents a hydrogen atom or a halogen atom.

In this case, in regard to the compound of the present invention represented by general formula (I), more preferred is a compound, or a salt thereof, in which:
A represents —$(CH_2)_n$—X—;
n represents 0;
X represents 1,3-piperidinylene (here, the nitrogen atom is bonded to the carbonyl group of —COY in the general formula (I));
Y represents a vinyl group;
Z represents CH;
W represents N;
$R_1$ represents an amino group; and
any one of $R_2$ and $R_3$ represents a hydrogen atom, while the other represents a hydrogen atom or a halogen atom.

Specific examples of the compound of the present invention include those compounds produced in the Examples described below; however, the compound is not intended to be limited to these.

Suitable examples of the compound of the present invention include the following compounds:
(1) (R)-1-(1-acryloylpiperidin-3-yl)-4-amino-N-(5-chlorobenzo[d]oxazol-2-yl)-1H-pyrazolo[3,4-d]pyrimidine-3-carboxamide (Example Compound 1)
(2) (R)-1-(1-acryloylpiperidin-3-yl)-4-amino-N-(5-bromobenzo[d]oxazol-2-yl)-1H-pyrazolo[3,4-d]pyrimidine-3-carboxamide (Example Compound 2)
(3) (R)-1-(1-acryloylpiperidin-3-yl)-4-amino-N-(5-(thiophen-2-yl)benzo[d]oxazol-2-yl)-1H-pyrazolo[3,4-d]pyrimidine-3-carboxamide (Example Compound 3)
(4) (R)-4-amino-N-(5-chlorobenzo[d]oxazol-2-yl)-1-(1-methacryloylpiperidin-3-yl)-1H-pyrazolo[3,4-d]pyrimidine-3-carboxamide (Example Compound 4)
(5) (R,E)-4-amino-N-(5-chlorobenzo[d]oxazol-2-yl)-1-(1-(but-2-enoyl)piperidin-3-yl)-1H-pyrazolo[3,4-d]pyrimidine-3-carboxamide (Example Compound 5)
(6) (R)-1-(1-acryloylpiperidin-3-yl)-4-amino-N-(5-cyanobenzo[d]oxazol-2-yl)-1H-pyrazolo[3,4-d]pyrimidine-3-carboxamide (Example Compound 6)
(7) (R)-1-(1-acryloylpiperidin-3-yl)-4-amino-N-(5-methoxybenzo[d]oxazol-2-yl)-1H-pyrazolo[3,4-d]pyrimidine-3-carboxamide (Example Compound 7)
(8) (R)-1-(1-acryloylpiperidin-3-yl)-4-amino-N-(5-(2-methoxyethyl)benzo[d]oxazol-2-yl)-1H-pyrazolo[3,4-d]pyrimidine-3-carboxamide (Example Compound 8)
(9) (R)-1-(1-acryloylpiperidin-3-yl)-4-amino-N-(oxazolo[4,5-b]pyridin-2-yl)-1H-pyrazolo[3,4-d]pyrimidine-3-carboxamide (Example Compound 9)
(10) (R)-1-(1-acryloylpiperidin-3-yl)-4-amino-N-(4-methylbenzo[d]oxazol-2-yl)-1H-pyrazolo[3,4-d]pyrimidine-3-carboxamide (Example Compound 10)
(11) (R)-4-amino-N-(5-fluorobenzo[d]oxazol-2-yl)-1-(1-methacryloylpiperidin-3-yl)-1H-pyrazolo[3,4-d]pyrimidine-3-carboxamide (Example Compound 11)
(12) (R)-1-(1-acryloylpiperidin-3-yl)-4-amino-N-(5-fluorobenzo[d]oxazol-2-yl)-1H-pyrazolo[3,4-d]pyrimidine-3-carboxamide (Example Compound 12)
(13) (R)-1-(1-acryloylpiperidin-3-yl)-4-amino-N-(benzo[d]oxazol-2-yl)-1H-pyrazolo[3,4-d]pyrimidine-3-carboxamide (Example Compound 13)
(14) (R,E)-4-amino-N-(benzo[d]oxazol-2-yl)-1-(1-(but-2-enoyl)piperidin-3-yl)-1H-pyrazolo[3,4-d]pyrimidine-3-carboxamide (Example Compound 14)
(15) (R,E)-4-amino-N-(5-chlorobenzo[d]oxazol-2-yl)-1-(1-(4-(dimethylamino)but-2-enoyl)piperidin-3-yl)-1H-pyrazolo[3,4-d]pyrimidine-3-carboxamide (Example Compound 15)
(16) (R,E)-4-amino-N-(5-chlorobenzo[d]oxazol-2-yl)-1-(1-(4-(ethyl(methyl)amino)but-2-enoyl)piperidin-3-yl)-1H-pyrazolo[3,4-d]pyrimidine-3-carboxamide (Example Compound 16)
(17) (R,E)-4-amino-N-(5-chlorobenzo[d]oxazol-2-yl)-1-(1-(4-(diethylamino)but-2-enoyl)piperidin-3-yl)-1H-pyrazolo[3,4-d]pyrimidine-3-carboxamide (Example Compound 17)
(18) (R,E)-4-amino-N-(5-chlorobenzo[d]oxazol-2-yl)-1-(1-(4-(isopropyl(methyl)amino)but-2-enoyl)piperidin-3-yl)-1H-pyrazolo[3,4-d]pyrimidine-3-carboxamide (Example Compound 18)

(19) (R,E)-4-amino-N-(5-chlorobenzo[d]oxazol-2-yl)-1-(1-(4-(pyrrolidin-1-yl)but-2-enoyl)piperidin-3-yl)-1H-pyrazolo[3,4-d]pyrimidine-3-carboxamide (Example Compound 19)

(20) (R,E)-4-amino-N-(5-chlorobenzo[d]oxazol-2-yl)-1-(1-(4-(piperidin-1-yl)but-2-enoyl)piperidin-3-yl)-1H-pyrazolo[3,4-d]pyrimidine-3-carboxamide (Example Compound 20)

(21) (R,E)-4-amino-N-(5-(thiophen-2-yl)benzo[d]oxazol-2-yl)-1-(1-(4-(dimethylamino)but-2-enoyl)piperidin-3-yl)-1H-pyrazolo[3,4-d]pyrimidine-3-carboxamide (Example Compound 21)

(22) (R)-4-amino-N-(benzo[d]oxazol-2-yl)-1-(1-(but-2-ynoyl)piperidin-3-yl)-1H-pyrazolo[3,4-d]pyrimidine-3-carboxamide (Example Compound 22)

(23) (R)-1-(1-acryloylpiperidin-3-yl)-4-amino-N-(5,6-dimethylbenzo[d]oxazol-2-yl)-1H-pyrazolo[3,4-d]pyrimidine-3-carboxamide (Example Compound 23)

(24) (R)-1-(1-acryloylpyrrolidin-3-yl)-4-amino-N-(5-chlorobenzo[d]oxazol-2-yl)-1H-pyrazolo[3,4-d]pyrimidine-3-carboxamide (Example Compound 24)

(25) (R,E)-4-amino-N-(5-chlorobenzo[d]oxazol-2-yl)-1-(1-(but-2-enoyl)pyrrolidin-3-yl)-1H-pyrazolo[3,4-d]pyrimidine-3-carboxamide (Example Compound 25)

(26) (R,E)-4-amino-N-(5-chlorobenzo[d]oxazol-2-yl)-1-(1-(3-methylbut-2-enoyl)pyrrolidin-3-yl)-1H-pyrazolo[3,4-d]pyrimidine-3-carboxamide (Example Compound 26)

(27) (R)-1-(1-acryloylpyrrolidin-3-yl)-4-amino-N-(benzo[d]oxazol-2-yl)-1H-pyrazolo[3,4-d]pyrimidine-3-carboxamide (Example Compound 27)

(28) (R)-1-(1-acryloylpyrrolidin-3-yl)-4-amino-N-(5-(thiophen-2-yl)benzo[d]oxazol-2-yl)-1H-pyrazolo[3,4-d]pyrimidine-3-carboxamide (Example Compound 28)

(29) (R)-1-(1-acryloylpyrrolidin-3-yl)-4-amino-N-(5-methylbenzo[d]oxazol-2-yl)-1H-pyrazolo[3,4-d]pyrimidine-3-carboxamide (Example Compound 29)

(30) (R)-1-(1-acryloylpyrrolidin-3-yl)-4-amino-N-(5-fluorobenzo[d]oxazol-2-yl)-1H-pyrazolo[3,4-d]pyrimidine-3-carboxamide (Example Compound 30)

(31) (R)-1-(1-acryloylpyrrolidin-3-yl)-4-amino-N-(5-(4-chlorophenyl)benzo[d]oxazol-2-yl)-1H-pyrazolo[3,4-d]pyrimidine-3-carboxamide (Example Compound 31)

(32) (R,E)-4-amino-N-(5-chlorobenzo[d]oxazol-2-yl)-1-(1-(4-(dimethylamino)but-2-enoyl)pyrrolidin-3-yl)-1H-pyrazolo[3,4-d]pyrimidine-3-carboxamide (Example Compound 32)

(33) (R,E)-4-amino-N-(5-chlorobenzo[d]oxazol-2-yl)-1-(1-(4-(ethyl(methyl)amino)but-2-enoyl)pyrrolidin-3-yl)-1H-pyrazolo[3,4-d]pyrimidine-3-carboxamide (Example Compound 33)

(34) (R,E)-4-amino-N-(5-chlorobenzo[d]oxazol-2-yl)-1-(1-(4-(diethylamino)but-2-enoyl)pyrrolidin-3-yl)-1H-pyrazolo[3,4-d]pyrimidine-3-carboxamide (Example Compound 34)

(35) (R,E)-4-amino-N-(5-chlorobenzo[d]oxazol-2-yl)-1-(1-(4-(isopropyl(methyl)amino)but-2-enoyl)pyrrolidin-3-yl)-1H-pyrazolo[3,4-d]pyrimidine-3-carboxamide (Example Compound 35)

(36) (R,E)-4-amino-N-(5-chlorobenzo[d]oxazol-2-yl)-1-(1-(4-(pyrrolidin-1-yl)but-2-enoyl)pyrrolidin-3-yl)-1H-pyrazolo[3,4-d]pyrimidine-3-carboxamide (Example Compound 36)

(37) (R,E)-4-amino-N-(5-chlorobenzo[d]oxazol-2-yl)-1-(1-(4-(piperidin-1-yl)but-2-enoyl)pyrrolidin-3-yl)-1H-pyrazolo[3,4-d]pyrimidine-3-carboxamide (Example Compound 37)

(38) (R)-1-(1-acryloylpyrrolidin-3-yl)-4-amino-N-(5-methoxybenzo[d]oxazol-2-yl)-1H-pyrazolo[3,4-d]pyrimidine-3-carboxamide (Example Compound 38)

(39) (R)-1-(1-acryloylpyrrolidin-3-yl)-4-amino-N-(5-cyanobenzo[d]oxazol-2-yl)-1H-pyrazolo[3,4-d]pyrimidine-3-carboxamide (Example Compound 39)

(40) (R)-1-(1-acryloylpyrrolidin-3-yl)-4-amino-N-(5-(2-methoxyethyl)benzo[d]oxazol-2-yl)-1H-pyrazolo[3,4-d]pyrimidine-3-carboxamide (Example Compound 40)

(41) (R)-1-(1-acryloylpyrrolidin-3-yl)-4-amino-N-(5-phenylbenzo[d]oxazol-2-yl)-1H-pyrazolo[3,4-d]pyrimidine-3-carboxamide (Example Compound 41)

(42) (R,E)-4-amino-N-(5-phenylbenzo[d]oxazol-2-yl)-1-(1-(4-(dimethylamino)but-2-enoyl)pyrrolidin-3-yl)-1H-pyrazolo[3,4-d]pyrimidine-3-carboxamide (Example Compound 42)

(43) (R)-1-(1-acryloylpyrrolidin-3-yl)-4-amino-N-(5-(trifluoromethyl)benzo[d]oxazol-2-yl)-1H-pyrazolo[3,4-d]pyrimidine-3-carboxamide (Example Compound 43)

(44) (R,E)-4-amino-N-(5-(trifluoromethyl)benzo[d]oxazol-2-yl)-1-(1-(4-(dimethylamino)but-2-enoyl)pyrrolidin-3-yl)-1H-pyrazolo[3,4-d]pyrimidine-3-carboxamide (Example Compound 44)

(45) 1-(1-Acryloylazetidin-3-yl)-4-amino-N-(5-chlorobenzo[d]oxazol-2-yl)-1H-pyrazolo[3,4-d]pyrimidine-3-carboxamide (Example Compound 45)

(46) 7-(1-Acryloylazetidin-3-yl)-4-amino-N-(5-chlorobenzo[d]oxazol-2-yl)-7H-pyrrolo[2,3-d]pyrimidine-5-carboxamide (Example Compound 46)

(47) (E)-4-amino-N-(5-chlorobenzo[d]oxazol-2-yl)-7-(1-(4-(dimethylamino)but-2-enoyl)azetidin-3-yl) 7H-pyrrolo[2,3-d]pyrimidine-5-carboxamide (Example Compound 47)

(48) (R)-7-(1-acryloylpyrrolidin-3-yl)-4-amino-N-(5-chlorobenzo[d]oxazol-2-yl)-7H-pyrrolo[2,3-d]pyrimidine-5-carboxamide (Example Compound 48)

(49) (R,E)-4-amino-N-(5-chlorobenzo[d]oxazol-2-yl)-7-(1-(4-(dimethylamino)but-2-enoyl)pyrrolidin-3-yl) 7H-pyrrolo[2,3-d]pyrimidine-5-carboxamide (Example Compound 49)

(50) (R,E)-4-amino-N-(5-chlorobenzo[d]oxazol-2-yl)-7-(1-(4-(ethyl(methyl)amino)but-2-enoyl)pyrrolidin-3-yl) 7H-pyrrolo[2,3-d]pyrimidine-5-carboxamide (Example Compound 50)

(51) (R,E)-4-amino-N-(5-chlorobenzo[d]oxazol-2-yl)-7-(1-(4-(diethylamino)but-2-enoyl)pyrrolidin-3-yl) 7H-pyrrolo[2,3-d]pyrimidine-5-carboxamide (Example Compound 51)

(52) (R,E)-4-amino-N-(5-chlorobenzo[d]oxazol-2-yl)-7-(1-(4-(isopropyl(methyl)amino)but-2-enoyl)pyrrolidin-3-yl) 7H-pyrrolo[2,3-d]pyrimidine-5-carboxamide (Example Compound 52)

(53) (R,E)-4-amino-N-(5-chlorobenzo[d]oxazol-2-yl)-7-(1-(4-(pyrrolidin-1-yl)but-2-enoyl)pyrrolidin-3-yl) 7H-pyrrolo[2,3-d]pyrimidine-5-carboxamide (Example Compound 53)

(54) (R,E)-4-amino-N-(5-chlorobenzo[d]oxazol-2-yl)-7-(1-(4-(piperidin-1-yl)but-2-enoyl)pyrrolidin-3-yl) 7H-pyrrolo[2,3-d]pyrimidine-5-carboxamide (Example Compound 54)

(55) (R)-7-(1-acryloylpyrrolidin-3-yl)-4-amino-N-(5-phenylbenzo[d]oxazol-2-yl)-7H-pyrrolo[2,3-d]pyrimidine-5-carboxamide (Example Compound 55)

(56) (R,E)-4-amino-N-(5-phenylbenzo[d]oxazol-2-yl)-7-(1-(4-(dimethylamino)but-2-enoyl)pyrrolidin-3-yl) 7H-pyrrolo[2,3-d]pyrimidine-5-carboxamide (Example Compound 56)

(57) (R,E)-4-amino-N-(5-phenylbenzo[d]oxazol-2-yl)-7-(1-(4-(ethyl(methyl)amino)but-2-enoyl)pyrrolidin-3-yl) 7H-pyrrolo[2,3-d]pyrimidine-5-carboxamide (Example Compound 57)

(58) (R,E)-4-amino-N-(5-phenylbenzo[d]oxazol-2-yl)-7-(1-(4-(diethylamino)but-2-enoyl)pyrrolidin-3-yl) 7H-pyrrolo[2,3-d]pyrimidine-5-carboxamide (Example Compound 58)

(59) (R,E)-4-amino-N-(5-phenylbenzo[d]oxazol-2-yl)-7-(1-(4-(isopropyl(methyl)amino)but-2-enoyl)pyrrolidin-3-yl) 7H-pyrrolo[2,3-d]pyrimidine-5-carboxamide (Example Compound 59)

(60) (R,E)-4-amino-N-(5-phenylbenzo[d]oxazol-2-yl)-7-(1-(4-(pyrrolidin-1-yl)but-2-enoyl)pyrrolidin-3-yl) 7H-pyrrolo[2,3-d]pyrimidine-5-carboxamide (Example Compound 60)

(61) (R,E)-4-amino-N-(5-phenylbenzo[d]oxazol-2-yl)-7-(1-(4-(piperidin-1-yl)but-2-enoyl)pyrrolidin-3-yl) 7H-pyrrolo[2,3-d]pyrimidine-5-carboxamide (Example Compound 61)

(64) (R)-1-(1-acryloylpiperidin-3-yl)-4-amino-N-(7-chlorobenzo[d]oxazol-2-yl)-1H-pyrazolo[3,4-d]pyrimidine-3-carboxamide (Example Compound 64)

(65) (S)-1-(1-acryloylpyrrolidin-3-yl)-4-amino-N-(benzo[d]oxazol-2-yl)-1H-pyrazolo[3,4-d]pyrimidine-3-carboxamide (Example Compound 65)

(66) 1-((1-Acryloylpyrrolidin-3-yl)methyl)-4-amino-N-(benzo[d]oxazol-2-yl)-1H-pyrazolo[3,4-d]pyrimidine-3-carboxamide (Example Compound 66)

(67) 1-((1-Acryloylpiperidin-3-yl)methyl)-4-amino-N-(benzo[d]oxazol-2-yl)-1H-pyrazolo[3,4-d]pyrimidine-3-carboxamide (Example Compound 67)

(68) 1-((1-Acryloylpiperidin-4-yl)methyl)-4-amino-N-(benzo[d]oxazol-2-yl)-1H-pyrazolo[3,4-d]pyrimidine-3-carboxamide (Example Compound 68)

(69) 1-(1-Acryloylpiperidin-4-yl)-4-amino-N-(benzo[d]oxazol-2-yl)-1H-pyrazolo[3,4-d]pyrimidine-3-carboxamide (Example Compound 69)

(70) 1-((1-Acryloylazetidin-3-yl)methyl)-4-amino-N-(benzo[d]oxazol-2-yl)-1H-pyrazolo[3,4-d]pyrimidine-3-carboxamide (Example Compound 70)

(71) 1-((1S,4S)-4-acrylamidocyclohexyl)-4-amino-N-(benzo[d]oxazol-2-yl)-1H-pyrazolo[3,4-d]pyrimidine-3-carboxamide (Example Compound 71)

(72) 1-((1R,4R)-4-acrylamidocyclohexyl)-4-amino-N-(benzo[d]oxazol-2-yl)-1H-pyrazolo[3,4-d]pyrimidine-3-carboxamide (Example Compound 72)

(73) (S,E)-4-amino-N-(benzo[d]oxazol-2-yl)-1-(1-(4-(dimethylamino)but-2-enoyl)pyrrolidin-3-yl)-1H-pyrazolo[3,4-d]pyrimidine-3-carboxamide (Example Compound 73)

(74) 1-(1-Acryloylazetidin-3-yl)-4-amino-N-(benzo[d]oxazol-2-yl)-1H-pyrazolo[3,4-d]pyrimidine-3-carboxamide (Example Compound 74)

(75) 1-((1-Acryloylazetidin-3-yl)methyl)-4-amino-N-(5-fluorobenzo[d]oxazol-2-yl)-1H-pyrazolo[3,4-d]pyrimidine-3-carboxamide (Example Compound 75)

(76) 1-((1-Acryloylazetidin-3-yl)methyl)-4-amino-N-(5-chlorobenzo[d]oxazol-2-yl)-1H-pyrazolo[3,4-d]pyrimidine-3-carboxamide (Example Compound 76)

(77) 1-((1-Acryloylpiperidin-4-yl)methyl)-4-amino-N-(5-fluorobenzo[d]oxazol-2-yl)-1H-pyrazolo[3,4-d]pyrimidine-3-carboxamide (Example Compound 77)

(78) 1-((1S,4S)-4-acrylamidocyclohexyl)-4-amino-N-(5-chlorobenzo[d]oxazol-2-yl)-1H-pyrazolo[3,4-d]pyrimidine-3-carboxamide (Example Compound 78)

(79) 1-(1-Acryloylazetidin-3-yl)-4-amino-N-(5-fluorobenzo[d]oxazol-2-yl)-1H-pyrazolo[3,4-d]pyrimidine-3-carboxamide (Example Compound 79)

(80) 1-((1-Acryloylpiperidin-4-yl)methyl)-4-amino-N-(5-chlorobenzo[d]oxazol-2-yl)-1H-pyrazolo[3,4-d]pyrimidine-3-carboxamide (Example Compound 80)

(81) 1-((1S,4S)-4-acrylamidocyclohexyl)-4-amino-N-(5-fluorobenzo[d]oxazol-2-yl)-1H-pyrazolo[3,4-d]pyrimidine-3-carboxamide (Example Compound 81)

(82) 1-(1-Acryloylpyrrolidin-3-yl)-4-amino-N-(benzo[d]oxazol-2-yl)-1H-pyrazolo[3,4-d]pyrimidine-3-carboxamide (Example Compound 82)

(83) 1-(1-Acryloylpyrrolidin-3-yl)-4-amino-N-(5-fluorobenzo[d]oxazol-2-yl)-1H-pyrazolo[3,4-d]pyrimidine-3-carboxamide (Example Compound 83)

(84) 1-(1-Acryloylpyrrolidin-3-yl)-4-amino-N-(5-chlorobenzo[d]oxazol-2-yl)-1H-pyrazolo[3,4-d]pyrimidine-3-carboxamide (Example Compound 84)

(85) 1-(3-Acrylamidopropyl)-4-amino-N-(benzo[d]oxazol-2-yl)-1H-pyrazolo[3,4-d]pyrimidine-3-carboxamide (Example Compound 85)

(86) 1-(2-Acrylamidoethyl)-4-amino-N-(benzo[d]oxazol-2-yl)-1H-pyrazolo[3,4-d]pyrimidine-3-carboxamide (Example Compound 86)

The probe compound according to the present invention includes a detectable label or affinity tag that can be combined with the compound of the present invention, and a linker. The linker links the compound of the present invention to the label or tag.

There are no particular limitations on the detectable label or affinity tag as long as the label or affinity tag can detect the binding of the probe according to the present invention with BTK; however, a label or affinity tag containing a functional group capable of binding to the linker unit through, for example, alkylation or amidation is desired. Preferably, for example, BODIPY (registered trademark) FL, BODIPY (registered trademark) R6G, BODIPY (registered trademark) TMR, BODIPY (registered trademark) 581/591, and BODIPY (registered trademark) TR, are employed as luminophores, and for example, biotin is employed as a binding group. More preferably, BODIPY (registered trademark) FL and biotin are employed.

The linker is not particularly limited as long as the linker is a part that links the label or tag with the compound of the present invention. However, it is desirable that the linker has an appropriate length, properties that do not significantly affect the compound of the present invention, and a functional group that can extend the label or tag. Preferred examples of the linker include:

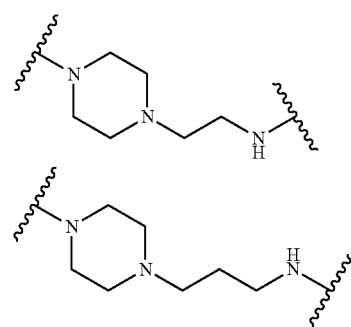

-continued

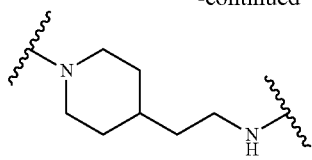

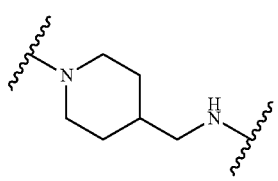

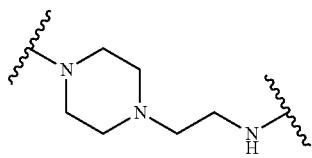 [SMILES: *NCCN1CCN(*)CC1]

and a more preferred example is:

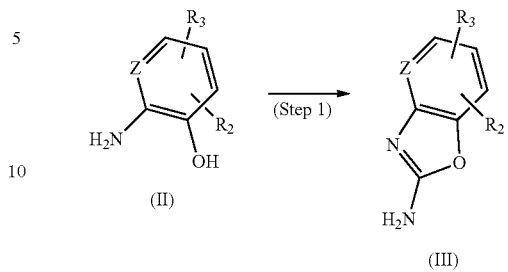

Preferred examples of the probe according to the present invention include 4-amino-N-(benzo[d]oxazol-2-yl)-1-((R)-1-((E)-4-(4-(2-(5-((3aS,4S,6aR)-2-oxohexahydro-1H-thieno[3,4-d]imidazol-4-yl)pentanamido)ethyl)piperazin-1-yl)but-2-enoyl)piperidin-3-yl)-1H-pyrazolo[3,4-d]pyrimidine-3-carboxamide, and (R,E)-7-(3-((2-(4-(4-(3-(4-amino-3-(benzo[d]oxazol-2-ylcarbamoyl)-1H-pyrazolo[3,4-d]pyrimidin-1-yl)piperidin-1-yl)-4-oxobut-2-en-1-yl)piperazin-1-yl)ethyl)amino)-3-oxopropyl) 5,5-difluoro-1,3-dimethyl-5H-dipyrrolo[1,2-c:2',1'-f][1,3,2]diazaborinin-4-ium-5-uide.

The binding state of the compound of the present invention and BTK can be detected or quantitatively analyzed by co-treating the probe according to the present invention with, for example, a specimen in the blood or in the spleen, or by co-treating the probe with a cell extract derived from, for example, the blood or the spleen. For the detection or quantitative analysis, for example, biochemical techniques (for example, luminescence and fluorescence) can be used.

Next, a method for producing the compound related to the present invention is explained.

Compound (I) of the present invention can be produced by, for example, the production method described below or by the method disclosed in Examples. However, the method for producing compound (I) of the present invention is not intended to be limited to these reaction examples.

Production Method 1

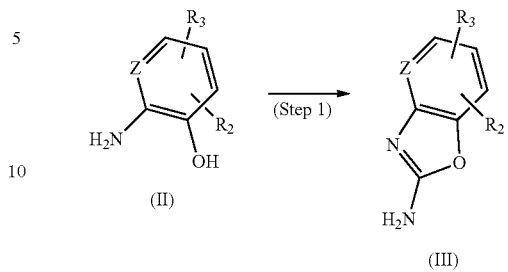

wherein Z, $R_2$ and $R_3$ respectively have the same meanings as defined above.

(Step 1) The present step is a process for synthesizing a benzoxazole compound represented by general formula (III) from an aminophenol represented by general formula (II).

Examples of the reagent used include cyano compounds such as bromocyan, chlorocyan, iodocyan, and 1,1-carbonimidoylbis-1H-imidazol e. The reaction is carried out using 0.5 to 5 moles, and preferably 0.9 to 1.5 moles, of the cyano compound with respect to 1 mole of the compound represented by general formula (II). Meanwhile, regarding the relevant cyano compound, a commercially available product can be used, or the cyano compound can be produced according to a known method. The solvent used in the reaction may be any solvent as long as it does not adversely affect the reaction, and for example, alcohols (for example, methanol and ethanol), hydrocarbons (for example, benzene, toluene, and xylene), halogenated hydrocarbons (for example, methylene chloride, chloroform, and 1,2-dichloroethane), nitriles (for example, acetonitrile), ethers (for example, dimethoxyethane and tetrahydrofuran), aprotic polar solvents (for example, N,N-dimethylformamide, dimethyl sulfoxide, and hexamethylphosphoramide), water, or mixtures thereof are used. The reaction time is 0.1 to 100 hours, and preferably 0.5 to 24 hours. The reaction temperature is 0° C. to 120° C., and preferably 0° C. to 90° C.

The compound represented by general formula (III) that is obtainable as such is isolated and purified by known separation and purification means, for example, concentration, concentration under reduced pressure, crystallization, solvent extraction, reprecipitation, and chromatography, or can be subjected to the subsequent step without being isolated and purified.

Production Method 2

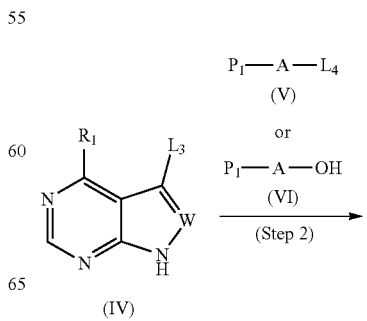

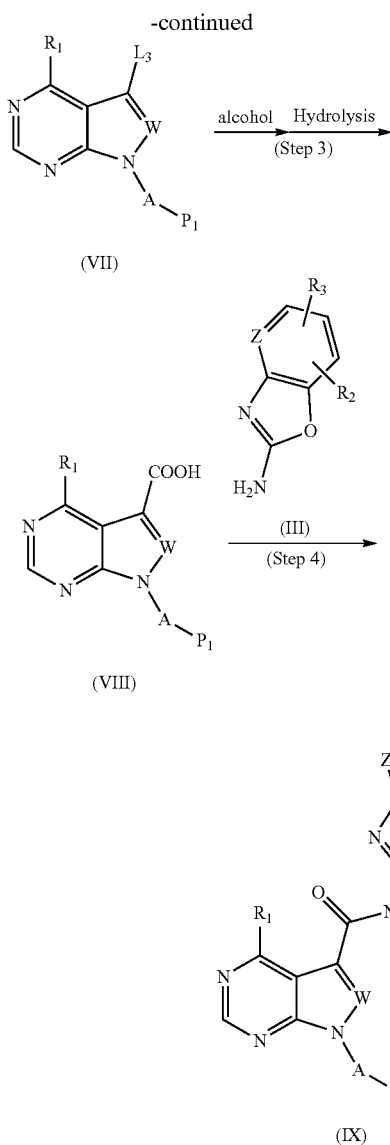

wherein $L_3$ and $L_4$ each represent a leaving group; $P_1$ represents a protective group of the amino group contained in A; and W, A, Y, Z, $R_1$, $R_2$ and $R_3$ respectively have the same meanings as defined above.

(Step 2) The present step is a process for producing a compound represented by general formula (VII) using a compound represented by general formula (IV) and a compound represented by general formula (V) or general formula (VI).

When the compound represented by general formula (V) is used as an alkylation reagent, the compound represented by general formula (VII) can be produced in the presence of a base. In general formula (V), $L_4$ represents a leaving group, for example, a chlorine atom, a bromine atom, an iodine atom, a methanesulfonic acid ester, or a p-toluenesulfonic acid ester, and a commercially available product may be used, or the compound can be produced according to a known method. The compound represented by general formula (V) can be used in an amount of 1 to 10 moles, and preferably 1 to 5 moles, with respect to 1 mole of the compound represented by general formula (IV).

Examples of the base include inorganic bases such as sodium hydrogen carbonate, sodium carbonate, potassium carbonate, cesium carbonate, cesium hydroxide, sodium hydride, and potassium hydride; and organic amines such as trimethylamine, triethylamine, tripropylamine, diisopropylethylamine, N-methylmorpholine, pyridine, 4-(N,N-dimethylamino)pyridine, lutidine, and collidine. Regarding the amount of use of the base, the base can be used in an amount of 1 to 100 moles, and preferably 2 to 10 moles, with respect to 1 mole of the compound represented by general formula (IV).

For the solvent, for example, N,N-dimethylformamide, N,N-dimethylacetamide, dimethyl sulfoxide, tetrahydrofuran, 1,4-dioxane, N-methylpyrrolidin-2-one, and acetonitrile can be used singly or as mixtures. The reaction time is 0.1 to 100 hours, and preferably 0.5 to 24 hours. The reaction temperature is 0° C. to a temperature at which the solvent boils, and preferably 0° C. to 100° C.

When the compound of general formula (VI) is used as an alkylation reagent, the compound represented by general formula (VII) can be produced using the Mitsunobu reaction. Usually, the present process can be carried out according to a known method (for example, Chemical Reviews, Vol. 109, p. 2551, 2009), and for example, the process can be carried out in the presence of a Mitsunobu reagent and a phosphine reagent, in a solvent which does not adversely affect the reaction. The present process is usually carried out using the compound represented by general formula (VI) in an amount of 1 to 10 moles, and preferably 1 to 5 moles, with respect to 1 mole of the compound represented by general formula (IV).

Examples of the Mitsunobu reagent include diethyl azodicarboxylate and diisopropyl azodicarboxylate. Regarding the amount of use of the Mitsunobu reagent, the process is carried out using the reagent in an amount of 1 to 10 moles, and preferably 1 to 5 moles, with respect to 1 mole of the compound represented by general formula (IV).

Examples of the phosphine reagent include triphenylphosphine and tributylphosphine. Regarding the phosphine reagent, the process is carried out using the reagent in an amount of 1 to 10 moles, and preferably 1 to 5 moles, with respect to 1 mole of the compound represented by general formula (IV).

The reaction solvent is not particularly limited as long as the reaction solvent does not interrupt the reaction; however, for example, toluene, benzene tetrahydrofuran, 1,4-dioxane, dimethylformamide, dimethylacetamide, N-methylpyrrolidinone, dimethyl sulfoxide, or mixed solvents thereof are suitable.

The reaction temperature is usually −78° C. to 200° C., and preferably 0° C. to 50° C. The reaction time is usually 5 minutes to 3 days, and preferably 10 minutes to 10 hours.

The compound represented by general formula (VII) that is obtainable as such is isolated and purified by known separation and purification means, for example, concentration, concentration under reduced pressure, crystallization, solvent extraction, reprecipitation, and chromatography, or is subjected to the subsequent process without being isolated and purified.

(Step 3) The present step is a process for producing a compound represented by general formula (VIII) by allowing the compound represented by general formula (VII) to react with, for example, a transition metal and optionally a base, in a carbon monoxide atmosphere in the presence of an alcohol, in a solvent which does not adversely affect the reaction.

In general formula (VII), the leaving group represented by $L_3$ is a bromine atom or an iodine atom, and regarding the relevant compound, a commercially available product may be used, or the compound can be produced according to a known method.

In the present process, the pressure of carbon monoxide is usually 1 atmosphere to 10 atmospheres, and preferably 1 atmosphere to 5 atmospheres. Regarding the amount of use of the alcohol compound, the compound can be used in an amount of 1 to 10 moles, and preferably 1 to 5 moles, with respect to 1 mole of the compound represented by general formula (VII). Examples of the alcohol compound include methanol, ethanol, propanol, isopropyl alcohol, diethylaminoethanol, isobutanol, 4-(2-hydroxyethyl)morpholine, 3-morpholinopropanol, and diethylaminopropanol.

The transition metal catalyst that can be used in the present process is, for example, a palladium catalyst (for example, palladium acetate, tris(dibenzylideneacetone)dipalladium, bis(triphenylphosphine)palladium(II) dichloride, or 1,1'-bis(diphenylphosphino)ferrocene-palladium(II) dichloride-dichloromethane complex), and if necessary, a ligand (for example, triphenylphosphine, xantphos, or tri-tert-butylphosphine) is added thereto. The amount of use of the transition metal catalyst may vary depending on the kind of the catalyst; however, the amount of use is usually 0.0001 to 1 mole, and preferably 0.001 to 0.5 moles, with respect to 1 mole of the compound represented by general formula (VII). The amount of use of the ligand is usually 0.0001 to 4 moles, and preferably 0.01 to 2 moles, with respect to 1 mole of the compound represented by general formula (VII).

Furthermore, a base can be added to the reaction, as necessary. Examples of the base include organic bases such as triethylamine, diisopropylethylamine, pyridine, lutidine, collidine, 4-dimethylaminopyridine, N-methylmorpholine, potassium tert-butyrate, sodium tert-butyrate, sodium methoxide, sodium ethoxide, lithium hexamethyldisilazide, sodium hexamethyldisilazide, potassium hexamethyldisilazide, and butyllithium; and inorganic bases such as sodium hydrogen carbonate, sodium carbonate, potassium carbonate, cesium carbonate, sodium hydroxide, and sodium hydride. The amount of use of the base is usually 0.1 to 50 moles, and preferably 1 to 20 moles, with respect to 1 mole of the compound represented by general formula (VII).

The reaction solvent is not particularly limited as long as the reaction solvent does not interrupt the reaction, and examples thereof include hydrocarbons (for example, benzene, toluene, and xylene), nitriles (for example, acetonitrile), ethers (for example, dimethoxyethane, tetrahydrofuran, and 1,4-dioxane), alcohols (for example, methanol and ethanol), aprotic polar solvents (for example, dimethylformamide, dimethylacetamide, N-methylpyrrolidinone, dimethyl sulfoxide, and hexamethylphosphoramide), water, or mixtures thereof. The reaction time is 0.1 to 100 hours, and preferably 0.5 to 24 hours. The reaction temperature is 0° C. to a temperature at which the solvent boils, and preferably 0° C. to 150° C.

After this reaction, since a mixture of the carboxylic acid compound (VIII) and an ester form corresponding to the alcohol used is obtained, a hydrolysis reaction is conducted in order to converge the mixture into the compound represented by general formula (VIII). Hydrolysis is carried out using a base, and examples thereof include organic bases such as diethylamine, diisopropylamine, potassium tert-butyrate, sodium tert-butyrate, sodium methoxide, sodium ethoxide, lithium hexamethyldisilazide, sodium hexamethyldisilazide, potassium hexamethyldisilazide, and butyllithium; and inorganic bases such as sodium hydrogen carbonate, sodium carbonate, potassium carbonate, cesium carbonate, and sodium hydroxide.

The reaction solvent is not particularly limited as long as the reaction solvent does not interrupt the reaction, and examples thereof include hydrocarbons (for example, benzene, toluene, and xylene), nitriles (for example, acetonitrile), ethers (for example, dimethoxyethane, tetrahydrofuran, and 1,4-dioxane), alcohols (for example, methanol and ethanol), aprotic polar solvents (for example, dimethylformamide, dimethylacetamide, N-methylpyrrolidinone, dimethyl sulfoxide, and hexamethylphosphoramide), water, or mixtures thereof. The reaction time is 0.1 to 100 hours, and preferably 0.5 to 24 hours. The reaction temperature is 0° C. to a temperature at which the solvent boils, and preferably 0° C. to 150° C.

The compound represented by general formula (VIII) that is obtainable as such is isolated and purified by known separation and purification means, for example, concentration, concentration under reduced pressure, crystallization, solvent extraction, reprecipitation, and chromatography, or is subjected to the subsequent process without being isolated and purified.

(Step 4) The present step is a process for producing a compound represented by general formula (IX) by performing an amidation reaction using compounds represented by general formula (VIII) and general formula (III).

The process is carried out using the compound of general formula (III) in an amount of 0.5 to 10 moles, and preferably 1 to 3 moles, with respect to 1 mole of the compound represented by general formula (VIII), in the presence of an appropriate condensing agent or an activating agent as an amidation reagent.

The reaction solvent is not particularly limited as long as the reaction solvent does not interrupt the reaction, and for example, isopropanol, tert-butyl alcohol, toluene, benzene, methylene chloride, chloroform, tetrahydrofuran, 1,4-dioxane, dimethylformamide, dimethylacetamide, N-methylpyrrolidinone, dimethyl sulfoxide, or mixed solvents thereof are suitable. The reaction temperature is usually −78° C. to 200° C., and preferably 0° C. to 50° C. The reaction time is usually 5 minutes to 3 days, and preferably 5 minutes to 10 hours.

Examples of the condensing agent and activating agent include diphenylphosphoric acid azide, N,N'-dicyclohexylcarbodiimide, benzotriazol-1-yloxytrisdimethylaminophosphonium salt, 4-(4,6-dimethoxy-1,3,5-triazin-2-yl)-4-methylmorpholinium chloride, 1-ethyl-3-(3-dimethylaminopropyl)carbodiimide, a combination of 1-ethyl-3-(3-dimethylaminopropyl)carbodiimide and 1-hydroxybenzotriazole, 2-chloro-1,3-dimethylimidazolinium chloride, O-(7-azabenzotriazo-1-yl)-N,N,N',N'-tetramethylhexauronium hexafluorophosphate, 1,1-carbonyldiimidazole, and N-hydroxysuccinic acid imide.

Furthermore, regarding the reaction described above, a base may be added thereto, if necessary. Examples of the base include organic bases such as triethylamine, diisopropylethylamine, pyridine, lutidine, collidine, 4-dimethylaminopyridine, potassium tert-butyrate, sodium tert-butyrate, sodium methoxide, sodium ethoxide, lithium hexamethyldisilazide, sodium hexamethyldisilazide, potassium hexamethyldisilazide, diazabicycloundecene, diazabicyclononene, and butyllithium; and inorganic bases such as sodium hydrogen carbonate, sodium carbonate, potassium carbonate, cesium carbonate, sodium hydroxide, and sodium hydride. The amount of addition thereof is 1 to 100 moles, and preferably 1 to 10 moles, with respect to 1 mole of the compound represented by general formula (VIII).

The compound represented by general formula (IX) that is obtainable as such is isolated and purified by known separation and purification means, for example, concentration, concentration under reduced pressure, crystallization, solvent extraction, reprecipitation, and chromatography, or can be used in the production of the compound (I) of the present invention without being isolated and purified.

Production Method 3

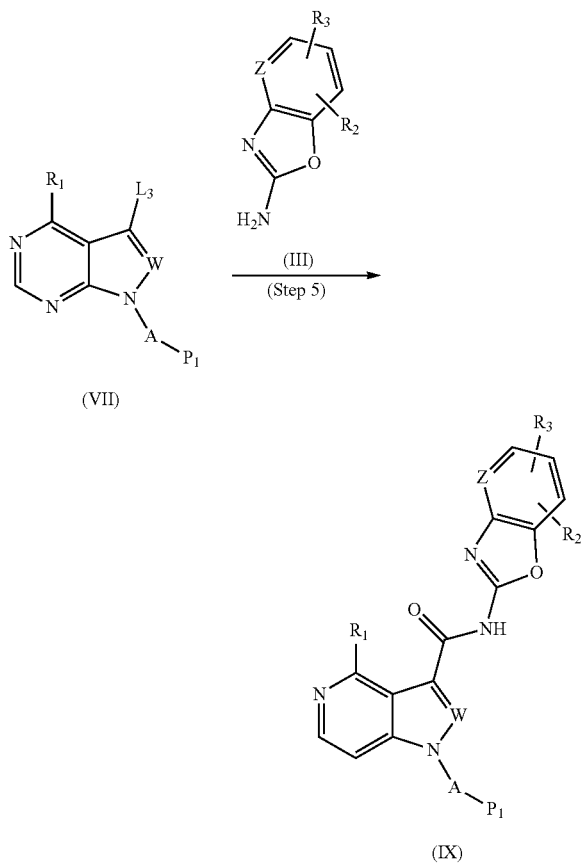

wherein $L_3$ represents a leaving group; and W, A, Y, Z, $P_1$, $R_1$, $R_2$ and $R_3$ respective have the same meanings as defined above.

(Step 5) The present step is a process for producing a compound represented by general formula (IX) by allowing the compound represented by general formula (VII) to react with, for example, a transition metal and optionally a base, in a carbon monoxide atmosphere in the presence of the compound (III), in a solvent which does not adversely affect the reaction.

In general formula (VII), the leaving group represented by $L_3$ is a bromine atom or an iodine atom, and a commercially available product may be used, or the relevant compound can be produced according to a known method.

In the present process, the pressure of carbon monoxide is 1 atmosphere to 10 atmospheres, and preferably 1 atmosphere to 5 atmospheres.

The transition metal catalyst that can be used in the present process is, for example, a palladium catalyst (for example, palladium acetate, tris(dibenzylideneacetone)dipalladium, bis(triphenylphosphine)palladium(II) dichloride, and 1,1'-bis(diphenylphosphino)ferrocene-palladium(II) dichloride-dichloromethane complex, and if necessary, a ligand (for example, triphenylphosphine, xantphos, or tri-tert-butylphosphine) is added thereto. The amount of use of the transition metal catalyst may vary with the kind of the catalyst; however, the amount of use is usually 0.0001 to 1 mole, and preferably 0.001 to 0.5 moles, with respect to 1 mole of the compound represented by general formula (IX). The amount of use of the ligand is usually 0.0001 to 4 moles, and preferably 0.01 to 2 moles, with respect to 1 mole of the compound represented by general formula (VII).

Furthermore, regarding the reaction described above, a base may be added thereto, if necessary. Examples of the base include organic bases such as triethylamine, diisopropylethylamine, pyridine, lutidine, collidine, 4-dimethylaminopyridine, N-methylmorpholine, potassium tert-butyrate, sodium tert-butyrate, sodium methoxide, sodium ethoxide, lithium hexamethyldisilazide, sodium hexamethyldisilazide, potassium hexamethyldisilazide, and butyllithium; and inorganic bases such as sodium hydrogen carbonate, sodium carbonate, potassium carbonate, cesium carbonate, sodium hydroxide, and sodium hydride. The amount of use of the base is usually 0.1 to 50 moles, and preferably 1 to 20 moles, with respect to 1 mole of the compound represented by general formula (VII).

The reaction solvent is not particularly limited as long as the reaction solvent does not interrupt the reaction, and examples thereof include hydrocarbons (for example, benzene, toluene, and xylene), nitriles (for example, acetonitrile), ethers (for example, dimethoxyethane, tetrahydrofuran, and 1,4-dioxane), alcohols (for example, methanol and ethanol), aprotic polar solvents (for example, dimethylformamide, dimethylacetamide, N-methylpyrrolidinone, dimethyl sulfoxide, and hexamethylphosphoramide), water, or mixtures thereof. The reaction time is 0.1 to 100 hours, and preferably 0.5 to 24 hours. The reaction temperature is 0° C. to a temperature at which the solvent boils, and preferably 0° C. to 150° C.

The compound represented by general formula (IX) that is obtainable as such is isolated and purified by known separation and purification means, for example, concentration, concentration under reduced pressure, crystallization, solvent extraction, reprecipitation, and chromatography, or can be used in the production of the compound (I) of the present invention without being isolated and purified.

Production Method 4

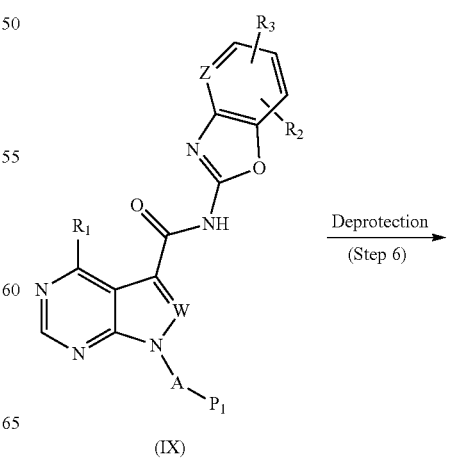

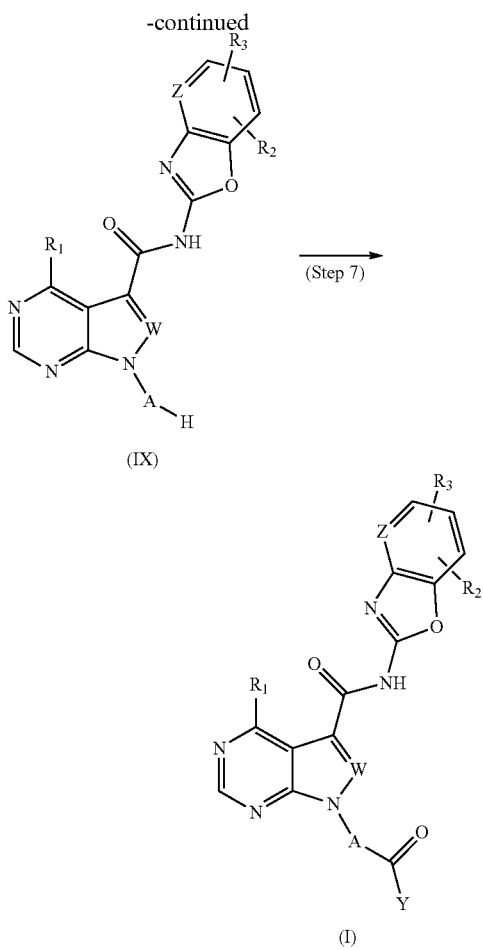

wherein $P_1$, A, X, Y, Z, $R_1$, $R_2$ and $R_3$ respectively have the same meanings as defined above.

(Step 6) The present step is a process for producing a compound represented by general formula (X) by deprotecting the amino group protection of the compound represented by general formula (IX). The method for deprotection can be carried out usually by a known method, for example, the method described in Protective Groups in Organic Synthesis, T. W. Greene, John Wiley & sons (1981), or a method equivalent thereto. An example of the protective group is tert-butyloxycarbonyl. In a case in which a tert-butyloxycarbonyl group is used as the protective group, deprotection under acidic conditions is preferred, and examples of the acid include hydrochloric acid, acetic acid, trifluoroacetic acid, sulfuric acid, methanesulfonic acid, and tosylic acid. Alternatively, deprotection using a Lewis acid is also preferred, and examples thereof include trimethylsilyliodine and a boron trifluoride-diethyl ether complex. The amount of use of the acid is preferably 1 to 100 moles with respect to 1 mole of the compound (IX).

The solvent used in the reaction may be any solvent as long as it does not adversely affect the reaction, and for example, alcohols (for example, methanol), hydrocarbons (for example, benzene, toluene, and xylene), halogenated hydrocarbons (for example, methylene chloride, chloroform, and 1,2-dichloroethane), nitriles (for example, acetonitrile), ethers (for example, dimethoxyethane and tetrahydrofuran), aprotic polar solvents (for example, N,N-dimethylformamide, dimethyl sulfoxide, and hexamethyl-phosphoramide), or mixtures thereof are used. The reaction time is 0.1 to 100 hours, and preferably 0.5 to 24 hours. The reaction temperature is 0° C. to 120° C., and preferably 0° C. to 90° C.

The compound represented by general formula (X) that is obtainable as such is isolated and purified by known separation and purification means, for example, concentration, concentration under reduced pressure, crystallization, solvent extraction, reprecipitation, and chromatography, or may be subjected to the subsequent process without being isolated and purified.

(Step 7) The present step is a process for producing the compound of the present invention represented by general formula (I), by an amidation reaction between the compound represented by general formula (X) and a carboxylic acid represented by Y—COOH or an acid halide represented by Y—C(=O)-L (wherein L represents a chlorine atom or a bromine atom).

When a carboxylic acid represented by Y—COOH is used as an amidation reagent, the amidation reaction is carried out using 0.5 to 10 moles, and preferably 1 to 3 moles, of the carboxylic acid with respect to 1 mole of the compound represented by general formula (X), in the presence of an appropriate condensing agent. Meanwhile, regarding the relevant carboxylic acid, a commercially available product may be used, or the carboxylic acid can be produced according to a known method.

The reaction solvent is not particularly limited as long as the reaction solvent does not interrupt the reaction, and for example, isopropanol, tert-butyl alcohol, toluene, benzene, methylene chloride, chloroform, tetrahydrofuran, 1,4-dioxane, dimethylformamide, dimethylacetamide, N-methylpyrrolidinone, dimethyl sulfoxide, or mixed solvents thereof are suitable. The reaction temperature is usually −78° C. to 200° C., and preferably 0° C. to 50° C. The reaction time is usually 5 minutes to 3 days, and preferably 5 minutes to 10 hours.

Examples of the condensing agent include diphenylphosphoric acid azide, N,N'-dicyclohexylcarbodiimide, benzotriazol-1-yloxytrisdimethylaminophosphonium salt, 4-(4,6-dimethoxy-1,3,5-triazin-2-yl)-4-methylmorpholinium chloride, 1-ethyl-3-(3-dimethylaminopropyl)carbodiimide, a combination of 1-ethyl-3-(3-dimethylaminopropyl)carbodiimide and 1-hydroxybenzotriazole, 2-chloro-1,3-dimethylimidazolinium chloride, and O-(7-azabenzotriazo-1-yl)-N,N,N',N'-tetramethylhexauronium hexafluorophosphate.

Furthermore, regarding the reaction, a base can be added thereto, if necessary. Examples of the base include organic bases such as triethylamine, diisopropylethylamine, pyridine, lutidine, collidine, 4-dimethylaminopyridine, potassium tert-butyrate, sodium tert-butyrate, sodium methoxide, sodium ethoxide, lithium hexamethyldisilazide, sodium hexamethyldisilazide, potassium hexamethyldisilazide, and butyllithium; and inorganic bases such as sodium hydrogen carbonate, sodium carbonate, potassium carbonate, cesium carbonate, sodium hydroxide, and sodium hydride. The amount of addition thereof is 1 to 100 moles, and preferably 1 to 10 moles, with respect to 1 mole of the compound represented by general formula (X).

When an acid halide represented by Y—C(=O)-L (wherein L represents a chlorine atom or a bromine atom) is used as the amidation reagent, the reaction is carried out using 0.5 to 5 moles, and preferably 0.9 to 1.1 moles, of the acid halide with respect to 1 mole of the compound represented by general formula (X). Meanwhile, regarding the relevant acid halide, a commercially available product may be used, or the acid halide can be produced according to a known method.

The reaction solvent is not particularly limited as long as the reaction solvent does not interrupt the reaction, and for example, water, toluene, benzene, methylene chloride, chloroform, tetrahydrofuran, acetonitrile, 1,4-dioxane, dimethylformamide, dimethylacetamide, N-methylpyrrolidinone, or mixed solvents thereof are suitable. The reaction temperature is usually −78° C. to 200° C., and preferably −20° C. to 50° C. The reaction time is usually 5 minutes to 3 days, and preferably 5 minutes to 10 hours.

Furthermore, regarding the reaction described above, a base can be added thereto, if necessary. Examples of the base include organic bases such as triethylamine, diisopropylethylamine, pyridine, lutidine, collidine, 4-dimethylaminopyridine, potassium tert-butyrate, sodium tert-butyrate, sodium methoxide, sodium ethoxide, lithium hexamethyldisilazide, sodium hexamethyldisilazide, potassium hexamethyldisilazide, and butyllithium; and inorganic bases such as sodium hydrogen carbonate, sodium carbonate, potassium carbonate, cesium carbonate, sodium hydroxide, and sodium hydride. Regarding the amount of addition, the base can be used in an amount of 1 to 100 moles, and preferably 1 to 10 moles, with respect to 1 mole of the compound represented by general formula (X).

The compound represented by general formula (I) that is obtainable as such can be isolated and purified by known separation and purification means, for example, concentration, concentration under reduced pressure, crystallization, solvent extraction, reprecipitation, and chromatography.

Production Method 5

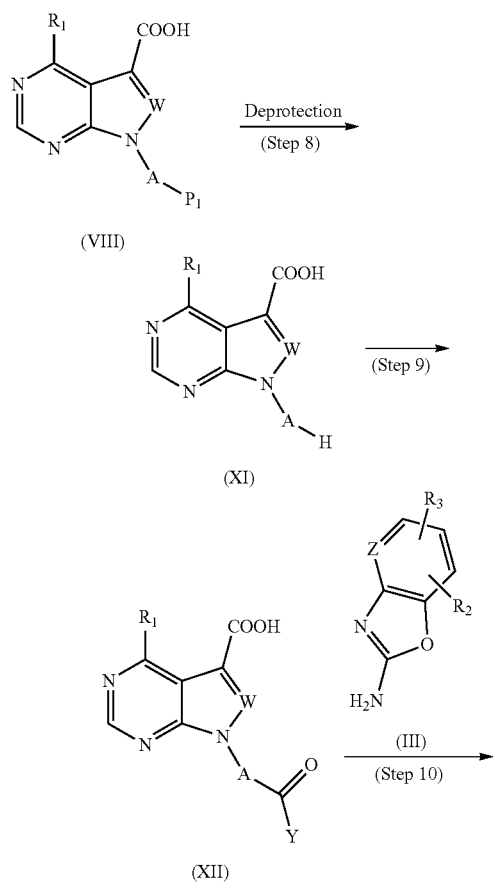

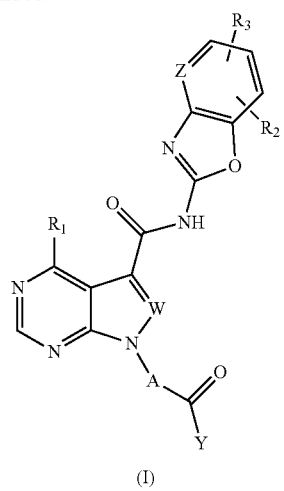

wherein $P_1$, W, A, Y, Z, $R_1$, $R_2$ and $R_3$ respectively have the same meanings as defined above.

(Step 8 and Step 9)

The present steps are processes for producing a compound represented by general formula (XII) by subjecting the compound represented by general formula (VIII) to procedures similar to Production Method 4, Steps 6 and 7.

(Step 10) The present step is a process for producing the compound represented by general formula (I) by subjecting the compound represented by general formula (XII) to procedures similar to Production Method 2, Step 4.

The compound represented by general formula (I) that is obtainable as such can be isolated and purified by known separation and purification means, for example, concentration, concentration under reduced pressure, crystallization, solvent extraction, reprecipitation, and chromatography.

Production Method 6

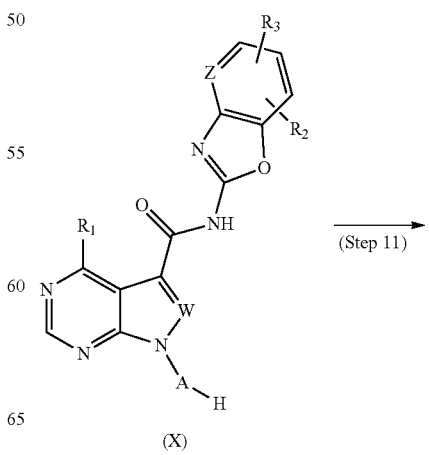

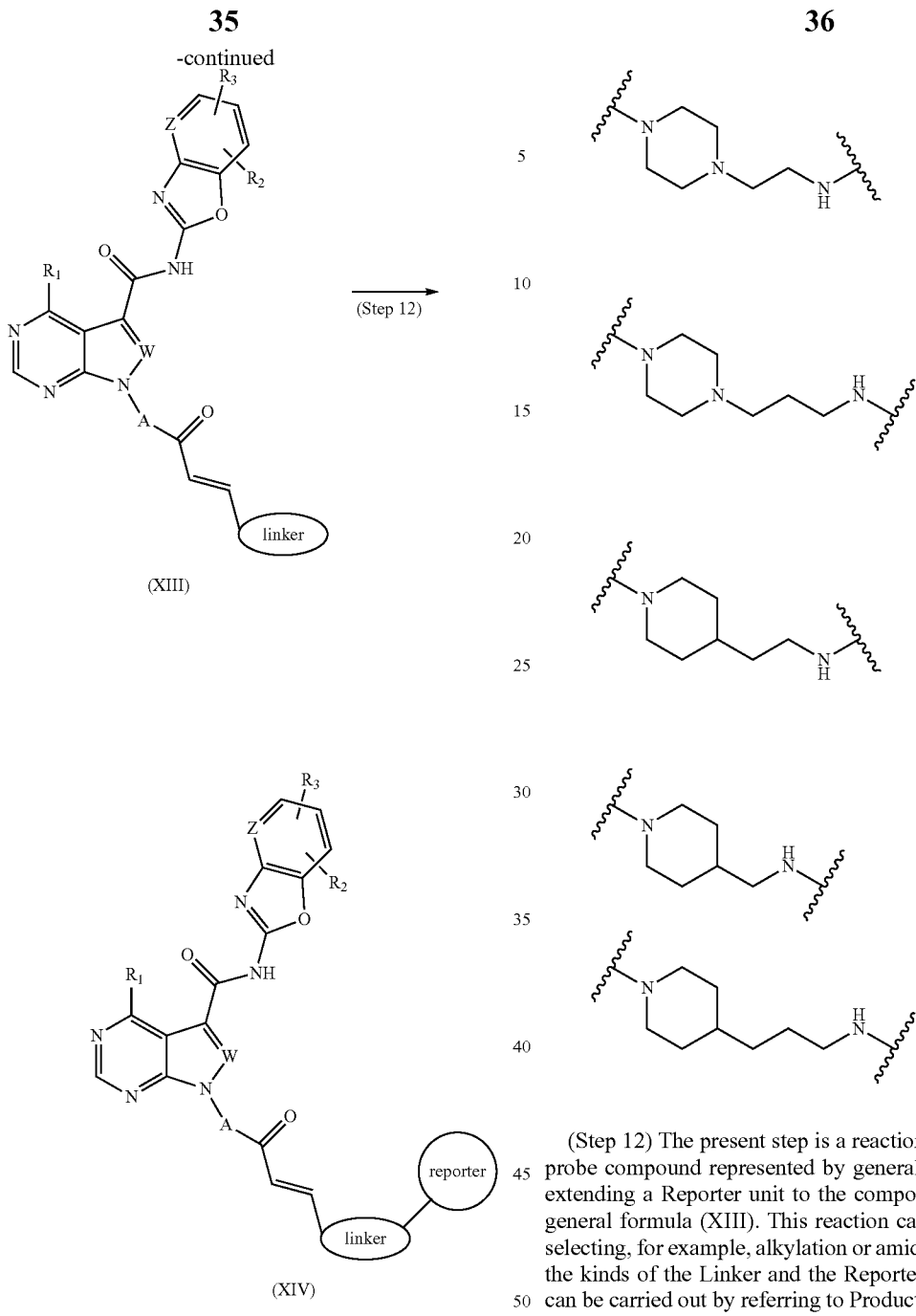

wherein W, A, Z, $R_1$, $R_2$ and $R_3$ respectively have the same meanings as defined above.

(Step 11) The present step is a process for producing a compound represented by general formula (XIII) through an amidation reaction between the compound represented by general formula (X) and a carboxylic acid represented by "Linker-CH=CH—COOH" or an acid halide represented by "Linker-CH=CH—CO-L" (wherein L represents a chlorine atom or a bromine atom). This reaction can be carried out by referring to Production Method 4, Step 7.

It is desirable that the linker unit contains, at the part for connecting the Reporter unit and the compound, a functional group which has an appropriate length and properties that do not significantly affect the profiles of the compound, and is capable of extending the Reporter unit. Examples of the Linker unit include:

(Step 12) The present step is a reaction for synthesizing a probe compound represented by general formula (XIV) by extending a Reporter unit to the compound represented by general formula (XIII). This reaction can be carried out by selecting, for example, alkylation or amidation depending on the kinds of the Linker and the Reporter, and the reactions can be carried out by referring to Production Method 2, Step 2 and Production Method 4, Step 7, respectively.

The Reporter unit is a site intended to facilitate detection of the binding state with BTK using biochemical techniques (for example, luminescence and fluorescence), by co-treating a probe compound containing the Reporter unit with, for example, a specimen in the blood or in the spleen, or by co-treating the probe compound with a cell extract derived from, for example, the blood or the spleen. It is desirable that the Reporter unit contains a functional group that can be connected to the Linker unit, for example, alkylation or amidation as described above. Regarding the Reporter unit, for example, BODIPY (registered trademark) FL, BODIPY (registered trademark) R6G, BODIPY (registered trademark) TMR, BODIPY (registered trademark) 581/591, and BODIPY (registered trademark) TR are employed as luminophores, and for example, biotin is employed as a binding group.

Production Method 7

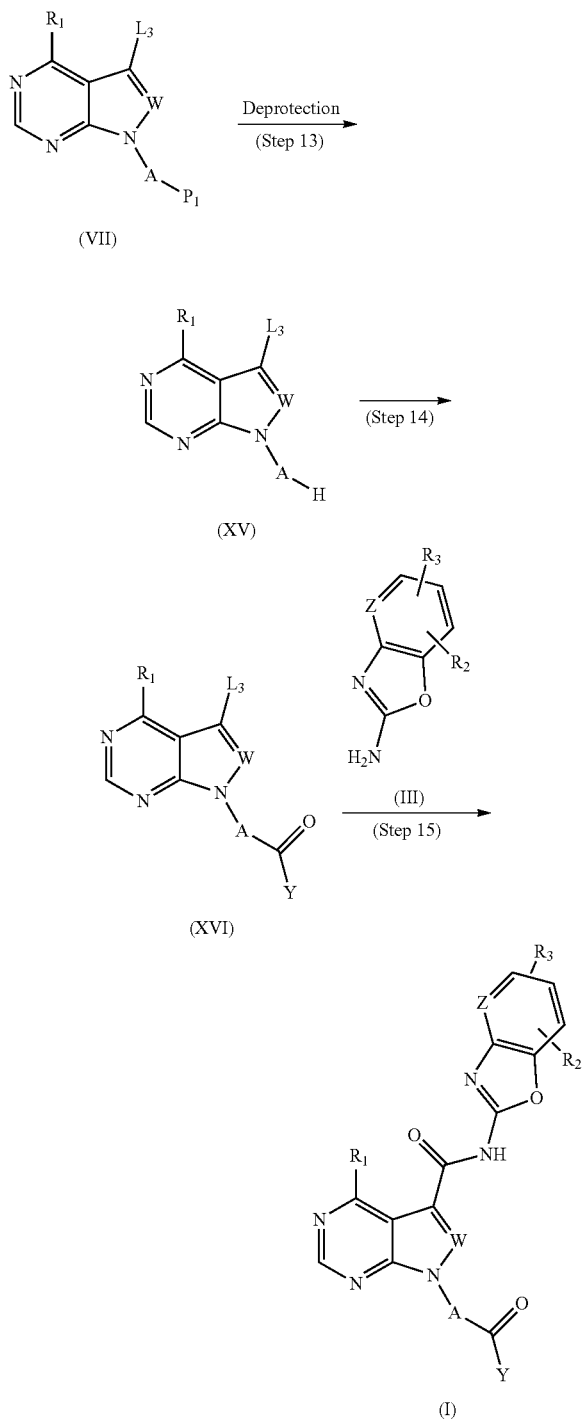

wherein $L_3$ represents a leaving group; and $P_1$, W, A, Y, Z, $R_1$, $R_2$ and $R_3$ respectively have the same meanings as defined above.

(Steps 13 and 14)

The present steps are processes for producing a represented by general formula (XV) by subjecting the compound represented by general formula (VII) to procedures similar to Production Method 4, Steps 6 and 7.

(Step 15)

The present step is a process for producing the compound of general formula (I) by subjecting a compound represented by general formula (XVI) to procedures similar to Production Method 3, Step 5.

The compound represented by general formula (I) that is obtainable as such can be isolated and purified by known separation and purification means, for example, concentration, concentration under reduced pressure, crystallization, solvent extraction, reprecipitation, and chromatography.

In regard to the Production Methods 1 to 7, for an amino group, an imino group, a hydroxyl group, a carboxyl group, a carbonyl group, an amide group, and a functional group having an active proton, such as indole, a protected reagent may be used in appropriate steps in the various production methods, or a protective group may be introduced to the relevant functional group according to a conventional method, and then the protective group may be removed.

The "protective group for an amino group or an imino group" is not particularly limited as long as the group has its function, and examples thereof include, for example, aralkyl groups such as a benzyl group, a p-methoxybenzyl group, a 3,4-dimethoxybenzyl group, an o-nitrobenzyl group, a p-nitrobenzyl group, a benzhydryl group, a trityl group, and a coumyl group; for example, lower alkanoyl groups such as a formyl group, an acetyl group, a propionyl group, a butyryl group, a pivaloyl group, a trifuloroacetyl group, and a trichioroacetyl group; for example, a benzoyl group; for example, arylalkanoyl groups such as a phenylacetyl group and a phenoxyacetyl group; for example, lower alkoxycarbonyl groups such as a methoxycarbonyl group, an ethoxycarbonyl group, a propyloxycarbonyl group, and a tert-butoxycarbonyl group; for example, aralkyloxycarbonyl groups such as a p-nitrobenzyloxycarbonyl group and a phenethyloxycarbonyl group; for example, lower alkylsilyl groups such as a trimethylsilyl group and a tert-butyldimethylsilyl group; for example, a tetrahydropyranyl group; for example, a trimethylsilylethoxymethyl group; for example, lower alkylsulfonyl groups such as a methylsulfonyl group, an ethylsulfonyl group, and a tert-butylsulfonyl group; for example, lower alkylsulfinyl groups such as a tert-butylsulfinyl group; for example, arylsulfonyl groups such as a benzenesulfonyl group and a toluenesulfonyl group; and for example, imide groups such as a phthalimide group. Particularly, a trifluoroacetyl group, an acetyl group, a tert-butoxycarbonyl group, a benzyloxycarbonyl group, a trimethylsilylethoxymethyl group, and a coumyl group are preferred.

The "protective group for a hydroxyl group" is not particularly limited as long as the protective group has its function, and examples thereof include lower alkyl groups such as a methyl group, an ethyl group, a propyl group, an isopropyl group, and a tert-butyl group; for example, lower alkylsilyl groups such as a trimethylsilyl group and a tert-butyldimethylsilyl group; for example, lower alkoxymethyl groups such as a methoxymethyl group and a 2-methoxyethoxymethyl group; for example, a tetrahydropyranyl group; for example, a trimethylsilylethoxymethyl group; for example, aralkyl groups such as a benzyl group, a p-methoxybenzyl group, a 2,3-dimethoxybenzyl group, an o-nitrobenzyl group, a p-nitrobezyl group, and a trityl group; and for example, acyl groups such as a formyl group, an acetyl group, and a trifluoroacetyl group. Particularly, for example, a methyl group, a methoxymethyl group, a tetrahydropyranyl group, a trimethylsilylethoxymethyl group, a tert-butyldimethylsilyl group, and an acetyl group are preferred.

The "protective group for a carboxyl group" is not particularly limited as long as the protective group has its function, and examples thereof include lower alkyl groups such as a methyl group, an ethyl group, a propyl group, an isopropyl group, and a tert-butyl group; for example, halolower alkyl groups such as a 2,2,2-trichloroethyl group; for example, lower alkenyl groups such as an allyl group; for example, a trimethylsilylethoxymethyl group; and for example, aralkyl groups such as a benzyl group, a p-methoxybenzyl group, a p-nitrobenzyl group, a benzhydryl group, and a trityl group. Particularly, for example, a methyl group, an ethyl group, a tert-butyl group, an allyl group, a benzyl group, a p-methoxybenzyl group, and a trimethylsilylethoxymethyl group are preferred.

The "protective group for a carbonyl group" is not particularly limited as long as the protective group has its function, and examples thereof include ketals and acetals such as ethylene ketal, trimethylene ketal, dimethyl ketal, ethylene acetal, trimethylene acetal, and dimethyl acetal.

The method for removing a protective group may vary depending on the kind of the relevant protective group and stability of the target compound. However, for example, the removal of a protective group is carried out according to methods described in the Document (see Protective Groups in Organic Synthesis, 3$^{rd}$ Ed., written by T. W. Greene, John Wiley & Sons, 1999) or methods equivalent thereto, for example, by a method of performing solvolysis using an acid or a base, that is, for example, bringing 0.01 mol to a large excess of an acid, preferably trifluoroacetic acid, formic acid or hydrochloric acid; or an equal mol to a large excess of a base, preferably potassium hydroxide or calcium hydroxide, into effect; or by chemical reduction using, for example, a metal hydride complex, or by catalytic reduction using, for example, a palladium-carbon catalyst or a Raney nickel catalyst.

The compound of the present invention can be easily isolated and purified by conventional separation means. Examples of such means include solvent extraction, recrystallization, reverse phase high performance liquid chromatography for fractionation, column chromatography, and thin layer chromatography for fractionation.

In a case in which the compound of the present invention has isomers such as optical isomers, stereoisomers, regioisomers and rotamers, mixtures of any isomers are all included in the compound of the present invention. For example, when the compound of the present invention has optical isomers, optical isomers resolved from racemates are also included in the compound of the present invention. These isomers can be each obtained as single compounds by synthesis techniques that are known per se and separation techniques (for example, concentration, solvent extraction, column chromatography, and recrystallization).

The compound of the present invention or a salt thereof may be crystalline, and irrespective of whether the crystal form is a single form or a polymorphic mixture, the crystals are also included in the compound of the present or a salt thereof. A crystal can be produced by applying a crystallization method that is known per se, and performing crystallization. The compound of the present invention or a salt thereof may be a solvate (for example, hydrate) or may be a non-solvate, which are both included in the compound of the present invention or a salt thereof. Compounds labeled with isotopes (for example, $^3$H, $^{14}$C, $^{35}$S, and $^{125}$I) are also included in the compound of the present invention or a salt thereof.

A prodrug of the compound of the present invention or a salt thereof refers to a compound which converts to the compound of the present invention or a salt thereof as a result of a reaction caused by an enzyme or gastric acid in the living body under physiological conditions, that is, a compound which enzymatically causes, for example, oxidation, reduction or hydrolysis and converts to the compound of the present invention or a salt thereof, or a compound which causes, for example, hydrolysis by means of gastric acid and converts to the compound of the present invention or a salt thereof. Furthermore, the prodrug of the compound of the present invention or a salt thereof may also be a compound which converts to the compound of the present invention or a salt thereof under the physiological conditions described in Hirokawa Shoten Annual of 1990 "Iyakuhin no Kaihatsu (Development of Pharmaceutical Products)", Vol. 7, Molecule Design, pp. 163-198.

A salt of the compound of the present invention means a salt that is conventionally used in the field of organic chemistry, and examples thereof include salts such as a base addition salt associated with a carboxyl group in a case in which the compound of the present invention has the relevant carboxyl group; and an acid addition salt associated with an amino group or a basic heterocyclic group in a case in which the compound of the present invention has the relevant amino group or basic heterocyclic group.

Examples of the base addition salt include, for example, alkali metal salts such as sodium salt and potassium salt; for example, alkaline earth metal salts such as calcium salt and magnesium salt; for example, ammonium salt; and for example, organic amine salts such as trimethylamine salt, triethylamine salt, dicyclohexylamine salt, ethanolamine salt, diethanolamine salt, triethanolamine salt, procaine salt, and N,N'-dibenzylethylenediamine salt.

Examples of the acid addition salt include, for example, inorganic acid salts such as hydrochloride, sulfate, nitrate, phosphate, and perchlorate; for example, organic acid salts such as acetate, formate, maleate, tartrate, citrate, ascorbate, and trifluoroacetate; and for example, sulfonic acid salts such as methanesulfonate, isetionate, benzenesulfonate, and p-toluenesulfonate.

The compound of the present invention or a salt thereof has excellent BTK inhibitory activity, and is useful as an antitumor agent. Furthermore, the compound or a salt thereof has excellent selectivity to BTK, and has an advantage of having reduced adverse side effects that are caused by inhibiting other kinases as well.

The compound of the present invention or a salt thereof has excellent BTK inhibitory activity. "BTK" according to the present specification includes human or non-human mammalian BTK's, and the BTK is preferably human BTK. Also, the term "BTK" includes isoforms.

Furthermore, due to its excellent BTK inhibitory activity, the compound of the present invention or a salt thereof is useful as a medicine for the prevention or treatment of diseases associated with BTK. The "diseases associated with BTK" include diseases that undergo a decrease in the incidence rate and remission, alleviation and/or complete recovery of symptoms, as a result of deletion, suppression and/or inhibition of the functions of BTK. Examples of such diseases include cancers and tumors, but the diseases are not intended to be limited to these. There are no particular limitations on the object cancers and tumors, and examples thereof include epithelial cancers (for example, respiratory system cancers, gastrointestinal system cancers, reproductive system cancers, and secretion system cancers), sarcomas, hematopoietic system tumors, central nervous system tumors, and peripheral nerve tumors. Preferred examples are hematopoietic system tumors (for example, leukemia, multiple myeloma, and malignant lymphoma). Furthermore, there are no particular limitations on the kind of the organs of tumor development, and examples thereof include head and neck carcinoma, esophageal cancer, stomach cancer, colon cancer, rectal cancer, liver cancer, gall bladder/bile duct cancer, biliary tract cancer, pancreatic cancer, lung cancer, breast cancer, ovarian cancer, cervical cancer, uterine cancer, kidney cancer, urinary bladder cancer, prostate cancer, testicular tumor, bone/soft tissue sarcoma, hematologic tumor, multiple myeloma, skin cancer, brain tumor, and mesothelial cancer. Preferred examples of the hematopoietic system tumors include acute leukemia, acute promyelocytic leukemia, acute lymphoblastic leukemia, chronic myelogenous leukemia, lymphoblastic lymphoma, myeloproliferative neoplasms, chronic lymphocytic leukemia, small lymphocytic lymphoma, myelodysplastic syndromes, follicular lymphoma, MALT lymphoma, marginal zone lymphoma, lymphoplasmacytic lymphoma, Waldenstroem macroglobulinemia, mantle cell lymphoma, diffuse large B-cell lymphoma, Burkitt's lymphoma, extranodal NK/T-cell lymphoma, Hodgkin's lymphoma, and multiple myeloma. Particularly preferred examples include hematologic tumors such as B-lymphoblastic leukemia/lymphoma, follicular lymphoma, mantle cell lymphoma, nodal follicular marginal zone lymphoma, diffuse large B-cell lymphoma, Burkitt's lymphoma, chronic lymphocytic leukemia, small lymphocytic lymphoma, Waldenstroem macroglobulinemia, extranodal NK/T-cell lymphoma, Hodgkin's lymphoma, myelodysplastic syndromes, acute myelogenous leukemia, and acute lymphocytic leukemia.

On the occasion of using the compound of the present invention or a salt thereof as a medicine, various dosage forms can be employed according to the purpose of prevention or treatment by incorporating pharmaceutical carriers as necessary. The dosage form may be, for example, any of an oral preparation, an injectable preparation, a suppository preparation, an ointment, and a patch. These dosage forms can be respectively produced by formulation methods that are conventionally used and known to those skilled in the art.

Regarding the pharmaceutical carriers, various organic or inorganic carrier materials that are conventionally used as formulation materials are used, and the pharmaceutical carriers are incorporated as, for example, an excipient, a binder, a disintegrant, a lubricant, and a coating agent in solid preparations; and as a solvent, a dissolution aid, a suspending agent, an isotonic agent, a pH adjusting agent, a buffering agent, and an analgesic agent in liquid preparations. Furthermore, if necessary, formulation additives such as an antiseptic, an antioxidant, a colorant, a flavoring/savoring agent, and a stabilizer can also be used.

Examples of the excipient include lactose, sucrose, D-mannitol, starch, crystalline cellulose, and calcium silicate.

Examples of the binder include hydroxypropyl cellulose, methyl cellulose, polyvinylpyrrolidone, sugar powder, and hypromellose.

Examples of the disintegrant include sodium starch glycolate, carmellose calcium, croscarmellose sodium, crospovidone, low-substituted hydroxypropyl cellulose, and partially gelatinized starch.

Examples of the lubricant include talc, magnesium stearate, sucrose fatty acid esters, stearic acid, and sodium stearyl fumarate.

Examples of the coating agent include ethyl cellulose, aminoalkyl methacrylate copolymer RS, hypromellose, and sucrose.

Examples of the solvent include water, propylene glycol, and physiological saline.

Examples of the dissolution aid include polyethylene glycol, ethanol, α-cyclodextrin, Macrogol 400, and Polysorbate 80.

Examples of the suspending agent include carrageenan, crystalline cellulose, carmellose sodium, and polyoxyethylene hardened castor oil.

Examples of the isotonic agent include sodium chloride, glycerin, and potassium chloride.

Examples of the pH adjusting agent and the buffering agent include sodium citrate, hydrochloric acid, lactic acid, phosphoric acid, and sodium dihydrogen phosphate.

Examples of the analgesic agent include procaine hydrochloride and lidocaine.

Examples of the antiseptic agent include ethyl paraoxybenzoate, cresol, and benzalkonium chloride.

Examples of the antioxidant include sodium sulfite, ascorbic acid, and natural vitamin E.

Examples of the colorant include titanium oxide, iron sesquioxide, Edible Blue No. 1, and copper chlorophyll.

Examples of the flavoring/savoring agent include aspartame, saccharin, sucralose, 1-menthol, and mint flavor.

Examples of the stabilizer include sodium pyrosulfite, sodium edetate, erythorbic acid, magnesium oxide, and dibutylhydroxytoluene.

In the case of preparing an oral solid preparation, an excipient, optionally an excipient, a binder, a disintegrant, a lubricant, a colorant, and a flavoring/savoring agent are added to the compound of the present invention, and then for example, a tablet, a coated tablet, a granular preparation, a powder preparation, and a capsule preparation can be produced by conventional methods.

In the case of preparing an injectable preparation, a pH adjusting agent, a buffering agent, a stabilizer, an isotonic agent, and a local anesthetic are added to the compound of the present invention, and a subcutaneous, intramuscular, and intravenous injectable preparations can be produced by conventional methods.

The amounts of the compound of the present invention to be incorporated into the various unit dosage forms may vary depending on the symptoms of the patient to whom this compound should be applied, or depending on the formulation form; however, it is generally desirable to adjust the amount to 0.05 to 1000 mg in an oral preparation, to 0.01 to 500 mg in an injectable preparation, and to 1 to 1000 mg in a suppository preparation, per unit dosage form.

Furthermore, the amount of administration per day of a medicament having the dosage form described above may vary with for example, the symptoms, body weight, age and gender of the patient, and cannot be determined indiscriminately. However, the amount of administration may be used usually in an amount of 0.05 to 5000 mg, and preferably 0.1 to 1000 mg, per day for an adult (body weight: 50 kg), and it is preferable to administer this once a day, or in divided portions in about 2 to 3 times.

EXAMPLES

Hereinafter, the present invention will be described more specifically by way of Examples, but the present invention is not intended to be limited to these.

Regarding the various reagents used in the Examples, unless particularly stated otherwise, commercially available products were used. For silica gel column chromatography, a PURIF-PACK (registered trademark) SI manufactured by Schott Moritex Corp., a KP-Sil (registered trademark) Silica Prepacked Column manufactured by Biotage AB, or a HP-Sil (registered trademark) Silica Prepacked Column manufactured by Biotage AB was used. For basic silica gel column chromatography, a PURIF-PACK (registered trademark) NH manufactured by Moritex Corp., or a KP-NH (registered trademark) Prepacked Column manufactured by Biotage AB was used. For thin layer chromatography for fractionation, a KIESELGEL TM60F254, Art. 5744 manufactured by Merck KGaA, or a NH2 silica gel 60F254 plate manufactured by Wako Pure Chemical Industries, Ltd. was used. The NMR spectrum was measured using an AL400 (400 MHz; JEOL, Ltd.), a MERCURY400 (400 MHz; Agilent Technologies, Inc.) type spectrometer, or an INOVA400 (400 MHz; Agilent Technologies, Inc.) equipped with an OMNMR probe (Protasis Corp.) type spectrometer, and using tetramethylsilane as the internal reference in a case in which the deuterated solvent contains tetramethylsilane, while in other cases, using an NMR solvent as the internal reference. All the δ values were expressed in ppm. The microwave reaction was carried out using a DISCOVER S class manufactured by CEM Corp.

The LCMS spectrum was measured using an ACQUITY SQD (quadrupole type) manufactured by Waters Corp. under the conditions described below.

Column: YMC-TRIART C18 manufactured by YMC Co., Ltd., 2.0×50 mm, 1.9
MS detection: ESI positive
UV detection: 254 nm and 210 nm
Column flow rate: 0.5 mL/min
Mobile phase: Water/acetonitrile (0.1% formic acid)
Amount of injection: 1 μL

TABLE 1

| Gradient | | |
| --- | --- | --- |
| Time (min) | Water | Acetonitrile |
| 0 | 95 | 5 |
| 0.1 | 95 | 5 |
| 2.1 | 5 | 95 |
| 3.0 | STOP | |

Furthermore, reverse phase preparative HPLC purification was carried out using a preparative system manufactured by Waters Corp. under the conditions described below.

Column: A YMC-ACTUS TRIART C18 manufactured by YMC Co., Ltd., 20×50 mm, 5 μm, connected with a YMC-ACTUS TRIART C18 manufactured by YMC Co., Ltd. 20×10 mm, 5 μm, was used.
UV detection: 254 nm
MS detection: ESI positive
Column flow rate: 25 mL/min
Mobile phase: Water/acetonitrile (0.1% formic acid)
Amount of injection: 0.1 to 0.5 mL
The meanings of abbreviations are shown below.
s: Singlet
d: Doublet
t: Triplet
q: Quartet
dd: Double doublet
dt: double triplet
td: Triple doublet
tt: Triple triplet
ddd: Double double doublet
ddt: Double double triplet
dtd: Double triple doublet
tdd: Triplet double doublet
m: Multiplet
br: Broad
brs: Broad singlet
CDT: Carbonyldiimidazole
DMSO-$d_6$: Deuterated dimethyl sulfoxide
$CDCl_3$: Deuterated chloroform
$CD_3OD$: Deuterated methanol
THF: Tetrahydrofuran
DMF: N,N-dimethylformamide
DMA: N,N-dimethylacetamide
NMP: 1-Methyl-2-pyrrolidinone
DMSO: Dimethyl sulfoxide
TFA: Trifluoroacetic acid
WSC: 1-(3-Dimethylaminopropyl)-3-ethylcarbodiimide hydrochloride
HOBt: 1-Hydroxybenzotriazole monohydrate
HATU: (Dimethylamino)-N,N-dimethyl(3H-[1,2,3]triazolo[4,5-b]pyridin-3-yloxy)methaneiminium hexafluorophosphate
DIAD: Diisopropyl azodicarboxylate
TBAF: Tetrabutylammonium fluoride
DIPEA: Diisopropylethylamine
$Boc_2O$: Di-tert-butyl dicarbonate
DMAP: Dimethylaminopyridine Synthetic Example 1

Synthesis of (R)-tert-butyl 3-(4-amino-3-iodo-1H-pyrazolo[3,4-d]pyrimidin-1-yl)piperidine-1-carboxylate

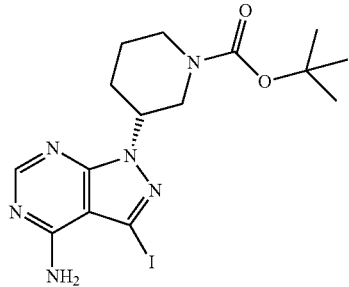

(Step 1) Synthesis of (S)-tert-butyl 3-(methylsulfonyloxy)piperidine-1-carboxylate 20 g of (S)—N-Boc-3-pyridinol was dissolved in 100 ml of toluene, and 21 ml of triethylamine and 9.2 ml of methanesulfonyl chloride were added thereto at 0° C. The mixture was stirred for 1 hour under ice cooling, subsequently ethyl acetate and water were added thereto, and an organic layer was separated. The organic layer was washed with a saturated aqueous solution of sodium hydrogen carbonate, a saturated aqueous solution of ammonium chloride and water, and then was dried over anhydrous sodium sulfate. The solvent was distilled off under reduced pressure, and thus 26.8 g of the title compound was obtained as a colorless solid.

(Step 2) Synthesis of (R)-tert-butyl 3-(4-amino-3-iodo-1H-pyrazolo[3,4-d]pyrimidin-1-yl)piperidine-1-carboxylate A suspension solution of 14.6 g of 3-iodo-1H-pyrazolo[3,4-d]pyrimidin-4-amine synthesized by the method described in WO 2007/126841, 25 g of (S)-tert-butyl 3-(methylsulfonyloxy)piperidine-1-carboxylate obtained in Step 1, and 69 g of potassium carbonate in 150 ml of DMA was heated to 100° C., and was stirred for 10 hours. The suspension solution was cooled to room temperature, and then 300 ml of water was added thereto. A solid thus obtained was collected by filtration and washed with water, and the solid was dried. Thus, 26.9 g of the title compound was obtained as a yellow solid. Physical property value: m/z [M+H]$^+$ 446.2

Synthetic Example 2

Synthesis of (R)-4-amino-1-(1-(tert-butyloxycarbonyl)piperidin-3-yl)-1H-pyrazolo[3,4-d]pyrimidine-3-carboxylic acid

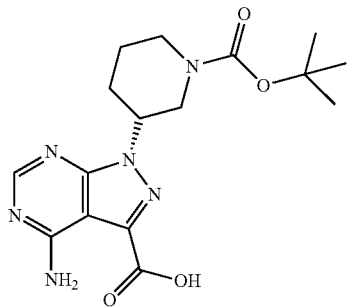

2 g of (R)-tert-butyl 3-(4-amino-3-iodo-1H-pyrazolo[3,4-d]pyrimidin-1-yl)piperidine-1-carboxylate obtained in Synthetic Example 1, 3 ml of 2-diethylaminoethanol, and 158 mg of Pd(PPh$_3$)$_2$Cl$_2$ were dissolved in 20 ml of NMP. After the system was purged with carbon monoxide, and then the solution was heated to 120° C. After the solution was stirred for 1 hour, the solution was cooled to room temperature. 10 ml of methanol was added thereto, and then 6 ml of a 5 N aqueous solution of sodium hydroxide was added thereto. The mixture was stirred for 10 minutes. Water was added thereto, and then the aqueous layer was washed with ethyl acetate. The aqueous layer was adjusted to pH 4 with hydrochloric acid, and a solid thus precipitated was collected by filtration, washed with water, and then dried. Thus, 1.26 g of the title compound was obtained as a pale yellow solid. Physical property value: m/z [M+H]$^+$ 363.1

Synthetic Example 3

Synthesis of (R)-4-amino-1-(1-(tert-butyloxycarbonyl)pyrrolidin-3-yl)-1H-pyrazolo[3,4-d]pyrimidine-3-carboxylic acid

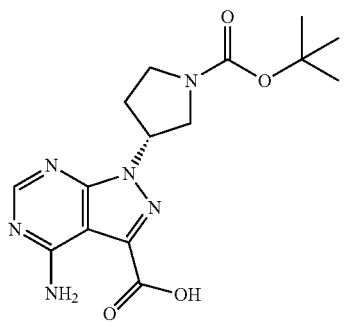 [SMILES: CC(C)(C)OC(=O)N1CC[C@@H](n2nc(C(=O)O)c3c(N)ncnc32)C1]

(Step 1) Synthesis of (S)-tert-butyl 3-(methylsulfonyloxy)pyrrolidine-1-carboxylate 935 mg of (S)-(−)-N-Boc-3-pyrrolidinol was dissolved in 15 ml of chloroform, and 1.04 ml of triethylamine and 467 µl of methanesulfonyl chloride were added thereto under ice cooling. The mixture was stirred for 1.5 hours at room temperature, subsequently ethyl acetate and water were added thereto, and an organic layer was separated. The organic layer was washed with a saturated aqueous solution of sodium hydrogen carbonate, a saturated aqueous solution of ammonium chloride, and water, and then was dried over anhydrous sodium sulfate. The solvent was distilled off under reduced pressure, and thus 1.3 g of the title compound was obtained as a colorless oily substance. Physical property value: m/z [M+H]$^+$ 266.1

(Step 2) Synthesis of (R)-tert-butyl 3-(4-amino-3-iodo-1H-pyrazolo[3,4-d]pyrimidin-1-yl)pyrrolidine-1-carboxylate A suspension of 20.0 g of 3-iodo-1H-pyrazolo[3,4-d]pyrimidin-4-amine synthesized by the method described in WO 2007/126841, 23 g of (S)-tert-butyl 3-(methylsulfonyloxy)pyrrolidine-1-carboxylate obtained in Step 1, and 32 g of potassium carbonate in 200 ml of DMA, was heated to 85° C., and was stirred for 3 hours. The solution was cooled to room temperature, and then a solid obtained by adding 400 ml of water thereto was collected by filtration, washed with water, and then dried. Thus, 23.5 g of the title compound was obtained as a pale yellow solid. Physical property value: m/z [M+H]$^+$ 431.0

(Step 3) Synthesis of (R)-4-amino-1-(1-(tert-butyloxycarbonyl)pyrrolidin-3-yl)-1H-pyrazolo[3,4-d]pyrimidine-3-carboxylic acid 2.0 g of (R)-tert-butyl 3-(4-amino-3-iodo-1H-pyrazolo[3,4-d]pyrimidin-1-yl)pyrrolidine-1-carboxylate obtained in the above Step 2, 3.1 ml of 2-diethylaminoethanol, and 163 mg of Pd(PPh$_3$)$_2$Cl$_2$ were dissolved in 20 ml of NMP. The system was purged with carbon monoxide, and then was heated to 120° C. After the solution was stirred for 1 hour, the solution was cooled to room temperature, and 10 ml of methanol was added thereto. Subsequently, 6 ml of a 5 N aqueous solution of sodium hydroxide was added thereto, and the mixture was stirred for 10 minutes. Water was added thereto, subsequently the aqueous layer was washed with chloroform, and the aqueous layer was adjusted to pH 4 with hydrochloric acid. A solid thus precipitated was collected by filtration, washed with water, and then dried. Thus, 1.35 g of the title compound was obtained as a pale yellow solid. Physical property value: m/z [M+H]$^+$ 349.1

Synthetic Example 4

Synthesis of 5-cyanobenzo[d]oxazol-2-amine

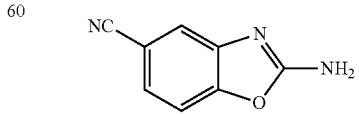

15.1 g of 3-amino-4-hydroxybenzonitrile was dissolved in 75 ml of ethanol and 75 ml of water, and 14.7 g of bromocyan was added in small portions to the solution under ice cooling. The mixture was stirred for 2 hours at room temperature, and was ice-cooled again. 112 ml of a 2 N aqueous solution of NaOH was added to the solution, and the mixture was stirred for another 30 minutes. Most of ethanol was roughly removed using an evaporator, and the residue was collected by filtration. The filter cake was washed with water, and thus 12.12 g of the title compound was obtained. Physical property value: m/z [M+H]$^+$ 161.1

Example 1

Synthesis of (R)-1-(1-acryloylpiperidin-3-yl)-4-amino-N-(5-chlorobenzo[d]oxazol-2-yl)-1H-pyrazolo[3,4-d]pyrimidine-3-carboxamide (Example Compound 1)

(Step 1) Synthesis of (R)-tert-butyl-3-(4-amino-3-((5-chlorobenzo[d]oxazol-2-yl)carbamoyl)-1H-pyrazolo[3,4-d]pyrimidin-1-yl)piperidine-1-carboxylate To a suspension solution of 94 mg of (R)-4-amino-1-(1-(tert-butyloxycarbonyl)piperidin-3-yl)-1H-pyrazolo[3,4-d]pyrimidine-3-carboxylic acid obtained in Synthetic Example 2 in 4 ml of THF, 50 mg of CDT was added, and the mixture was stirred for 3 hours at room temperature. 66 mg of 5-chlorobenzo[d]oxazol-2-amine was added thereto under ice cooling, and a 1.0 M THF solution of lithium hexamethyldisilazane was added dropwise thereto. The mixture was stirred for 30 minutes under ice cooling, 1 ml of water was added thereto, and the solvent THF was removed. A solid obtained by adding 4 ml of water to the residue was separated by filtration, and was washed with 5 ml of hexane/ethyl acetate=1/1. Thus, 106 mg of the title compound was obtained as a white solid. Physical property value: m/z [M+H]$^+$ 513.2

(Step 2) Synthesis of Example Compound 1

1 ml of 4 N hydrochloric acid/1,4-dioxane was added to 5.6 mg of (R)-tert-butyl-3-(4-amino-3-(5-chlorobenzo[d]oxazol-2-ylcarbonyl)-1H-pyrazolo[3,4-d]pyrimidin-1-yl)piperidine-1-carboxylate obtained in (Step 1), the mixture was stirred for 1 hour, and then the solvent was removed using an evaporator. 2 ml of chloroform and 7.6 µl of triethylamine were added to the residue, the mixture was ice-cooled, and then 0.9 µl of acryloyl chloride was added thereto. After the mixture was stirred for 1.5 hours, the reaction was terminated with a saturated aqueous solution of sodium bicarbonate, and extracted with chloroform. The organic layer was dried over sodium sulfate, and then a residue obtained after the removal of the solvent was purified using silica gel column (eluant:ethyl acetate:methanol). Thus, 2.6 mg of the title compound was obtained as a white solid.

Example 2

Synthesis of (R)-1-(1-acryloylpiperidin-3-yl)-4-amino-N-(5-bromobenzo[d]oxazol-2-yl)-1H-pyrazolo[3,4-d]pyrimidine-3-carboxamide (Example Compound 2)

The title compound was obtained as a white solid from (R)-4-amino-1-(1-(tert-butyloxycarbonyl)piperidin-3-yl)-1H-pyrazolo[3,4-d]pyrimidine-3-carboxylic acid of Synthetic Example 2 and 5-bromobenzo[d]oxazol-2-amine according to the procedure described in Example 1.

Example 3

Synthesis of (R)-1-(1-acryloylpiperidin-3-yl)-4-amino-N-(5-(thiophen-2-yl)benzo[d]oxazol-2-yl)-1H-pyrazolo[3,4-d]pyrimidine-3-carboxamide (Example Compound 3)

(Step 1) Synthesis of 5-(thiophen-2-yl)benzo[d]oxazol-2-amine 100 mg of 5-bromobenzo[d]oxazol-2-amine, 249 mg of potassium phosphate, and 90 mg of thiophen-2-ylboronic acid were suspended in 2.5 ml of DME and 0.5 ml of water. 38 mg of 1,1'-bis(diphenylphosphino)ferrocene-palladium (II) dichloride-dichloromethane was added thereto, and the mixture was irradiated at 140° C. for 20 minutes using a microwave reaction apparatus. The solvent was removed from the reaction solution, and the residue was purified by amine gel chromatography (eluent:chloroform/methanol), and thus 93 mg of the title compound was obtained as a pale brown solid. Physical property value: m/z [M+H]$^+$ 216.8

(Step 2) Synthesis of (R)-tert-butyl-3-(4-amino-3-((5-thiophen-2-yl)benzo[d]oxazol-2-yl)carbamoyl)-1H-pyrazolo[3,4-d]pyrimidin-1-yl)piperidine-1-carboxylate To a suspension solution of 19 mg of (R)-4-amino-1-(1-(tert-butyloxycarbonyl)piperidin-3-yl)-1H-pyrazolo[3,4-d]pyrimidine-3-carboxylic acid obtained in Synthetic Example 2 in 2 ml of THF, 10 mg of CDI was added, and the mixture was stirred for 2 hours at room temperature. 17 mg of 5-(thiophen-2-yl)benzo[d]oxazol-2-amine obtained in Step 1 was added thereto under ice cooling, and 105 µl of a 1.0 M THF solution of lithium hexamethyldisilazane was added dropwise thereto. The mixture was stirred for 30 minutes under ice cooling, subsequently 1 ml of water was added thereto, and the solvent THF was removed. A solid obtained by adding 4 ml of water to the residue was separated by filtration, and was washed with 5 ml of hexane/ethyl acetate=1/1. Thus, 13 mg of the target substance was obtained as a pale brown solid. Physical property value: m/z [M+H]$^+$ 561.3

(Step 3) Synthesis of Example Compound 3

1 ml of 4 N hydrochloric acid/1,4-dioxane was added to 9 mg of (R)-tert-butyl-3-(4-amino-3-((5-(thiophen-2-yl)benzo[d]oxazol-2-yl)carbamoyl)-1H-pyrazolo[3,4-d]pyrimidin-1-yl)piperidine-1-carboxylate obtained in (Step 2), the mixture was stirred for 1 hours, and then the solvent was removed using an evaporator. 2 ml of chloroform and 12 µl of triethylamine were added to the residue, the mixture was ice-cooled, and then 1.3 µl of acryloyl chloride was added thereto. After the mixture was stirred for 1.5 hours, the reaction was terminated with a saturated aqueous solution of sodium bicarbonate, and extracted with chloroform. The organic layer was dried over sodium sulfate, and then the residue obtained after solvent removal was purified by reverse phase preparative HPLC purification (water/acetonitrile (0.1% formic acid)). Thus, 2.1 mg of the title compound was obtained as a white solid.

Example 4

Synthesis of (R)-4-amino-N-(5-chlorobenzo[d]ox-azol-2-yl)-1-(1-methacryloylpiperidin-3-yl)-1H-pyrazolo[3,4-d]pyrimidine-3-carboxamide (Example Compound 4)

The title compound was obtained as a white solid according to the procedure described in Example 1, using methacryloyl chloride instead of acryloyl chloride.

Example 5

Synthesis of (R,E)-4-amino-N-(5-chlorobenzo[d]oxazol-2-yl)-1-(1-(but-2-enoyl)piperidin-3-yl)-1H-pyrazolo[3,4-d]pyrimidine-3-carboxamide (Example Compound 5)

The title compound was obtained as a white solid according to the procedure described in Example 1, using crotonic acid chloride instead of acryloyl chloride.

Example 6

Synthesis of (R)-1-(1-acryloylpiperidin-3-yl)-4-amino-N-(5-cyanobenzo[d]oxazol-2-yl)-1H-pyrazolo[3,4-d]pyrimidine-3-carboxamide (Example Compound 6)

(Step 1) Synthesis of (R)-tert-butyl-3-(4-amino-3-((5-cyanobenzo[d]oxazol-2-yl)carbamoyl)-1H-pyrazolo[3,4-d]pyrimidin-1-yl)piperidine-1-carboxylate 2.32 g of (R)-4-amino-1-(1-(tert-butyloxycarbonyl)piperidin-3-yl)-1H-pyrazolo[3,4-d]pyrimidine-3-carboxylic acid obtained in Synthetic Example 2 was dissolved in 25 ml of DMA, 2.01 g of CDI was added thereto, and the mixture was stirred for 1 hour at room temperature. 1.12 g of 5-cyanobenzo[d]oxazol-2-amine was added to the reaction solution, and thereafter, 1.23 g of sodium tert-butyrate was added thereto. The mixture was stirred for 2 hours at room temperature, and water was added thereto. Subsequently, the pH was adjusted with 2 N hydrochloric acid, and thereby a solid was precipitated therefrom. The solid was collected by filtration and dried. Thus, 2.66 g of the title compound was obtained as a pale yellow solid. Physical property value: m/z [M+H]$^+$ 505.3

(Step 2) Synthesis of Example Compound 6

2.1 g of (R)-tert-butyl-3-(4-amino-3-((5-cyanobenzo[d]oxazol-2-yl)carbamoyl)-1H-pyrazolo[3,4-d]pyrimidin-1-yl)piperidine-1-carboxylate obtained in Step 1 was suspended in 10 ml of dichloromethane, and 10 ml of TFA was added thereto at room temperature. The mixture was stirred for 2 hours, and then the TFA was removed using an evaporator. Furthermore, the residue was azeotropically distilled with toluene, the residue was mixed with 20 ml of NMP and 2 ml of water, and the mixture was ice-cooled. 2.88 g of potassium carbonate and 0.4 ml of acryloyl chloride were added thereto, and the mixture was stirred under ice cooling. After 2 hours, water and 2 N hydrochloric acid were added thereto to adjust the pH, and a solid thus obtained was collected by filtration. Thereafter, the solid was purified by silica gel chromatography (chloroform-methanol), and thus 0.7 g of the target substance was obtained as a white solid.

Example 7

Synthesis of (R)-1-(1-acryloylpiperidin-3-yl)-4-amino-N-(5-methoxybenzo[d]oxazol-2-yl)-1H-pyrazolo[3,4-d]pyrimidin-3-carboxamide (Example Compound 7)

The title compound was obtained as a pale brown solid according to the procedure described in Example 6, from (R)-4-amino-1-(1-(tert-butyloxycarbonyl)piperidin-3-yl)-1H-pyrazolo[3,4-d]pyrimidine-3-carboxylic acid of Synthetic Example 2 and 5-methoxybenzo[d]oxazol-2-amine.

Example 8

Synthesis of (R)-1-(1-acryloylpiperidin-3-yl)-4-amino-N-(5-(2-methoxyethyl)benzo[d]oxazol-2-yl)-1H-pyrazolo[3,4-d]pyrimidine-3-carboxamide (Example Compound 8)

The title compound was obtained as a white solid according to the procedure described in Example 6, from (R)-4-amino-1-(1-(tert-butyloxycarbonyl)piperidin-3-yl)-1H-pyrazolo[3,4-d]pyrimidine-3-carboxylic acid of Synthetic Example 2 and 5-(2-methoxyethyl)benzo[d]oxazol-2-amine.

Example 9

Synthesis of (R)-1-(1-acryloylpiperidin-3-yl)-4-amino-N-(oxazolo[4,5-b]pyridin-2-yl)-1H-pyrazolo[3,4-d]pyrimidine-3-carboxamide (Example Compound 9)

The title compound was obtained as a white solid according to the procedure described in Example 6, from (R)-4-amino-1-(1-(tert-butyloxycarbonyl)piperidin-3-yl)-1H-pyrazolo[3,4-d]pyrimidine-3-carboxylic acid of Synthetic Example 2 and oxazolo[4,5-b]pyridin-2-amine.

Example 10

Synthesis of (R)-1-(1-acryloylpiperidin-3-yl)-4-amino-N-(4-methylbenzo[d]oxazol-2-yl)-1H-pyrazolo[3,4-d]pyrimidine-3-carboxamide (Example Compound 10)

The title compound was obtained as a white solid according to the procedure described in Example 6, from (R)-4-amino-1-(1-(tert-butyloxycarbonyl)piperidin-3-yl)-1H-pyrazolo[3,4-d]pyrimidine-3-carboxylic acid of Synthetic Example 2 and 4-methylbenzo[d]oxazol-2-amine.

Example 11

Synthesis of (R)-4-amino-N-(5-fluorobenzo[d]oxazol-2-yl)-1-(1-methacryloylpiperidin-3-yl)-1H-pyrazolo[3,4-d]pyrimidine-3-carboxamide (Example Compound 11)

The title compound was obtained as a white solid according to the procedure described in Example 6, using (R)-4-amino-N-(5-fluorobenzo[d]oxazol-2-yl)-1-(piperidin-3-yl)-1H-pyrazolo[3,4-d]pyrimidine-3-carboxamide obtained in Example 12 (Step 2), and using methacryloyl chloride instead of acryloyl chloride.

Example 12

Synthesis of (R)-1-(1-acryloylpiperidin-3-yl)-4-amino-N-(5-fluorobenzo[d]oxazol-2-yl)-1H-pyrazolo[3,4-d]pyrimidine-3-carboxamide (Example Compound 12)

(Step 1) Synthesis of (R)-tert-butyl-3-(4-amino-3-((5-fluorobenzo[d]oxazol-2-yl)carbamoyl)-1H-pyrazolo[3,4-d]pyrimidin-1-yl)piperidine-1-carboxylate To a solution of 1.0 g of (R)-4-amino-1-(1-(tert-butyloxycarbonyl)piperidin-3-yl)-1H-pyrazolo[3,4-d]pyrimidine-3-carboxylic acid obtained in Synthetic Example 2 in 10 ml of DMA, 895 mg of CDI was added, and the mixture was stirred for 1 hour at room temperature. 462 mg of 5-fluorobenzo[d]oxazol-2-amine was added thereto, and 9 ml of a 1.0 M THF solution of sodium tert-butyrate was added dropwisely thereto. The mixture was stirred for 30 minutes at room temperature, and then 10 ml of a 1 N aqueous solution of NaOH was added thereto, and the solvent THF was removed. After the residue was stirred for 1 hour, 2 N HCl and water-MeOH were added thereto to precipitate the mixture. Subsequently, a solid thus obtained was collected by filtration, and thus 1.14 g of the title compound was obtained as a light yellow solid. Physical property value: m/z [M+H]$^+$ 497.2

(Step 2) Synthesis of (R)-4-amino-N-(5-fluorobenzo[d]oxazol-2-yl)-1-(piperidin-3-yl)-1H-pyrazolo[3,4-d]pyrimidine-3-carboxamide 3.06 g of (R)-tert-butyl-3-(4-amino-3-(5-fluorobenzo[d]oxazol-2-ylcarbonyl)-1H-pyrazolo[3,4-d]pyrimidin-1-yl)piperidine-1-carboxylate obtained in Step 1 and 5.5 g of sodium iodide were suspended in 30 ml of acetonitrile, and 4.7 ml of trimethylsilyl chloride was added thereto at room temperature. The mixture was stirred for 1 hour at room temperature, a saturated aqueous solution of sodium bicarbonate was added thereto, and thereby a solid was precipitated. After the system was stirred for 10 minutes, the solid was collected by filtration and dried, and thus 2.07 g of the title compound was obtained as a light brown solid. Physical property value: m/z [M+H]$^+$ 398.0

(Step 3) Synthesis of Example Compound 12

2 g of (R)-4-amino-N-(5-fluorobenzo[d]oxazol-2-yl)-1-(piperidin-3-yl)-1H-pyrazolo[3,4-d]pyrimidine-3-carboxamide obtained in Step 2 and 2.1 g of potassium carbonate were dissolved in 20 ml of NMP and 2 ml of water, and the solution was stirred under ice cooling. 0.4 ml of acryloyl chloride was added thereto, and the mixture was stirred for 1 hour. Water was added thereto, and the pH was adjusted with hydrochloric acid. A solid precipitated therefrom was collected by filtration. The solid thus collected by filtration was purified by silica gel chromatography (eluent:chloroform-methanol), and 1.79 g of the title compound was obtained as a white solid.

Example 13

Synthesis of (R)-1-(1-acryloylpiperidin-3-yl)-4-amino-N-(benzo[d]oxazol-2-yl)-1H-pyrazolo[3,4-d]pyrimidine-3-carboxamide (Example Compound 13)

(Step 1) Synthesis of (R)-tert-butyl-3-(4-amino-3-((benzo[d]oxazol-2-yl)carbamoyl)-1H-pyrazolo[3,4-d]pyrimidin-1-yl)piperidine-1-carboxylate 300 mg of (R)-tert-butyl 3-(4-amino-3-iodo-1H-pyrazolo[3,4-d]pyrimidin-1-yl)piperidine-1-carboxylate obtained in Synthetic Example 1 was dissolved in 3 ml of NMP. 118 mg of benzo[d]oxazol-2-amine, 20 mg of xantphos, and 0.15 ml of N-methylmorpholine were added thereto, and a degassing operation was carried out. Thereafter, 7.6 mg of palladium acetate was added thereto, and in a carbon monoxide atmosphere, the mixture was heated to 110° C. and stirred for 2 hours. After the mixture was cooled, 4.5 ml of methanol and 0.45 ml of a 5 N aqueous solution of sodium hydroxide were added thereto, and the mixture was stirred for 30 minutes at room temperature. Thereafter, the pH was adjusted to 5.3 with 2 N HCl, and a solid thus obtained was collected by filtration. The crude product was purified using a silica gel column (eluent:chloroform-methanol), and thus 257 mg of the title compound was obtained as a white solid. Physical property value: m/z [M+H]$^+$ 479.3

(Step 2) Synthesis of Example Compound 13

5 g of (R)-tert-butyl-3-(4-amino-3-((benzo[d]oxazol-2-yl)carbamoyl)-1H-pyrazolo[3,4-d]pyrimidin-1-yl)piperidine-1-carboxylate obtained in Step 1 was suspended in 50 ml of acetonitrile, and 7.85 g of sodium iodide was added thereto. 6.65 ml of trimethylsilyl chloride was added dropwise thereto with stirring at room temperature, and the mixture was stirred for 1 hour. 87.5 ml of water and 12.5 ml of a 5 N aqueous solution of sodium hydroxide were added thereto, and then the system was ice-cooled. 0.895 ml of acryloyl chloride was added dropwise thereto, and the mixture was stirred for 1 hour under ice cooling. A solid obtained by adding water thereto was collected by filtration, washed with water, and dried. Thus, 4.13 g of the title compound was obtained as a white solid.

Example 14

Synthesis of (R,E)-4-amino-N-(benzo[d]oxazol-2-yl)-1-(1-(but-2-enoyl)piperidin-3-yl)-1H-pyrazolo[3,4-d]pyrimidine-3-carboxamide (Example Compound 14)

The title compound was obtained as a white solid according to the procedure described in Example 13, using crotonic acid chloride instead of acryloyl chloride.

Example 15

Synthesis of (R,E)-4-amino-N-(5-chlorobenzo[d]oxazol-2-yl)-1-(1-(4-(dimethylamino)but-2-enoyl)piperidin-3-yl)-1H-pyrazolo[3,4-d]pyrimidine-3-carboxamide (Example Compound 15)

1 ml of 4 N hydrochloric acid/1,4-dioxane was added to 5 mg of (R)-tert-butyl-3-(4-amino-3-((5-chlorobenzo[d]oxazol-2-yl)carbamoyl)-1H-pyrazolo[3,4-d]pyrimidin-1-yl)piperidine-1-carboxylate obtained in Step 1 of Example 1, and the mixture was stirred for 10 minutes. Thereafter, the solvent was removed using an evaporator, and the system was azeotropically distilled with toluene. The residue was dissolved in 1 ml of DMF, and 8.5 μl of diisopropylethylamine, 2.4 mg of (E)-4-(dimethylamino)but-2-enoic acid hydrochloride, and 5.5 mg of HATU were added thereto. The mixture was stirred for 1 hour at room temperature, and then the solution was concentrated under reduced pressure. The residue was purified by reverse phase preparative HPLC purification (water/acetonitrile (0.1% formic acid)), and thus 3.96 mg of the title compound was obtained as a white solid.

Example 16

Synthesis of (R,E)-4-amino-N-(5-chlorobenzo[d]oxazol-2-yl)-1-(1-(4-(ethyl(methyl)amino)but-2-enoyl)piperidin-3-yl)-1H-pyrazolo[3,4-d]pyrimidine-3-carboxamide (Example Compound 16)

The title compound was obtained as a white solid according to the procedure described in Example 15, using (E)-4-(ethyl(methyl)amino)but-2-enoic acid hydrochloride instead of (E)-4-(dimethylamino)but-2-enoic acid hydrochloride.

Example 17

Synthesis of (R,E)-4-amino-N-(5-chlorobenzo[d]oxazol-2-yl)-1-(1-(4-(diethylamino)but-2-enoyl)piperidin-3-yl)-1H-pyrazolo[3,4-d]pyrimidine-3-carboxamide (Example Compound 17)

The title compound was obtained as a white solid according to the procedure described in Example 15, using (E)-4-(diethylamino)but-2-enoic acid hydrochloride instead of (E)-4-(dimethylamino)but-2-enoic acid hydrochloride.

Example 18

Synthesis of (R,E)-4-amino-N-(5-chlorobenzo[d]oxazol-2-yl)-1-(1-(4-(isopropyl(methyl)amino)but-2-enoyl)piperidin-3-yl)-1H-pyrazolo[3,4-d]pyrimidine-3-carboxamide (Example Compound 18)

The title compound was obtained as a white solid according to the procedure described in Example 15, using (E)-4-(isopropyl(methyl)amino)but-2-enoic acid hydrochloride instead of (E)-4-(dimethylamino)but-2-enoic acid hydrochloride.

Example 19

Synthesis of (R,E)-4-amino-N-(5-chlorobenzo[d]oxazol-2-yl)-1-(1-(4-(pyrrolidin-1-yl)but-2-enoyl)piperidin-3-yl)-1H-pyrazolo[3,4-d]pyrimidine-3-carboxamide (Example Compound 19)

The title compound was obtained as a white solid according to the procedure described in Example 15, using (E)-4-(pyrrolidin-1-yl)but-2-enoic acid hydrochloride instead of (E)-4-(dimethylamino)but-2-enoic acid hydrochloride.

Example 20

Synthesis of (R,E)-4-amino-N-(5-chlorobenzo[d]oxazol-2-yl)-1-(1-(4-(piperidin-1-yl)but-2-enoyl)piperidin-3-yl)-1H-pyrazolo[3,4-d]pyrimidine-3-carboxamide (Example Compound 20)

The title compound was obtained as a white solid according to the procedure described in Example 15, using (E)-4-(piperidin-1-yl)but-2-enoic acid hydrochloride instead of (E)-4-(dimethylamino)but-2-enoic acid hydrochloride.

Example 21

Synthesis of (R,E)-4-amino-N-(5-(thiophen-2-yl)benzo[d]oxazol-2-yl)-1-(1-(4-(dimethylamino)but-2-enoyl)piperidin-3-yl)-1H-pyrazolo[3,4-d]pyrimidine-3-carboxamide (Example Compound 21)

The title compound was obtained as a white solid according to the procedure described in Example 15, using (R)-tert-butyl-3-(4-amino-3-((5-(thiophen-2-yl)benzo[d]oxazol-2-yl)carbamoyl)-1H-pyrazolo[3,4-d]pyrimidin-1-yl)piperidine-1-carboxylate obtained in Example 3 (Step 2).

Example 22

Synthesis of (R)-4-amino-N-(benzo[d]oxazol-2-yl)-1-(1-(but-2-ynoyl)piperidin-3-yl)-1H-pyrazolo[3,4-d]pyrimidine-3-carboxamide (Example Compound 22)

The title compound was obtained as a pale yellow solid according to the procedure described in Example 15, using (R)-tert-butyl-3-(4-amino-3-((benzo[d]oxazol-2-yl)carbamoyl)-1H-pyrazolo[3,4-d]pyrimidin-1-yl)piperidine-1-carboxylate obtained in Example 13 (Step 1), and but-2-ynoic acid instead of (E)-4-(dimethylamino)but-2-enoic acid hydrochloride.

Example 23

Synthesis of (R)-1-(1-acryloylpiperidin-3-yl)-4-amino-N-(5,6-dimethylbenzo[d]oxazol-2-yl)-1H-pyrazolo[3,4-d]pyrimidine-3-carboxamide (Example Compound 23)

(Step 1) Synthesis of (R)-1-(1-acyloxypiperidin-3-yl)-4-amino-1H-pyrazolo[3,4-d]pyrimidine-3-carboxylic acid To 1 g of (R)-4-amino-1-(1-(tert-butyloxycarbonyl)piperidin-3-yl)-1H-pyrazolo[3,4-d]pyrimidine-3-carboxylic acid of Synthetic Example 3, 15 ml of 4 N hydrochloric acid/1,4-dioxane was added, and the mixture was stirred for 1 hour at room temperature. Thereafter, the solvent was removed, and the system was azeotropically distilled by adding toluene thereto. 50 ml of chloroform and 3.8 ml of triethylamine were added to the residue. While the mixture was stirred, 780 μl of acryloyl chloride was slowly added thereto. After completion of the reaction was confirmed, the reaction was terminated by adding 2-propanol. The solvent was removed, and an aqueous solution of formic acid was added to the residue. When the mixture was adjusted to pH 3, a solid was precipitated. A solid thus obtained was collected by filtration and dried, and thus 840 mg of the title compound was obtained as a yellow solid. Physical property value: m/z [M+H]$^+$ 318.1

(Step 2) Synthesis of Example Compound 23

5 mg of (R)-1-(1-acyloxypiperidin-3-yl)-4-amino-1H-pyrazolo[3,4-d]pyrimidine-3-carboxylic acid obtained in the above Step 1 was dissolved in 150 µl of DMF. To that solution, 8.26 µl of diisopropylethylamine, 3.85 mg of 5,6-dimethylbenzo[d]oxazol-2-amine, and 9 mg of HATU were added. After the mixture was stirred overnight, 850 µl of DMSO was added thereto, and the mixture was purified by reverse phase preparative HPLC purification (water/acetonitrile (0.1% formic acid)). Thus, 1.2 mg of the title compound was obtained as a white solid.

Example 24

Synthesis of (R)-1-(1-acryloylpyrrolidin-3-yl)-4-amino-N-(5-chlorobenzo[d]oxazol-2-yl)-1H-pyrazolo[3,4-d]pyrimidine-3-carboxamide (Example Compound 24)

(Step 1) Synthesis of (R)-tert-butyl-3-(4-amino-3-((5-chlorobenzo[d]oxazol-2-yl)carbamoyl)-1H-pyrazolo[3,4-d]pyrimidin-1-yl)pyridine-1-carboxylate To a solution of 100 mg of (R)-4-amino-1-(1-(tert-butyloxycarbonyl)pyrrolidin-3-yl)-1H-pyrazolo[3,4-d]pyrimidine-3-carboxylic acid obtained in Synthetic Example 3 in 5 ml of DMF, 56 mg of CDT was added, and the mixture was stirred for 1 hour at room temperature. 73 mg of 5-chlorobenzo[d]oxazol-2-amine was added thereto under ice cooling, and 17 mg of 60% sodium hydride was added thereto. After the mixture was stirred for 30 minutes under ice cooling, 1 ml of water was added thereto to terminate the reaction. The reaction solution was concentrated, and was purified by silica gel column chromatography (eluant: chloroform-methanol). Thus, 114 mg of the title compound was obtained as a white solid. Physical property value: m/z [M+H]$^+$ 499.1

(Step 2) Synthesis of Example Compound 24

15 mg of (R)-tert-butyl-3-(4-amino-3-((5-chlorobenzo[d]oxazol-2-yl)carbamoyl)-1H-pyrazolo[3,4-d]pyrimidin-1-yl)pyrrolidine-1-carboxylate obtained in Step 1 was mixed with 1.5 ml of 4 N hydrochloric acid/1,4-dioxane, the mixture was stirred for 1 hour, and then the solvent was removed using an evaporator. 2 ml of chloroform and 21 µl of triethylamine were added to the residue, the mixture was ice-cooled, and then 2.4 µl of acryloyl chloride was added thereto. After the mixture was stirred for 3 hours, the reaction was terminated with a saturated aqueous solution of sodium bicarbonate, and extracted with chloroform. The organic layer was dried over sodium sulfate, and then a residue obtained after removal of the solvent was purified using a silica gel column (eluant:ethyl acetate:methanol). Thus, 6.8 mg of the title compound was obtained as a white solid.

Example 25

Synthesis of (R,E)-4-amino-N-(5-chlorobenzo[d]oxazol-2-yl)-1-(1-(but-2-enoyl)pyrrolidin-3-yl)-1H-pyrazolo[3,4-d]pyrimidine-3-carboxamide (Example Compound 25)

The title compound was obtained as a white solid according to the procedure described in Example 24, using crotonic acid chloride instead of acryloyl chloride.

Example 26

Synthesis of (R,E)-4-amino-N-(5-chlorobenzo[d]oxazol-2-yl)-1-(1-(3-methylbut-2-enoyl)pyrrolidin-3-yl)-1H-pyrazolo[3,4-d]pyrimidine-3-carboxamide (Example Compound 26)

The title compound was obtained as a white solid according to the procedure described in Example 24, using 3-methylbut-2-enoyl chloride instead of acryloyl chloride.

Example 27

Synthesis of (R)-1-(1-acryloylpyrrolidin-3-yl)-4-amino-N-(benzo[d]oxazol-2-yl)-1H-pyrazolo[3,4-d]pyrimidine-3-carboxamide (Example Compound 27)

The title compound was obtained as a white solid according to the procedure described in Example 24, from (R)-4-amino-1-(1-(tert-butyloxycarbonyl)pyrrolidin-3-yl)-1H-pyrazolo[3,4-d]pyrimidine-3-carboxylic acid of Synthetic Example 3 and benzo[d]oxazol-2-amine.

Example 28

Synthesis of (R)-1-(1-acryloylpyrrolidin-3-yl)-4-amino-N-(5-(thiophen-2-yl)benzo[d]oxazol-2-yl)-1H-pyrazolo[3,4-d]pyrimidine-3-carboxamide (Example Compound 28)

The title compound was obtained as a white solid according to the procedure described in Example 24, from (R)-4-amino-1-(1-(tert-butyloxycarbonyl)pyrrolidin-3-yl)-1H-pyrazolo[3,4-d]pyrimidine-3-carboxylic acid of Synthetic Example 3 and 5-(thiophen-2-yl)benzo[d]oxazol-2-amine.

Example 29

Synthesis of (R)-1-(1-acryloylpyrrolidin-3-yl)-4-amino-N-(5-methylbenzo[d]oxazol-2-yl)-1H-pyrazolo[3,4-d]pyrimidine-3-carboxamide (Example Compound 29)

The title compound was obtained as a pale yellow according to the procedure described in Example 24, from (R)-4-amino-1-(1-(tert-butyloxycarbonyl)pyrrolidin-3-yl)-1H-pyrazolo[3,4-d]pyrimidine-3-carboxylic acid of Synthetic Example 3 and 5-methylbenzo[d]oxazol-2-amine.

Example 30

Synthesis of (R)-1-(1-acryloylpyrrolidin-3-yl)-4-amino-N-(5-fluorobenzo[d]oxazol-2-yl)-1H-pyrazolo[3,4-d]pyrimidine-3-carboxamide (Example Compound 30)

The title compound was obtained as a pale yellow solid according to the procedure described in Example 24, from (R)-4-amino-1-(1-(tert-butyloxycarbonyl)pyrrolidin-3-yl)-1H-pyrazolo[3,4-d]pyrimidine-3-carboxylic acid of Synthetic Example 3 and 5-fluorobenzo[d]oxazol-2-amine.

Example 31

Synthesis of (R)-1-(1-acryloylpyrrolidin-3-yl)-4-amino-N-(5-(4-chlorophenyl)benzo[d]oxazol-2-yl)-1H-pyrazolo[3,4-d]pyrimidine-3-carboxamide (Example Compound 31)

(Step 1) Synthesis of 5-(4-chlorophenyl)benzo[d]oxazol-2-amine

The title compound was obtained as a white solid according to the procedure described in Step 1 of Example 3, using 4-chlorophenylboronic acid instead of thiophen-2-ylboronic acid. Physical property value: m/z [M+H]$^+$ 245.1

(Step 2) Synthesis of Example Compound 31

The title compound was obtained as a white solid according to the procedure described in Example 24, from (R)-4-amino-1-(1-(tert-butyloxycarbonyl)pyrrolidin-3-yl)-1H-pyrazolo[3,4-d]pyrimidine-3-carboxylic acid of Synthetic Example 3 and 5-(4-chlorophenyl)benzo[d]oxazol-2-amine obtained in the above Step 1.

Example 32

Synthesis of (R,E)-4-amino-N-(5-chlorobenzo[d]oxazol-2-yl)-1-(1-(4-(dimethylamino)but-2-enoyl)pyrrolidin-3-yl)-1H-pyrazolo[3,4-d]pyrimidine-3-carboxamide (Example Compound 32)

To 15 mg of (R)-tert-butyl-3-(4-amino-3-((5-chlorobenzo[d]oxazol-2-yl)carbamoyl)-1H-pyrazolo[3,4-d]pyrimidin-1-yl)pyrrolidine-1-carboxylate obtained in Step 1 of Example 24, 1.5 ml of 4 N hydrochloric acid/1,4-dioxane was added, and the mixture was stirred for 10 minutes. Thereafter, the solvent was removed using an evaporator, and the residue was azeotropically distilled with toluene. The residue was dissolved in 1 ml of DMF, and 13 μl of diisopropylethylamine, 3.7 mg of (E)-4-(dimethylamino)but-2-enoic acid hydrochloride, and 8.4 mg of HATU were added thereto. After the mixture was stirred for 1 hour at room temperature, the solution was concentrated under reduced pressure. The residue was purified by reverse phase preparative HPLC purification (water/acetonitrile (0.1% formic acid)), and thus 4.2 mg of the title compound was obtained as a white solid.

Example 33

Synthesis of (R,E)-4-amino-N-(5-chlorobenzo[d]oxazol-2-yl)-1-(1-(4-(ethyl(methyl)amino)but-2-enoyl)pyrrolidin-3-yl)-1H-pyrazolo[3,4-d]pyrimidine-3-carboxamide (Example Compound 33)

The title compound was obtained as a white solid according to the procedure described in Example 32, using (E)-4-(ethyl(methyl)amino)but-2-enoic acid hydrochloride instead of (E)-4-(dimethylamino)but-2-enoic acid hydrochloride.

Example 34

Synthesis of (R,E)-4-amino-N-(5-chlorobenzo[d]oxazol-2-yl)-1-(1-(4-(diethylamino)but-2-enoyl)pyrrolidin-3-yl)-1H-pyrazolo[3,4-d]pyrimidine-3-carboxamide (Example Compound 34)

The title compound was obtained as a white solid according to the procedure described in Example 32, using (E)-4-(diethylamino)but-2-enoic acid hydrochloride instead of (E)-4-(dimethylamino)but-2-enoic acid hydrochloride.

Example 35

Synthesis of (R,E)-4-amino-N-(5-chlorobenzo[d]oxazol-2-yl)-1-(1-(4-(isopropyl(methyl)amino)but-2-enoyl)pyrrolidin-3-yl)-1H-pyrazolo[3,4-d]pyrimidine-3-carboxamide (Example Compound 35)

The title compound was obtained as a white solid according to the procedure described in Example 32, using (E)-4-(isopropyl(methyl)amino)but-2-enoic acid hydrochloride instead of (E)-4-(dimethylamino)but-2-enoic acid hydrochloride.

Example 36

Synthesis of (R,E)-4-amino-N-(5-chlorobenzo[d]oxazol-2-yl)-1-(1-(4-(pyrrolidin-1-yl)but-2-enoyl)pyrrolidin-3-yl)-1H-pyrazolo[3,4-d]pyrimidine-3-carboxamide (Example Compound 36)

The title compound was obtained as a white solid according to the procedure described in Example 32, using (E)-4-(pyrrolidin-1-yl)but-2-enoic acid hydrochloride instead of (E)-4-(dimethylamino)but-2-enoic acid hydrochloride.

Example 37

Synthesis of (R,E)-4-amino-N-(5-chlorobenzo[d]oxazol-2-yl)-1-(1-(4-(piperidin-1-yl)but-2-enoyl)pyrrolidin-3-yl)-1H-pyrazolo[3,4-d]pyrimidine-3-carboxamide (Example Compound 37)

The title compound was obtained as a white solid according to the procedure described in Example 32, using (E)-4-(piperidin-1-yl)but-2-enoic acid hydrochloride instead of (E)-4-(dimethylamino)but-2-enoic acid hydrochloride.

Example 38

Synthesis of (R)-1-(1-acryloylpyrrolidin-3-yl)-4-amino-N-(5-methoxybenzo[d]oxazol-2-yl)-1H-pyrazolo[3,4-d]pyrimidine-3-carboxamide (Example Compound 38)

The title compound was obtained as a white solid according to the procedure described in Example 6, from (R)-4-amino-1-(1-(tert-butyloxycarbonyl)pyrrolidin-3-yl)-1H-pyrazolo[3,4-d]pyrimidine-3-carboxylic acid of Synthetic Example 3 and 5-methoxybenzo[d]oxazol-2-amine.

Example 39

Synthesis of (R)-1-(1-acryloylpyrrolidin-3-yl)-4-amino-N-(5-cyanobenzo[d]oxazol-2-yl)-1H-pyrazolo[3,4-d]pyrimidine-3-carboxamide (Example Compound 39)

The title compound was obtained as a white solid according to the procedure described in Example 6, from (R)-4-amino-1-(1-(tert-butyloxycarbonyl)pyrrolidin-3-yl)-1H-pyrazolo[3,4-d]pyrimidine-3-carboxylic acid of Synthetic Example 3 and 5-cyanobenzo[d]oxazol-2-amine.

Example 40

Synthesis of (R)-1-(1-acryloylpyrrolidin-3-yl)-4-amino-N-(5-(2-methoxyethyl)benzo[d]oxazol-2-yl)-1H-pyrazolo[3,4-d]pyrimidine-3-carboxamide (Example Compound 40)

The compound was obtained as a pale yellow solid according to the procedure described in Example 6, from (R)-4-amino-1-(1-(tert-butyloxycarbonyl)pyrrolidin-3-yl)-1H-pyrazolo[3,4-d]pyrimidine-3-carboxylic acid of Synthetic Example 3 and 5-(2-methoxyethyl)benzo[d]oxazol-2-amine.

Example 41

Synthesis of (R)-1-(1-acryloylpyrrolidin-3-yl)-4-amino-N-(5-phenylbenzo[d]oxazol-2-yl)-1H-pyrazolo[3,4-d]pyrimidine-3-carboxamide (Example Compound 41)

(Step 1) Synthesis of (R)-tert-butyl-3-(4-amino-3-((5-phenylbenzo[d]oxazol-2-yl)carbamoyl)-1H-pyrazolo[3,4-d]pyrimidin-1-yl)pyrrolidine-1-carboxylate 20 mg of (R)-4-amino-1-(1-(tert-butyloxycarbonyl)pyrrolidin-3-yl)-1H-pyrazolo[3,4-d]pyrimidine-3-carboxylic acid of Synthetic Example 3 was suspended in 1 ml of THF, and 12 mg of CDT was added thereto at room temperature with stirring. The mixture was stirred overnight at room temperature, 24 mg of 5-phenylbenzo[d]oxazol-2-amine was added thereto, and then the mixture was ice-cooled. 172 µl of a 1.0 M THF solution of lithium hexamethyldisilazane was added dropwise thereto. After the mixture was stirred for 1 hour, the reaction was terminated by adding 30 µl of acetic acid thereto. After the solvent was removed, the residue was purified by reverse phase preparative HPLC purification (water/acetonitrile (0.1% formic acid)), and thus 12.8 mg of the title compound was obtained as a white solid. Physical property value: m/z [M+H]$^+$ 541.1

(Step 2) Synthesis of Example Compound 41

To 12.8 mg of (R)-tert-butyl-3-(4-amino-3-((5-phenylbenzo[d]oxazol-2-yl)carbamoyl)-1H-pyrazolo[3,4-d]pyrimidin-1-yl)pyrrolidine-1-carboxylate obtained in the above Step 1, 1.5 ml of 4 N hydrochloric acid/1,4-dioxane was added, and the mixture was stirred for 1 hour. Thereafter, the solvent was removed, and the system as azeotropically distilled with 1 ml of toluene. 1 ml of chloroform and 16 µl of triethylamine were added to the residue, and the mixture was stirred under ice cooling. 1.9 µl of acryloyl chloride was added to the solution, and the mixture was stirred for 1 hour. Subsequently, the reaction was terminated with a saturated aqueous solution of sodium bicarbonate, and extracted using chloroform. The organic layer was dried over sodium sulfate, and then a residue obtained after removal of the solvent was purified by reverse phase preparative HPLC purification (water/acetonitrile (0.1% formic acid)). Thus, 3.46 mg of the title compound was obtained as a white solid.

Example 42

Synthesis of (R,E)-4-amino-N-(5-phenylbenzo[d]oxazol-2-yl)-1-(1-(4-(dimethylamino)but-2-enoyl)pyrrolidin-3-yl)-1H-pyrazolo[3,4-d]pyrimidine-3-carboxamide (Example Compound 42)

To 5 mg of (R)-tert-butyl-3-(4-amino-3-((5-phenylbenzo[d]oxazol-2-yl)carbamoyl)-1H-pyrazolo[3,4-d]pyrimidin-1-yl)pyrrolidine-1-carboxylate obtained in Step 1 of Example 41, 1 ml of N hydrochloric acid/1,4-dioxane was added, and the mixture was stirred for 30 minutes. Thereafter, the solvent was removed, and the residue was azeotropically distilled with 1 ml of toluene. The residue was dissolved in 1 ml of DMF, 7.9 µl of diisopropylethylamine, 2.2 mg of (E)-4-(dimethylamino)but-2-enoic acid hydrochloride, and 5.18 mg of HATU were added thereto. The mixture was stirred for 1 hour at room temperature, and then the solution was concentrated under reduced pressure. The residue was purified by reverse phase preparative HPLC purification (water/acetonitrile (0.1% formic acid)). Thus, 3.04 mg of the title compound was obtained as a white solid.

Example 43

Synthesis of (R)-1-(1-acryloylpyrrolidin-3-yl)-4-amino-N-(5-(trifluoromethyl)benzo[d]oxazol-2-yl)-1H-pyrazolo[3,4-d]pyrimidine-3-carboxamide (Example Compound 43)

(Step 1) Synthesis of (R)-tert-butyl-3-(4-amino-3-((5-(trifluoromethyl)benzo[d]oxazol-2-yl)carbamoyl)-1H-pyrazolo[3,4-d]pyrimidin-1-yl)pyrrolidine-1-carboxylate 32 mg of (R)-4-amino-1-(1-(tert-butyloxycarbonyl)pyrrolidin-3-yl)-1H-pyrazolo[3,4-d]pyrimidine-3-carboxylic acid of Synthetic Example 3 was suspended in 2 ml of THF, and 55 mg of CDI was added thereto at room temperature with stirring. The mixture was stirred overnight at room temperature, and 28 mg of 5-(trifluoromethyl)benzo[d]oxazol-2-amine was added thereto. Subsequently, the mixture was ice-cooled, and 183 µl of a 1.0 M THF solution of lithium hexamethyldisilazane was added dropwise thereto. After the mixture was stirred for 1 hour, a solid obtained by adding water thereto was collected by filtration. The solid was washed with a mixed solvent of hexane/ethyl acetate, and thus 35 mg of the title compound was obtained as a pale yellow solid. Physical property value: m/z [M+H]$^+$ 533.3

(Step 2) Synthesis of compound of Example 43

500 µl of dichloromethane was added to 8 mg of (R)-tert-butyl-3-(4-amino-3-((5-(trifluoromethyl)benzo[d]oxazol-2-yl)carbamoyl)-1H-pyrazolo[3,4-d]pyrimidin-1-yl)pyrrolidine-1-carboxylate obtained in the above Step 1, and 200 µl of trifluoroacetic acid was added thereto. The mixture was stirred for 30 minutes. Thereafter, the solvent was removed, and the residue was azeotropically distilled with 1 ml of toluene. 2 ml of chloroform and 11 µl of triethylamine were added to the residue, and the mixture was stirred under ice cooling. 1.2 µl of acryloyl chloride was added to the solution, and the mixture was stirred for 1 hour. Subsequently, the reaction was terminated with a saturated aqueous solution of sodium bicarbonate, and extracted with chloroform. The organic layer was dried over sodium sulfate, and then a residue obtained after removal of the solvent was purified by reverse phase preparative HPLC purification (water/acetonitrile (0.1% formic acid)). Thus, 1.58 mg of the title compound was obtained as a white solid.

Example 44

Synthesis of (R,E)-4-amino-N-(5-(trifluoromethyl) benzo[d]oxazol-2-yl)-1-(1-(4-(dimethylamino)but-2-enoyl)pyrrolidin-3-yl)-1H-pyrazolo[3,4-d]pyrimidine-3-carboxamide (Example Compound 44)

To 5 mg of (R)-tert-butyl-3-(4-amino-3-((5-(trifluoromethyl)benzo[d]oxazol-2-yl)carbamoyl)-1H-pyrazolo[3,4-d]pyrimidin-1-yl)pyrrolidine-1-carboxylate obtained in Step 1 of Example 43, 500 µl of dichloromethane was added, and 200 µl of trifluoroacetic acid was further added thereto. The mixture was stirred for 30 minutes. Thereafter, the solvent was removed, and the residue was azeotropically distilled with 1 ml of toluene. The residue was dissolved in 1 ml of DMF, and 6.5 µl of diisopropylethylamine, 1.9 mg of (E)-4-(dimethylamino)but-2-enoic acid hydrochloride, and 4.3 mg of HATU were added thereto. The mixture was stirred for 1 hour at room temperature, and then the solution was concentrated under reduced pressure. The residue was purified by reverse phase preparative HPLC purification (water/acetonitrile (0.1% formic acid)), and thus 2.88 mg of the title compound was obtained as a white solid.

Example 45

Synthesis of 1-(1-acryloylazetidin-3-yl)-4-amino-N-(5-chlorobenzo[d]oxazol-2-yl)-1H-pyrazolo[3,4-d]pyrimidine-3-carboxamide (Example Compound 45)

(Step 1) Synthesis of tert-butyl 3-(4-amino-3-iodo-1H-pyrazolo[3,4-d]pyrimidin-1-yl)piperidine-1-carboxylate 240 mg of tert-butyl 3-hydroxyazetidine-1-carboxylate was dissolved in 2 ml of chloroform, and 290 µl of triethylamine and 130 µl of methanesulfonyl chloride were added thereto at 0° C. After the mixture was stirred for 1 hour under ice cooling, chloroform and water were added thereto, and an organic layer was separated. The organic layer was washed with a saturated solution of sodium hydrogen carbonate and water and then dried over anhydrous sodium sulfate, and the solvent was distilled off under reduced pressure. 300 mg of 3-iodo-1H-pyrazolo[3,4-d]pyrimidin-4-amine synthesized by the method described in WO 2007/126841, 570 mg of potassium carbonate, and 3 ml of DMA were added to the residue, and the mixture was heated to 100° C. and stirred for 11 hours. The mixture was cooled to room temperature, and was extracted with ethyl acetate. The organic layer was washed with water and dried over anhydrous magnesium sulfate. The residue was purified by amine gel chromatography (hexane/ethyl acetate=1:1→0:1), and thus 232 mg of the title compound was obtained as a pale yellow solid. Physical property value: m/z [M+H]⁺ 417.1

(Step 2) Synthesis of 4-amino-1-(1-(tert-butyloxycarbonyl)azetidin-3-yl)-1H-pyrazolo[3,4-d]pyrimidine-3-carboxylic acid 262 mg of tert-butyl 3-(4-amino-3-iodo-1H-pyrazolo[3,4-d]pyrimidin-1-yl)piperidine-1-carboxylate obtained in Step 1 was dissolved in 10 ml of methanol and 1 ml of triethylamine. After the atmosphere was changed to a carbon monoxide atmosphere, 51 mg of 1,1'-bis(diphenylphosphino)ferrocene-palladium(II) dichloride-dichloromethane was added thereto, and the mixture was heated to 80° C. for 14 hours. After the mixture was cooled, the solvent was removed from the solution, 1 ml of 1,4-dioxane was added to the residue, and 500 µl of a 5 N aqueous solution of NaOH was further added thereto. The mixture was stirred for 3 hours at room temperature, and then the mixture was adjusted to pH 4 with 2 N hydrochloric acid. The mixture was ice-cooled, and a solid precipitated by adding water thereto was collected by filtration and dried. Thus, 42 mg of the title compound was obtained as a pale brown solid. Physical property value: m/z [M+H]⁺ 335.2

(Step 3) Synthesis of tert-butyl-3-(4-amino-3-((5-chlorobenzo[d]oxazol-2-yl)carbamoyl)-1H-pyrazolo[3,4-d]pyrimidin-1-yl)azetidine-1-carboxylate 42 mg of 4-amino-1-(1-(tert-butyloxycarbonyl)azetidin-3-yl)-1H-pyrazolo[3,4-d]pyrimidine-3-carboxylic acid obtained in the above Step 2 was dissolved in 3 ml of DMF, 24 mg of CDI was added thereto, and the mixture was stirred overnight at room temperature. 4 mg of CDI was further added thereto, and the mixture was stirred for 30 minutes. 42 mg of 5-chlorobenzo[d]oxazol-2-amine was added to the solution, the mixture was ice-cooled, and 10 mg of sodium hydride (60%) was added thereto. After the mixture was stirred for 1 hour, the reaction was terminated with water, and the solvent was removed. The residue was purified by reverse phase preparative HPLC purification (water/acetonitrile (0.1% formic acid)), and thus 34 mg of the title compound was obtained as a white solid. Physical property value: m/z [M+H]% 485.2

(Step 4) Synthesis of Example Compound 45

To 10 mg of tert-butyl-3-(4-amino-3-((5-chlorobenzo[d]oxazol-2-yl)carbamoyl)-1H-pyrazolo[3,4-d]pyrimidin-1-yl)azetidine-1-carboxylate obtained in the above Step 3, 1 ml of 4 N hydrochloric acid/1,4-dioxane was added, and the mixture was stirred for 1 hour. Thereafter, the solvent was removed, and the residue was azeotropically distilled with 1 ml of toluene. 1 ml of chloroform and 14 µl of triethylamine were added to the residue, and the mixture was stirred under ice cooling. 1.7 µl of acryloyl chloride was added to the solution, and the mixture was stirred for 1 hour. Subsequently, the reaction was terminated with a saturated aqueous solution of sodium bicarbonate, and extracted with chloroform. The organic layer was dried over sodium sulfate, and then a residue obtained after removal of the solvent was purified by reverse phase preparative HPLC purification (water/acetonitrile (0.1% formic acid)). Thus, 0.69 mg of the title compound was obtained as a white solid.

Example 46

Synthesis of 7-(1-acryloylazetidin-3-yl)-4-amino-N-(5-chlorobenzo[d]oxazol-2-yl)-7H-pyrrolo[2,3-d]pyrimidine-5-carboxamide (Example Compound 46)

(Step 1) Synthesis of tert-butyl 3-(4-chloro-5-iodo-7H-pyrrolo[2,3-d]pyrimidin-7-yl)azetidine-1-carboxylate

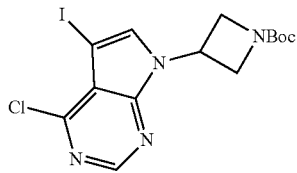 [SMILES: CC(C)(C)OC(=O)N1CC(n2cc(I)c3c(Cl)ncnc32)C1]

2.3 ml of DEAD was added to 80 ml of a tetrahydrofuran solution of 2.00 g of 4-chloro-5-iodo-7H-pyrrolo[2,3-d]pyrimidine, 1.86 g of N-Boc-3-hydroxyazetidine and 3.75 g of triphenylphosphine, and the reaction liquid was stirred for 1 hour. The reaction liquid was concentrated and washed with ethyl acetate, and thus 2.55 g of the title compound as a white solid was obtained. Physical property value: m/z [M+H]+ 435.0

(Step 2) Synthesis of tert-butyl 3-(4-amino-5-iodo-7H-pyrrolo[2,3-d]pyrimidin-7-yl)azetidine-1-carboxylate

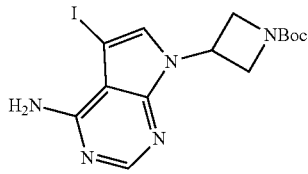 [SMILES: CC(C)(C)OC(=O)N1CC(n2cc(I)c3c(N)ncnc32)C1]

To 1.5 g of tert-butyl 3-(4-chloro-5-iodo-7H-pyrrolo[2,3-d]pyrimidin-7-yl)azetidine-1-carboxylate obtained in the above Step 1, 6 ml of tetrahydrofuran and 6 ml of 28% aqueous ammonia were added, and the reaction mixture was stirred for 1.5 hours at 100° C. in a microwave reaction apparatus. Chloroform and water were added thereto, and an organic layer was separated. The organic layer was dried over anhydrous sodium sulfate, and the solvent was distilled off under reduced pressure. Thus, 1.5 g of the title compound was obtained as a white solid. Physical property value: m/z [M+H]+ 416.0

(Step 3) Synthesis of tert-butyl 3-(4-amino-5-((5-chlorobenzo[d]oxazol-2-yl)carbamoyl)-7H-pyrrolo[2,3-d]pyrimidin-7-yl)azetidine-1-carboxylate 32 mg of tert-butyl 3-(4-amino-5-iodo-7H-pyrrolo[2,3-d]pyrimidin-7-yl)azetidine-1-carboxylate obtained in the above Step 2, 20 mg of 5-chlorobenzo[d]oxazol-2-amine, and 28 μl of diazabicycloundecene were dissolved in 1 ml of DMF, and 9 mg of 1,1'-bis(diphenylphosphino)ferrocene-palladium(II) dichloride-dichloromethane was further added thereto. The mixture was stirred for 1.5 hours at 80° C. in a carbon monoxide atmosphere. The mixture was partitioned with chloroform and water, and the organic layer was dried over sodium sulfate. Subsequently, a residue obtained after removal of the solvent was purified by silica gel chromatography (eluent:hexane/ethyl acetate=1/1→ethyl acetate/methanol=10/1), and thus 20 mg of the title compound was obtained as a pale brown solid. Physical property value: m/z [M+H]+ 484.2

(Step 4) Synthesis of Example Compound 46

To 5 mg of tert-butyl 3-(4-amino-5-((5-chlorobenzo[d]oxazol-2-yl)carbamoyl)-7H-pyrrolo[2,3-d]pyrimidin-7-yl)azetidine-1-carboxylate obtained in the above Step 3, 1 ml of 4 N hydrochloric acid/1,4-dioxane was added, and the mixture was stirred for 1 hour. Thereafter, the solvent was removed, and the residue was azeotropically distilled with 1 ml of toluene. 1 ml of chloroform and 14 μl of triethylamine were added to the residue, and the mixture was stirred under ice cooling. 1.7 μl of acryloyl chloride was added to the solution, and the mixture was stirred for 1 hour. Subsequently, the reaction was terminated with a saturated aqueous solution of sodium bicarbonate, and extracted with chloroform. The organic layer was dried over sodium sulfate, and then a residue obtained after removal of the solvent was purified by reverse phase preparative HPLC purification (water/acetonitrile (0.1% formic acid)). Thus, 2.21 mg of the title compound was obtained as a white solid.

Example 47

Synthesis of (E)-4-amino-N-(5-chlorobenzo[d]oxazol-2-yl)-7-(1-(4-(dimethylamino)but-2-enoyl)azetidin-3-yl) 7H-pyrrolo[2,3-d]pyrimidine-5-carboxamide (Example Compound 47)

To 5 mg of tert-butyl 3-(4-amino-5-((5-chlorobenzo[d]oxazol-2-yl)carbamoyl)-7H-pyrrolo[2,3-d]pyrimidin-7-yl)azetidine-1-carboxylate obtained in Step 3 of Example 46, 1 ml of 4 N hydrochloric acid/1,4-dioxane was added, and the mixture was stirred for 1 hour. Thereafter, the solvent was removed, and the residue was azeotropically distilled with 1 ml of toluene. The residue was dissolved in 1 ml of DMF, 14.4 μl of diisopropylethylamine, 4.1 mg of (E)-4-(dimethylamino)but-2-enoic acid hydrochloride and 9.4 mg of HATU were added thereto. After the mixture was stirred for 1 hour at room temperature, the solution was concentrated under reduced pressure. The residue was purified by reverse phase preparative HPLC purification (water/acetonitrile (0.1% formic acid)), and thus 4.67 mg of the title compound was obtained.

Example 48

Synthesis of (R)-7-(1-acryloylpyrrolidin-3-yl)-4-amino-N-(5-chlorobenzo[d]oxazol-2-yl)-7H-pyrrolo[2,3-d]pyrimidine-5-carboxamide (Example Compound 48)

(Step 1) Synthesis of (R)-tert-butyl 3-(4-chloro-5-iodo-7H-pyrrolo[2,3-d]pyrimidin-7-yl)pyrrolidine-1-carboxylate 5.00 g of 4-chloro-5-iodo-7H-pyrrolo[2,3-d]pyrimidine synthesized by the method described in WO 2005/042556, 19.1 g of (S)-tert-butyl 3-(methylsulfonyloxy)pyrrolidine-1-carboxylate, and 23.5 g of cesium carbonate were suspended in 25 ml of acetonitrile, and the mixture was heated for 3 hours at 60° C. After the suspension was cooled, water and methanol were added thereto, and a solid thus obtained was collected by filtration and dried. Thus, 5.65 g of the title compound was obtained as a pale brown solid.

(Step 2) (R)-tert-butyl 3-(4-amino-5-iodo-7H-pyrrolo[2,3-d]pyrimidin-7-yl)pyrrolidine-1-carboxylate To 5 g of (R)-tert-butyl 3-(4-chloro-5-iodo-7H-pyrrolo[2,3-d]pyrimidin-7-yl)pyrrolidine-1-carboxylate obtained in the above Step 1, 40 ml of 28% aqueous ammonia was added, and the reaction liquid was stirred for 1.5 hours at 100° C. in a microwave reaction apparatus. The mixture was stirred for 1 hour under ice cooling, and a solid precipitated therefrom was collected by filtration and washed with cold methanol. Thus, 3.91 g of the title compound was obtained as a white solid.

(Step 3) Synthesis of (R)-tert-butyl 3-(4-amino-5-((5-chlorobenzo[d]oxazol-2-yl)carbamoyl)-7H-pyrrolo[2,3-d]pyrimidin-7-yl)pyrrolidine-1-carboxylate 93 mg of tert-butyl 3-(4-amino-5-iodo-7H-pyrrolo[2,3-d]pyrimidin-7-yl)pyrrolidine-1-carboxylate obtained in the above Step 2, 110 mg of 5-chlorobenzo[d]oxazol-2-amine, and 100 µl of diazabicycloundecene were dissolved in 2 ml of DMF, and 35 mg of 1,1'-bis(diphenylphosphino)ferrocene-palladium(II) dichloride-dichloromethane was added thereto. The mixture was stirred for 2.5 hours at 80° C. in a carbon monoxide atmosphere. The mixture was partitioned with chloroform and water, and the organic layer was dried over sodium sulfate. Subsequently, a residue obtained after removal of the solvent was purified by silica gel chromatography (eluent:hexane/ethyl acetate=1/1→ethyl acetate/methanol=10/1), and thus 106 mg of the title compound was obtained as a pale brown solid. Physical property value: m/z [M+H]$^+$ 498.1

(Step 4) Synthesis of Example Compound 48

To 20 mg of (R)-tert-butyl 3-(4-amino-5-((5-chlorobenzo[d]oxazol-2-yl)carbamoyl)-7H-pyrrolo[2,3-d]pyrimidin-7-yl)pyrrolidine-1-carboxylate obtained in the above Step 3, 1 ml of 4 N hydrochloric acid/1,4-dioxane was added, and the mixture was stirred for 1 hour. Thereafter, the solvent was removed, and the residue was azeotropically distilled with 1 ml of toluene. 2 ml of chloroform and 28 µl of triethylamine were added to the residue, and the mixture was stirred under ice cooling. 3.2 µl of acryloyl chloride was added to the solution, and the mixture was stirred for 1 hour. Subsequently, the reaction was terminated with a saturated aqueous solution of sodium bicarbonate, and extracted with chloroform. The organic layer was dried over sodium sulfate, and then a residue obtained after removal of the solvent was purified by reverse phase preparative HPLC purification (water/acetonitrile (0.1% formic acid)). Thus, 3.52 mg of the title compound was obtained as a white solid.

Example 49

Synthesis of (R,E)-4-amino-N-(5-chlorobenzo[d]oxazol-2-yl)-7-(1-(4-(dimethylamino)but-2-enoyl)pyrrolidin-3-yl) 7H-pyrrolo[2,3-d]pyrimidine-5-carboxamide (Example Compound 49)

To 13 mg of (R)-tert-butyl 3-(4-amino-5-((5-chlorobenzo[d]oxazol-2-yl)carbamoyl)-7H-pyrrolo[2,3-d]pyrimidin-7-yl)pyrrolidine-1-carboxylate obtained in Step 3 of Example 48, 1 ml of 4 N hydrochloric acid/1,4-dioxane was added, and the mixture was stirred for 1 hour. Thereafter, the solvent was removed, and the residue was azeotropically distilled with 1 ml of toluene. The residue was dissolved in 1 ml of DMF, and 14.4 µl of diisopropylethylamine, 4.1 mg of (E)-4-(dimethylamino)but-2-enoic acid hydrochloride and 9.6 mg of HATU were added thereto. The mixture was stirred for 1 hour at room temperature, and then the solution was concentrated under reduced pressure. The residue was purified by reverse phase preparative HPLC purification (water/acetonitrile (0.1% formic acid)), and thus 6.66 mg of the title compound was obtained.

Example 50

Synthesis of (R,E)-4-amino-N-(5-chlorobenzo[d]oxazol-2-yl)-7-(1-(4-(ethyl(methyl)amino)but-2-enoyl)pyrrolidin-3-yl) 7H-pyrrolo[2,3-d]pyrimidine-5-carboxamide (Example Compound 50)

The title compound was obtained as a white solid according to the procedure described in Example 49, using (E)-4-(ethyl(methyl)amino)but-2-enoic acid hydrochloride instead of (E)-4-(dimethylamino)but-2-enoic acid hydrochloride.

Example 51

Synthesis of (R,E)-4-amino-N-(5-chlorobenzo[d]oxazol-2-yl)-7-(1-(4-(diethylamino)but-2-enoyl)pyrrolidin-3-yl) 7H-pyrrolo[2,3-d]pyrimidine-5-carboxamide (Example Compound 51)

The title compound was obtained as a white solid according to the procedure described in Example 49, using (E)-4-(diethylamino)but-2-enoic acid hydrochloride instead of (E)-4-(dimethylamino)but-2-enoic acid hydrochloride.

Example 52

Synthesis of (R,E)-4-amino-N-(5-chlorobenzo[d]oxazol-2-yl)-7-(1-(4-(isopropyl(methyl)amino)but-2-enoyl)pyrrolidin-3-yl) 7H-pyrrolo[2,3-d]pyrimidine-5-carboxamide (Example Compound 52)

The title compound was obtained as a white solid according to the procedure described in Example 49, using (E)-4-(isopropyl(methyl)amino)but-2-enoic acid hydrochloride instead of (E)-4-(dimethylamino)but-2-enoic acid hydrochloride.

Example 53

Synthesis of (R,E)-4-amino-N-(5-chlorobenzo[d]oxazol-2-yl)-7-(1-(4-(pyrrolidin-1-yl)but-2-enoyl)pyrrolidin-3-yl) 7H-pyrrolo[2,3-d]pyrimidine-5-carboxamide (Example Compound 53)

The title compound was obtained as a white solid according to the procedure described in Example 49, using (E)-4-(pyrrolidin-1-yl)but-2-enoic acid hydrochloride instead of (E)-4-(dimethylamino)but-2-enoic acid hydrochloride.

Example 54

Synthesis of (R,E)-4-amino-N-(5-chlorobenzo[d]oxazol-2-yl)-7-(1-(4-(piperidin-1-yl)but-2-enoyl)pyrrolidin-3-yl) 7H-pyrrolo[2,3-d]pyrimidine-5-carboxamide (Example Compound 54)

The title compound was obtained as a white solid according to the procedure described in Example 49, using (E)-4-(piperidin-1-yl)but-2-enoic acid hydrochloride instead of (E)-4-(dimethylamino)but-2-enoic acid hydrochloride.

Example 55

Synthesis of (R)-7-(1-acryloylpyrrolidin-3-yl)-4-amino-N-(5-phenylbenzo[d]oxazol-2-yl)-7H-pyrrolo[2,3-d]pyrimidine-5-carboxamide (Example Compound 55)

(Step 1) Synthesis of (R)-tert-butyl 3-(4-amino-5-((5-phenylbenzo[d]oxazol-2-yl)carbamoyl)-7H-pyrrolo[2,3-d]pyrimidin-7-yl)pyrrolidine-1-carboxylate The title compound was obtained as a brown solid according to the procedure described in Step 3 of Example 48, using 5-phenylbenzo[d]oxazol-2-amine instead of 5-chlorobenzo[d]oxazol-2-amine. Physical property value: m/z [M+H]$^+$ 540.3

(Step 2) Synthesis of Example Compound 55

The title compound was obtained as a white solid according to the procedure described in Step 4 of Example 48, using (R)-tert-butyl 3-(4-amino-5-((5-phenylbenzo[d]oxazol-2-yl)carbamoyl)-7H-pyrrolo[2,3-d]pyrimidin-7-yl)pyrrolidine-1-carboxylate obtained in the above Step 1.

Example 56

Synthesis of (R,E)-4-amino-N-(5-phenylbenzo[d]oxazol-2-yl)-7-(1-(4-(dimethylamino)but-2-enoyl)pyrrolidin-3-yl) 7H-pyrrolo[2,3-d]pyrimidine-5-carboxamide (Example Compound 56)

To 13 mg of (R)-tert-butyl 3-(4-amino-5-((5-phenylbenzo[d]oxazol-2-yl)carbamoyl)-7H-pyrrolo[2,3-d]pyrimidin-7-yl)pyrrolidine-1-carboxylate obtained in Step 1 of Example 55, 1 ml of 4 N hydrochloric acid/1,4-dioxane was added, and the mixture was stirred for 1 hour. Thereafter, the solvent was removed, and the residue was azeotropically distilled with 1 ml of toluene. The residue was dissolved in 1 ml of DMF, and 14.4 µl of diisopropylethylamine, 4.1 mg of (E)-4-(dimethylamino)but-2-enoic acid hydrochloride, and 9.6 mg of HATU were added thereto. After the mixture was stirred for 1 hour at room temperature, the solution was concentrated under reduced pressure. The residue was purified by reverse phase preparative HPLC purification (water/acetonitrile (0.1% formic acid)), and thus 6.66 mg of the title compound was obtained.

Example 57

Synthesis of (R,E)-4-amino-N-(5-phenylbenzo[d]oxazol-2-yl)-7-(1-(4-(ethyl(methyl)amino)but-2-enoyl)pyrrolidin-3-yl) 7H-pyrrolo[2,3-d]pyrimidine-5-carboxamide (Example Compound 57)

The title compound was obtained as a white solid according to the procedure described in Example 56, using (E)-4-(ethyl(methyl)amino)but-2-enoic acid hydrochloride instead of (E)-4-(dimethylamino)but-2-enoic acid hydrochloride.

Example 58

Synthesis of (R,E)-4-amino-N-(5-phenylbenzo[d]oxazol-2-yl)-7-(1-(4-(diethylamino)but-2-enoyl)pyrrolidin-3-yl) 7H-pyrrolo[2,3-d]pyrimidine-5-carboxamide (Example Compound 58)

The title compound was obtained as a white solid according to the procedure described in Example 56, using (E)-4-(diethylamino)but-2-enoic acid hydrochloride instead of (E)-4-(dimethylamino)but-2-enoic acid hydrochloride.

Example 59

Synthesis of (R,E)-4-amino-N-(5-phenylbenzo[d]oxazol-2-yl)-7-(1-(4-(isopropyl(methyl)amino)but-2-enoyl)pyrrolidin-3-yl) 7H-pyrrolo[2,3-d]pyrimidine-5-carboxamide (Example Compound 59)

The title compound was obtained as a white solid according to the procedure described in Example 56, using (E)-4-(isopropyl(methyl)amino)but-2-enoic acid hydrochloride instead of (E)-4-(dimethylamino)but-2-enoic acid hydrochloride.

Example 60

Synthesis of (R,E)-4-amino-N-(5-phenylbenzo[d]oxazol-2-yl)-7-(1-(4-(pyrrolidin-1-yl)but-2-enoyl)pyrrolidin-3-yl) 7H-pyrrolo[2,3-d]pyrimidine-5-carboxamide (Example Compound 60)

The title compound was obtained as a white solid according to the procedure described in Example 56, using (E)-4-(pyrrolidin-1-yl)but-2-enoic acid hydrochloride instead of (E)-4-(dimethylamino)but-2-enoic acid hydrochloride.

Example 61

Synthesis of (R,E)-4-amino-N-(5-phenylbenzo[d]oxazol-2-yl)-7-(1-(4-(piperidin-1-yl)but-2-enoyl)pyrrolidin-3-yl) 7H-pyrrolo[2,3-d]pyrimidine-5-carboxamide (Example Compound 61)

The title compound was obtained as a white solid according to the procedure described in Example 56, using (E)-4-(piperidin-1-yl)but-2-enoic acid hydrochloride instead of (E)-4-(dimethylamino)but-2-enoic acid hydrochloride.

Example 62

Synthesis of (R,E)-7-(3-((2-(4-(4-(3-(4-amino-3-(benzo[d]oxazol-2-ylcarbamoyl)-1H-pyrazolo[3,4-d]pyrimidin-1-yl)piperidin-1-yl)-4-oxobut-2-en-1-yl)piperazin-1-yl)ethyl)amino)-3-oxopropyl) 5,5-difluoro-1,3-dimethyl-5H-dipyrrolo[1,2-c:2',1'-f][1,3,2]diazaborinin-4-ium-5-uide (Example Compound P-1)

(Step 1) Synthesis of (E)-4-(4-(2-((tert-butoxycarbonyl)amino)ethyl)piperazin-1-yl)but-2-enoic acid 2 g of tert-butyl-(2-(piperazin)-1-yl)ethyl)carbamate was dissolved in 20 ml of DMSO, and 1.35 ml of triethylamine was added thereto. To that solution, (E)-methyl 4-bromobut-2-enoate was added in a total amount of 1.14 ml at room temperature. After the mixture was stirred for 1.5 hours, the solution was added to a saturated aqueous solution of sodium bicarbonate, and extracted with ethyl acetate. The extract was dried over sodium sulfate, subsequently the solvent was removed, and the residue was purified by silica gel chromatography (eluant:chloroform:methanol). 10 ml of triethylamine and 10 ml of water were added to the product obtained, and the mixture was stirred overnight at 100° C. The solvent was removed from the reaction solution, and 2.05 g of the title compound was obtained as an orange-colored amorphous material.

(Step 2) Synthesis of (R,E)-tert-butyl(2-(4-(4-(3-(4-amino-3-(benzo[d]oxazol-2-ylcarbamoyl)-1H-pyrazolo[3,4-d]pyrimidin-1-yl)piperidin-1-yl)-4-oxobut-2-en-1-yl)piperazin-1-yl)ethyl)carbamate 200 mg of (R)-tert-butyl-3-(4-amino-3-((benzo[d]oxazol-2-yl)carbamoyl)-1H-pyrazolo[3,4-d]pyrimidin-1-yl)piperidine-1-carboxylate obtained in Step 1 of Example 13 was dissolved in 3 ml of chloroform, and 1 ml of trifluoroacetic acid was added thereto at room temperature. After 1 hour, the solvent was removed, the residue was dissolved in acetonitrile, and triethylamine was added thereto. Thereafter, the solvent was removed, the residue was dissolved again in chloroform/methanol, and the solvent was removed. The residue was dissolved in 5 ml of DMF, and 176 mg of (E)-4-(4-(2((tert-butoxycarbonyl)amino)ethyl)piperazin-1-yl)but-2-enoic acid obtained in the above Step 1 was added thereto. 104 mg of WSC was added thereto, and the mixture was stirred. After 2 hours, ethyl acetate was added thereto, and an organic layer was washed with a saturated aqueous solution of ammonium chloride. The organic layer was dried over sodium sulfate, subsequently the solvent was removed, and the residue was purified by silica gel chromatography (eluant:chloroform:methanol). Thus, 128.4 mg of the title compound was obtained.

(Step 3) Synthesis of (R,E)-4-amino-1-(1-(4-(4-(2-aminoethyl)piperazin-1-yl)but-2-enoyl)piperidin-3-yl)-N-(benzo[d]oxazol-2-ylcarbamoyl)-1H-pyrazolo[3,4-d]pyrimidine-3-carboxamide 128 mg of (R,E)-tert-butyl(2-(4-(4-(3-(4-amino-3-(benzo[d]oxazol-2-ylcarbamoyl)-1H-pyrazolo[3,4-d]pyrimidin-1-yl)piperidin-1-yl)-4-oxobut-2-en-1-yl)piperazin-1-yl)ethyl)carbamate obtained in the above Step 2 was dissolved in 2 ml of chloroform, and 1 ml of trifluoroacetic acid was added thereto. After 10 minutes, the reaction solution was concentrated and dissolved in acetonitrile. Triethylamine was added thereto, and the mixture was concentrated again. The residue was purified by amine gel chromatography (eluant: chloroform:methanol), and 98.1 mg of the title compound was obtained.

(Step 4) Synthesis of Example Compound P-1

93 mg of (R,E)-4-amino-1-(1-(4-(4-(2-aminoethyl)piperazin-1-yl)but-2-enoyl)piperidin-3-yl)-N-(benzo[d]oxazol-2-ylcarbamoyl)-1H-pyrazolo[3,4-d]pyrimidine-3-carboxamide obtained in the above Step 3 was dissolved in 10 ml of chloroform, and 73 mg of 7-(2-carboxyethyl)-5,5-difluoro-1,3-dimethyl-5H-dipyrrolo[1,2-c:2',1'-f][1,3,2]diazaborinin-4-ium-5-uide, 22 mg of HOBt and 48 mg of WSC were added thereto. After the mixture was stirred for 2 hours, the reaction solution was partitioned with chloroform and a saturated aqueous solution of sodium bicarbonate. The organic layer was dried over sodium sulfate and then concentrated, and the residue was purified by amine gel chromatography (eluant: chloroform:methanol). 98.1 mg of the title compound was obtained.

Example 63

Synthesis of 4-amino-N-(benzo[d]oxazol-2-yl)-1-((R)-1-((E)-4-(4-(2-(5-((3aS,4S,6aR)-2-oxohexahydro-1H-thieno[3,4-d]imidazol-4-yl)pentanamido)ethyl)piperazin-1-yl)but-2-enoyl)piperidin-3-yl)-1H-pyrazolo[3,4-d]pyrimidine-3-carboxamide (Example Compound P-2)

To a solution of 3 mg of (R,E)-4-amino-1-(1-(4-(4-(2-aminoethyl)piperazin-1-yl)but-2-enoyl)piperidin-3-yl)-N-(benzo[d]oxazol-2-ylcarbamoyl)-1H-pyrazolo[3,4-d]pyrimidine-3-carboxamide obtained in Step 3 of Example 62 in 0.5 ml of DMF, 1.5 mg of BIOTIN-NHS (registered trademark) and 4 µl of triethylamine were added, and the mixture was stirred overnight. 0.5 ml of DMSO was added to the solution, and the mixture was purified by reverse phase preparative HPLC purification (water/acetonitrile (0.1% formic acid)). Thus, 1.0 mg of the title compound was obtained as a white solid.

Example 64

Synthesis of (R)-1-(1-acryloylpiperidin-3-yl)-4-amino-N-(7-chlorobenzo[d]oxazol-2-yl)-1H-pyrazolo[3,4-d]pyrimidine-3-carboxamide (Example Compound 64)

(Step 1) Synthesis of (R)-1-(1-acryloylpiperidin-3-yl)-4-amino-1H-pyrazolo[3,4-d]pyrimidine-3-carboxylic acid To 10 g of (R)-4-amino-1-(1-(tert-butyloxycarbonyl)piperidin-3-yl)-1H-pyrazolo[3,4-d]pyrimidine-3-carboxylic acid obtained in Synthetic Example 2, 50 mL of 4 N hydrochloric acid/1,4-dioxane was added. After the mixture was stirred for 1 hour, the solvent was removed using an evaporator. 140 mL of chloroform and 25 mL of triethylamine were added to the residue, and after the mixture was ice-cooled, 2.23 mL of acryloyl chloride was added thereto. The mixture was stirred for 1.5 hours, and then the solvent was removed using an evaporator. An aqueous solution of formic acid at pH 3.0 was added to the residue, and the mixture was stirred for 2 hours. Subsequently, a precipitate was collected by filtration, and was dried under reduced pressure. Thus, 8.93 g of the title compound was obtained as a whitish brown solid.

(Step 2) Synthesis of (R)-1-(1-acryloylpiperidin-3-yl)-4-amino-N-(7-chlorobenzo[d]oxazol-2-yl)-1H-pyrazolo[3,4-d]pyrimidine-3-carboxamide 5 mg of (R)-1-(1-acryloylpiperidin-3-yl)-4-amino-1H-pyrazolo[3,4-d]pyrimidine-3-carboxylic acid obtained in Step 1 was dissolved in 150 µL of DMF, and then 8.2 µL of diisopropylethylamine, 4.0 mg of 7-chlorobenzo[d]oxazol-2-amine and 9.0 mg of HATU were added. The mixture was stirred for 1 hour. 850 µL of DMSO was added to the reaction solution, and the mixture was purified by reverse phase preparative HPLC purification (water/acetonitrile (0.1% formic acid)). Thus, 0.36 mg of the title compound was obtained as a white solid.

Example 65

Synthesis of (S)-1-(1-acryloylpyrrolidin-3-yl)-4-amino-N-(benzo[d]oxazol-2-yl)-1H-pyrazolo[3,4-d]pyrimidine-3-carboxamide (Example Compound 65)

(Step 1) Synthesis of (R)-tert-butyl 3-(methylsulfonyloxy)pyrrolidine-1-carboxylate The title compound as an oily compound was obtained from (R)—N—Boc-3-pyrrolidinol according to the procedure described in Synthetic Example 3.

(Step 2) Synthesis of (S)-tert-butyl 3-(4-amino-3-iodo-1H-pyrazolo[3,4-d]pyrimidin-1-yl)pyrrolidine-1-carboxylate The title compound was obtained as a pale yellow solid from 3-iodo-1H-pyrazolo[3,4-d]pyrimidin-4-amine and (R)-tert-butyl 3-(methylsulfonyloxy)pyrrolidine-1-carboxylate according to the procedure described in Synthetic Example 3 (Step 2).

(Step 3) Synthesis of (S)-1-(3-(4-amino-3-iodo-1H-pyrazolo[3,4-d]pyrimidin-1-yl)pyrrolidin-1-yl)prop-2-en-1-one To 500 mg of (S)-tert-butyl 3-(4-amino-3-iodo-1H-pyrazolo[3,4-d]pyrimidin-1-yl)pyrrolidine-1-carboxylate obtained in Step 2, 5 mL of chloroform and 1.7 ml of trifluoroacetic acid were added. After the mixture was stirred for 1 hour, the solvent was removed using an evaporator. 12 mL of chloroform and 810 μL of triethylamine were added to the residue, and after the mixture was ice-cooled, 89 μL of acryloyl chloride was added thereto. After the mixture was stirred for 30 minutes, the reaction was terminated with a saturated aqueous solution of sodium bicarbonate, and extracted with chloroform. The organic layer was dried over sodium sulfate, and then a residue obtained after removal of the solvent was purified using silica gel column (eluant:ethyl acetate:methanol). Thus, 350 mg of the title compound was obtained as a white solid.

(Step 4) Synthesis of (S)-1-(1-acryloylpyrrolidin-3-yl)-4-amino-N-(benzo[d]oxazol-2-yl)-1H-pyrazolo[3,4-d]pyrimidine-3-carboxamide 20 mg of (S)-1-(3-(4-amino-3-iodo-1H-pyrazolo[3,4-d]pyrimidin-1-yl) pyrrolidin-1-yl)prop-2-en-1-one obtained in Step 3 was dissolved in 520 mL of DMF, and 13 mg of benzo[d]oxazol-2-amine, 3.65 mg of PdCl$_2$(PPh3)$_2$ and 23 μL of DBU were added thereto. The mixture was stirred for 2 hours at 120 degrees in a carbon monoxide atmosphere, and then the solvent was removed using an evaporator. DMSO was added to the residue, and the mixture was purified by reverse phase preparative HPLC purification (water/acetonitrile (0.1% formic acid)), and thus 1.9 mg of the title compound was obtained as a white solid.

Example 66

Synthesis of 1-((1-acryloylpyrrolidin-3-yl)methyl)-4-amino-N-(benzo[d]oxazol-2-yl)-1H-pyrazolo[3,4-d]pyrimidine-3-carboxamide (Example Compound 66)

(Step 1) Synthesis of tert-butyl 3-((4-amino-3-iodo-1H-pyrazolo[3,4-d]pyrimidin-1-yl)methyl)pyrrolidine-1-carboxylate 464 mg of the title compound was obtained as a pale yellow solid from 300 mg of 3-iodo-1H-pyrazolo[3,4-d]pyrimidin-4-amine and 396 mg of tert-butyl 3-(bromomethyl)pyrrolidine-1-carboxylate according to the procedure described in Synthetic Example 3 (Step 2).

(Step 2) Synthesis of 1-(3-((4-amino-3-iodo-1H-pyrazolo[3,4-d]pyrimidin-1-yl)methyl)pyrrolidin-1-yl)prop-2-en-1-one 274 mg of the title compound was obtained as a pale yellow solid according to the procedure described in Step 3 of Example 65, from 464 mg of tert-butyl 3-((4-amino-3-iodo-1H-pyrazolo[3,4-d]pyrimidin-1-yl)methyl)pyrrolidine-1-carboxylate obtained in Step 1.

(Step 3) Synthesis of 1-((1-acryloylpyrrolidin-3-yl)methyl)-4-amino-N-(benzo[d]oxazol-2-yl)-1H-pyrazolo[3,4-d]pyrimidine-3-carboxamide 3.2 mg of the title compound was obtained as a white solid according to the procedure described in Step 4 of Example 65, from 10 mg of 1-(3-((4-amino-3-iodo-1H-pyrazolo[3,4-d]pyrimidin-1-yl)methyl)pyrrolidin-1-yl)prop-2-en-1-one obtained in Step 2.

Example 67

Synthesis of 1-((1-acryloylpiperidin-3-yl)methyl)-4-amino-N-(benzo[d]oxazol-2-yl)-1H-pyrazolo[3,4-d]pyrimidine-3-carboxamide (Example Compound 67)

(Step 1) Synthesis of tert-butyl 3-((4-amino-3-iodo-1H-pyrazolo[3,4-d]pyrimidin-1-yl)methyl)piperidine-1-carboxylate 375 mg of the title compound was obtained as a pale yellow solid from 300 mg of 3-iodo-1H-pyrazolo[3,4-d]pyrimidin-4-amine and 416 mg of tert-butyl 3-(bromomethyl)pyrrolidine-1-carboxylate according to the procedure described in Synthetic Example 3 (Step 2).

(Step 2) Synthesis of 1-(3-((4-amino-3-iodo-1H-pyrazolo[3,4-d]pyrimidin-1-yl)methyl)piperidin-1-yl)prop-2-en-1-one 228 mg of the title compound was obtained as a pale yellow solid according to the procedure described in Step 3 of Example 65, from 375 g of tert-butyl-3-((4-amino-3-iodo-1H-pyrazolo[3,4-d]pyrimidin-1-yl)methyl)piperidine-1-carboxylate obtained in Step 1.

(Step 3) Synthesis of 1-((1-acryloylpiperidin-3-yl)methyl)-4-amino-N-(benzo[d]oxazol-2-yl)-1H-pyrazolo[3,4-d]pyrimidine-3-carboxamide 1.4 mg of the title compound was obtained as a white solid according to the procedure described in Step 4 of Example 65, from 10 mg of 1-(3-((4-amino-3-iodo-1H-pyrazolo[3,4-d]pyrimidin-1-yl)methyl)piperidin-1-yl)prop-2-en-1-one obtained in Step 2.

Example 68

Synthesis of 1-((1-acryloylpiperidin-4-yl)methyl)-4-amino-N-(benzo[d]oxazol-2-yl)-1H-pyrazolo[3,4-d]pyrimidine-3-carboxamide (Example Compound 68)

(Step 1) Synthesis of tert-butyl 4-((4-amino-3-iodo-1H-pyrazolo[3,4-d]pyrimidin-1-yl)methyl)piperidine-1-carboxylate 120 mg of the title compound was obtained as a pale yellow solid from 100 mg of 3-iodo-1H-pyrazolo[3,4-d]pyrimidin-4-amine and 130 mg of tert-butyl 4-(bromomethyl)piperidine-1-carboxylate according to the procedure described in Synthetic Example 3 (Step 2).

(Step 2) Synthesis of 1-(4-((4-amino-3-iodo-1H-pyrazolo[3,4-d]pyrimidin-1-yl)methyl)piperidin-1-yl)prop-2-en-1-one 85 mg of the title compound was obtained as a pale yellow solid according to the procedure described in Step 3 of Example 65, from 120 mg of tert-butyl 4-((4-amino-3-iodo-1H-pyrazolo[3,4-d]pyrimidin-1-yl)methyl)piperidine-1-carboxylate obtained in Step 1.

(Step 3) Synthesis of 1-((1-acryloylpiperidin-4-yl)methyl)-4-amino-N-(benzo[d]oxazol-2-yl)-1H-pyrazolo[3,4-d]pyrimidine-3-carboxamide 3.12 mg of the title compound was obtained as a white solid according to the procedure described in Step 4 of Example 65, from 10 mg of 1-(4-((4-amino-3-iodo-1H-pyrazolo[3,4-d]pyrimidin-1-yl)methyl)piperidin-1-yl)prop-2-en-1-one obtained in Step 2.

Example 69

Synthesis of 1-(1-acryloylpiperidin-4-yl)-4-amino-N-(benzo[d]oxazol-2-yl)-1H-pyrazolo[3,4-d]pyrimidine-3-carboxamide (Example Compound 69)

(Step 1) Synthesis of tert-butyl 4-(4-amino-3-iodo-1H-pyrazolo[3,4-d]pyrimidin-1-yl)piperidine-1-carboxylate The title compound was obtained as a pale yellow solid from 3-iodo-1H-pyrazolo[3,4-d]pyrimidin-4-amine and tert-butyl 4-bromopiperidine-1-carboxylate according to the procedure described in Synthetic Example 3 (Step 2).

(Step 2) Synthesis of 1-(4-(4-amino-3-iodo-1H-pyrazolo[3,4-d]pyrimidin-1-yl)piperidin-1-yl)prop-2-en-1-one The title compound was obtained as a pale yellow solid according to the procedure described in Step 3 of Example 65, from tert-butyl 4-(4-amino-3-iodo-1H-pyrazolo[3,4-d]pyrimidin-1-yl)piperidine-1-carboxylate obtained in Step 1.

(Step 3) Synthesis of 1-(1-acryloylpiperidin-4-yl)-4-amino-N-(benzo[d]oxazol-2-yl)-1H-pyrazolo[3,4-d]pyrimidine-3-carboxamide 2.4 mg of the title compound was obtained as a white solid according to the procedure described in Step 4 of Example 65, from 10 mg of 1-(4-(4-amino-3-iodo-1H-pyrazolo[3,4-d]pyrimidin-1-yl)piperidin-1-yl)prop-2-en-1-one obtained in Step 3.

Example 70

Synthesis of 1-((1-acryloylazetidin-3-yl)methyl)-4-amino-N-(benzo[d]oxazol-2-yl)-1H-pyrazolo[3,4-d]pyrimidine-3-carboxamide (Example Compound 70)

(Step 1) Synthesis of tert-butyl 3-((methylsulfonyloxy)methyl)azetidine-1-carboxylate The title compound was obtained as an oily compound from tert-butyl 3-(hydroxymethyl)azetidine-1-carboxylate according to the procedure described in Synthetic Example 3.

(Step 2) Synthesis of tert-butyl 3-((4-amino-3-iodo-1H-pyrazolo[3,4-d]pyrimidin-1-yl)methyl)azetidine-1-carboxylate The title compound was obtained as a pale yellow solid according to the procedure described in Synthetic Example 3 (Step 2) from 200 mg of 3-iodo-1H-pyrazolo[3,4-d]pyrimidin-4-amine and tert-butyl 3-((methylsulfonyloxy)methyl)azetidine-1-carboxylate obtained in Step 1.

(Step 3) Synthesis of 1-(3-((4-amino-3-iodo-1H-pyrazolo[3,4-d]pyrimidin-1-yl)methyl)azetidin-1-yl)propyl-2-en-1-one The title compound was obtained as a pale yellow solid according to the procedure described in Step 3 of Example 65, from tert-butyl 3-((4-amino-3-iodo-1H-pyrazolo[3,4-d]pyrimidin-1-yl)methyl)azetidine-1-carboxylate obtained in Step 2.

(Step 4) Synthesis of 1-((1-acryloylazetidin-3-yl)methyl)-4-amino-N-(benzo[d]oxazol-2-yl)-1H-pyrazolo[3,4-d]pyrimidine-3-carboxamide 2.44 mg of the title compound was obtained as a white solid according to the procedure described in Step 4 of Example 65, from 10 mg of 1-(3-((4-amino-3-iodo-1H-pyrazolo[3,4-d]pyrimidin-1-yl)methyl)azetidin-1-yl)propyl-2-en-1-one obtained in Step 3.

Example 71

Synthesis of 1-((1S,4S)-4-acrylamidocyclohexyl)-4-amino-N-(benzo[d]oxazol-2-yl)-1H-pyrazolo[3,4-d]pyrimidine-3-carboxamide (Example Compound 71)

(Step 1) Synthesis of (1R,4R)-4-((tert-butoxycarbonyl)amino)cyclohexylmethanesulfonate 780 mg of the title compound was obtained as an oily compound from 500 mg of tert-butyl(1R,4R)-4-cyclohexylcarbamate according to the procedure described in Synthetic Example 3.

(Step 2) Synthesis of tert-butyl((1S,4S)-4-(4-amino-3-iodo-1H-pyrazolo[3,4-d]pyrimidin-1-yl)cyclohexylcarbammate 614 mg of the title compound was obtained as a pale yellow solid according to the procedure described in Synthetic Example 3 (Step 2) from 630 mg of 3-iodo-1H-pyrazolo[3,4-d]pyrimidin-4-amine and 780 mg of (1R,4R)-4-((tert-butoxycarbonyl)amino)cyclohexylmethanesulfonate obtained in Step 1.

(Step 3) Synthesis of N-((1S,4S)-4-(4-amino-3-iodo-1H-pyrazolo[3,4-d]pyrimidin-1-yl)cyclohexyl)acrylamide 137 mg of the title compound was obtained as a pale yellow solid according to the procedure described in Step 3 of Example 65, from 200 mg of tert-butyl((1S,4S)-4-(4-amino-3-iodo-1H-pyrazolo[3,4-d]pyrimidin-1-yl)cyclohexylcarbammate obtained in Step 2.

(Step 4) Synthesis of 1-((1S,4S)-4-acrylamidocyclohexyl)-4-amino-N-(benzo[d]oxazol-2-yl)-1H-pyrazolo[3,4-d]pyrimidine-3-carboxamide 2.08 mg of the title compound was obtained as a white solid according to the procedure described in Step 4 of Example 65, from 10 mg of N-((1S,4S)-4-(4-amino-3-iodo-1H-pyrazolo[3,4-d]pyrimidin-1-yl)cyclohexyl)acrylamide obtained in Step 3.

Example 72

Synthesis of 1-((1R,4R)-4-acrylamidocyclohexyl)-4-amino-N-(benzo[d]oxazol-2-yl)-1H-pyrazolo[3,4-d]pyrimidine-3-carboxamide (Example Compound 72)

(Step 1) Synthesis of (1S,4S)-4-((tert-butoxycarbonyl)amino)cyclohexylmethanesulfonate 704 mg of the title compound was obtained as an oily compound from 500 mg of tert-butyl(1S,4S)-4-cyclohexylcarbamate according to the procedure described in Synthetic Example 3.

(Step 2) Synthesis of tert-butyl((1R,4R)-4-(4-amino-3-iodo-1H-pyrazolo[3,4-d]pyrimidin-1-yl)cyclohexylcarbammate 375 mg of the title compound was obtained as a pale yellow solid according to the procedure described in Synthetic Example 3 (Step 2) from 570 mg of 3-iodo-1H-pyrazolo[3,4-d]pyrimidin-4-amine and 704 mg of (1S,4S)-4-((tert-butoxycarbonyl)amino)cyclohexylmethanesulfonate obtained in Step 1.

(Step 3) Synthesis of N-((1R,4R)-4-(4-amino-3-iodo-1H-pyrazolo[3,4-d]pyrimidin-1-yl)cyclohexyl)acrylamide 90 mg of the title compound was obtained as a pale yellow solid according to the procedure described in Step 3 of Example 65, from 200 mg of tert-butyl((1R,4R)-4-(4-amino-3-iodo-1H-pyrazolo[3,4-d]pyrimidin-1-yl)cyclohexylcarbammate obtained in Step 2.

(Step 4) Synthesis of 1-((1S,4S)-4-acrylamidocyclohexyl)-4-amino-N-(benzo[d]oxazol-2-yl)-1H-pyrazolo[3,4-d]pyrimidine-3-carboxamide 3.43 mg of the title compound was obtained as a white solid according to the procedure described in Step 4 of Example 65, from 10 mg of N-((1S,4S)-4-(4-amino-3-iodo-1H-pyrazolo[3,4-d]pyrimidin-1-yl)cyclohexyl)acrylamide obtained in Step 3.

Example 73

Synthesis of (S,E)-4-amino-N-(benzo[d]oxazol-2-yl)-1-(1-(4-(dimethylamino)but-2-enoyl)pyrrolidin-3-yl)-1H-pyrazolo[3,4-d]pyrimidine-3-carboxamide (Example Compound 73)

(Step 1) (S)-tert-butyl 3-(4-amino-3-(benzo[d]oxazol-2-ylcarbamoyl)-1H-pyrazolo[3,4-d]pyrimidin-1-yl)pyrrolidine-1-carboxylate The title compound was obtained according to the procedure described in Step 4 of Example 65, from (S)-tert-butyl 3-(4-amino-3-iodo-1H-pyrazolo[3,4-d]pyrimidin-1-yl)pyrrolidine-1-carboxylate obtained in Step 2 of Example 65.

(Step 2) Synthesis of (S,E)-amino-N-(benzo[d]oxazol-2-yl)-1-(1-(4-(dimethylamino)but-2-enoyl)pyrrolidin-3-yl)-1H-pyrazolo[3,4-d]pyrimidine-3-carboxamide 13.8 mg of the title compound was obtained as a white solid according to the procedure described in Example 32, from 20 mg of (S)-tert-butyl 3-(4-amino-3-(benzo[d]oxazol-2-ylcarbamoyl)-1H-pyrazolo[3,4-d]pyrimidin-1-yl)pyrrolidine-1-carboxylate obtained in Step 1.

Example 74

Synthesis of 1-(1-acryloylazetidin-3-yl)-4-amino-N-(benzo[d]oxazol-2-yl)-1H-pyrazolo[3,4-d]pyrimidine-3-carboxamide (Example Compound 74)

(Step 1) Synthesis of tert-butyl 3-(methylsulfonyloxy)azetidine-1-carboxylate 774 mg of the title compound was obtained as an oily compound from 500 mg of tert-butyl 3-hydroxyazetidine-1-carboxylate according to the procedure described in Synthetic Example 3.

(Step 2) Synthesis of tert-butyl 3-(4-amino-3-iodo-1H-pyrazolo[3,4-d]pyrimidin-1-yl)azetidine-1-carboxylate 690 mg of the title compound was obtained as a pale yellow solid according to the procedure described in Synthetic Example 3 (Step 2) from 670 mg of 3-iodo-1H-pyrazolo[3,4-d]pyrimidin-4-amine and 774 mg of tert-butyl 3-(methylsulfonyloxy)azetidine-1-carboxylate obtained in Step 1.

(Step 3) Synthesis of 1-(3-(4-amino-3-iodo-1H-pyrazolo[3,4-d]pyrimidin-1-yl)azetidin-1-yl)propyl-2-en-1-one 129 mg of the title compound was obtained as a pale yellow solid according to the procedure described in Step 3 of Example 65, from 200 mg of tert-butyl 3-(4-amino-3-iodo-1H-pyrazolo[3,4-d]pyrimidin-1-yl)azetidine-1-carboxylate obtained in Step 2.

(Step 4) Synthesis of 1-((1-acryloylazetidin-3-yl)-4-amino-N-(benzo[d]oxazol-2-yl)-1H-pyrazolo[3,4-d]pyrimidine-3-carboxamide The title compound was obtained as a white solid according to the procedure described in Step 4 of Example 65, from 1-(3-(4-amino-3-iodo-1H-pyrazolo[3,4-d]pyrimidin-1-yl)azetidin-1-yl)propyl-2-en-1-one obtained in Step 3.

Example 75

Synthesis of 1-((1-acryloylazetidin-3-yl)methyl)-4-amino-N-(5-fluorobenzo[d]oxazol-2-yl)-1H-pyrazolo[3,4-d]pyrimidine-3-carboxamide (Example Compound 75)

(Step 1) 3.36 mg of the title compound was obtained as a white solid according to the procedure described in Step 4 of Example 65, from 10 mg of 1-(3-((4-amino-3-iodo-1H-pyrazolo[3,4-d]pyrimidin-1-yl)methyl)azetidin-1-yl)propyl-2-en-1-one obtained in Step 3 of Example 70 and 5.2 mg of 5-fluorobenzo[d]oxazol-2-amine.

Example 76

Synthesis of 1-((1-acryloylazetidin-3-yl)methyl)-4-amino-N-(5-chlorobenzo[d]oxazol-2-yl)-1H-pyrazolo[3,4-d]pyrimidine-3-carboxamide (Example Compound 76)

(Step 1) 3.76 mg of the title compound was obtained as a white solid according to the procedure described in Step 4 of Example 65, from 10 mg of 1-(3-((4-amino-3-iodo-1H-pyrazolo[3,4-d]pyrimidin-1-yl)methyl)azetidin-1-yl)propyl-2-en-1-one obtained in Step 3 of Example 70 and 5.2 mg of 5-chlorobenzo[d]oxazol-2-amine.

Example 77

Synthesis of 1-((1-acryloylpiperidin-4-yl)methyl)-4-amino-N-(5-fluorobenzo[d]oxazol-2-yl)-1H-pyrazolo[3,4-d]pyrimidine-3-carboxamide (Example Compound 77)

(Step 1) 6.37 mg of the title compound was obtained as a white solid according to the procedure described in Step 4 of Example 65, from 10 mg of 1-(4-((4-amino-3-iodo-1H-pyrazolo[3,4-d]pyrimidin-1-yl)methyl)piperidin-1-yl)prop-2-en-1-one obtained in Step 2 of Example 68 and 4.8 mg of 5-fluorobenzo[d]oxazol-2-amine.

Example 78

Synthesis of 1-((1S,4S)-4-acrylamidocyclohexyl)-4-amino-N-(5-chlorobenzo[d]oxazol-2-yl)-1H-pyrazolo[3,4-d]pyrimidine-3-carboxamide (Example Compound 78)

(Step 1) 1.93 mg of the title compound was obtained as a white solid according to the procedure described in Step 4 of Example 65, from 10 mg of N-((1S,4S)-4-(4-amino-3-iodo-1H-pyrazolo[3,4-d]pyrimidin-1-yl)cyclohexyl)acrylamide obtained in Step 3 of Example 72 and 5.2 mg of 5-chlorobenzo[d]oxazol-2-amine.

Example 79

Synthesis of 1-(1-acryloylazetidin-3-yl)-4-amino-N-(5-fluorobenzo[d]oxazol-2-yl)-1H-pyrazolo[3,4-d]pyrimidine-3-carboxamide (Example Compound 79)

(Step 1) 2.21 mg of the title compound was obtained as a white solid according to the procedure described in Step 4 of Example 65, from 10 mg of 1-(3-(4-amino-3-iodo-1H-pyrazolo[3,4-d]pyrimidin-1-yl)azetidin-1-yl)propyl-2-en-1-one obtained in Step 3 of Example 74 and 4.8 mg of 5-fluorobenzo[d]oxazol-2-amine.

Example 80

Synthesis of 1-((1-acryloylpiperidin-4-yl)methyl)-4-amino-N-(5-chlorobenzo[d]oxazol-2-yl)-1H-pyrazolo[3,4-d]pyrimidine-3-carboxamide (Example Compound 80)

(Step 1) 4.30 mg of the title compound was obtained as a white solid according to the procedure described in Step 4 of Example 65, from 10 mg of 1-(4-((4-amino-3-iodo-1H-pyrazolo[3,4-d]pyrimidin-1-yl)methyl)piperidin-1-yl)prop-2-en-1-one obtained in Step 2 of Example 68 and 5.2 mg of 5-chlorobenzo[d]oxazol-2-amine.

Example 81

Synthesis of 1-((1S,4S)-4-acrylamidocyclohexyl)-4-amino-N-(5-fluorobenzo[d]oxazol-2-yl)-1H-pyrazolo[3,4-d]pyrimidine-3-carboxamide (Example Compound 81)

(Step 1) 2.91 mg of the title compound was obtained as a white solid according to the procedure described in Step 4 of Example 65, from 10 mg of N-((1S,4S)-4-(4-amino-3-iodo-1H-pyrazolo[3,4-d]pyrimidin-1-yl)cyclohexyl)acrylamide obtained in Step 3 of Example 72 and 4.8 mg of 5-fluorobenzo[d]oxazol-2-amine.

Example 82

Synthesis of 1-(1-acryloylpyrrolidin-3-yl)-4-amino-N-(benzo[d]oxazol-2-yl)-1H-pyrazolo[3,4-d]pyrimidine-3-carboxamide (Example Compound 82)

(Step 1) Synthesis of tert-butyl 3-(methylsulfonyloxy)pyrrolidine-1-carboxylate

The title compound was obtained as an oily compound from N-Boc-3-pyrrolidinol according to the procedure described in Synthetic Example 3.

(Step 2) Synthesis of tert-butyl 3-(4-amino-3-iodo-1H-pyrazolo[3,4-d]pyrimidin-1-yl)pyrrolidine-1-carboxylate The title compound was obtained as a pale yellow solid from 3-(methylsulfonyloxy)pyrrolidine-1-carboxylate according to the procedure described in Example 65 (Step 2).

(Step 3) Synthesis of 1-(3-(4-amino-3-iodo-1H-pyrazolo[3,4-d]pyrimidin-1-yl)pyrrolidin-1-yl)prop-2-en-1-one The title compound was obtained as a white solid according to the procedure described in Step 3 of Example 65, from tert-butyl 3-(4-amino-3-iodo-1H-pyrazolo[3,4-d]pyrimidin-1-yl)pyrrolidine-1-carboxylate obtained in Step 2.

(Step 4) Synthesis of 1-(1-acryloylpyrrolidin-3-yl)-4-amino-N-(benzo[d]oxazol-2-yl)-1H-pyrazolo[3,4-d]pyrimidine-3-carboxamide 3.9 mg of the title compound was obtained as a white solid according to the procedure described in Step 4 of Example 65, from 10 mg of 1-(3-(4-amino-3-iodo-1H-pyrazolo[3,4-d]pyrimidin-1-yl)pyrrolopyrrolidin-1-yl)prop-2-en-1-one obtained in Step 3.

Example 83

Synthesis of 1-(1-acryloylpyrrolidin-3-yl)-4-amino-N-(5-fluorobenzo[d]oxazol-2-yl)-1H-pyrazolo[3,4-d]pyrimidine-3-carboxamide (Example Compound 83)

(Step 1) 4.09 mg of the title compound was obtained as a white solid according to the procedure described in Step 4 of Example 65, from 10 mg of 1-(3-(4-amino-3-iodo-1H-pyrazolo[3,4-d]pyrimidin-1-yl)pyrrolopyrrolidin-1-yl)prop-2-en-1-one obtained in Step 3 of Example 82 and 4.8 mg of 5-fluorobenzo[d]oxazol-2-amine.

Example 84

Synthesis of 1-(1-acryloylpyrrolidin-3-yl)-4-amino-N-(5-chlorobenzo[d]oxazol-2-yl)-1H-pyrazolo[3,4-d]pyrimidine-3-carboxamide (Example Compound 84)

(Step 1) 3.47 mg of the title compound was obtained as a white solid according to the procedure described in Step 4 of Example 65, from 10 mg of 1-(3-(4-amino-3-iodo-1H-pyrazolo[3,4-d]pyrimidin-1-yl)pyrrolopyrrolidin-1-yl)prop-2-en-1-one obtained in Step 3 of Example 82 and 5.2 mg of 5-chlorobenzo[d]oxazol-2-amine.

Example 85

Synthesis of 1-(3-acrylamidopropyl)-4-amino-N-(benzo[d]oxazol-2-yl)-1H-pyrazolo[3,4-d]pyrimidine-3-carboxamide (Example Compound 85)

(Step 1) Synthesis of tert-butyl(3-(4-amino-3-iodo-1H-pyrazolo[3,4-d]pyrimidin-1-yl)propyl)carboxylate 223 mg of the title compound was obtained as a pale yellow solid from 200 mg of 3-iodo-1H-pyrazolo[3,4-d]pyrimidin-4-amine and 273 mg of tert-butyl(3-bromopropyl)carboxylate according to the procedure described in Synthetic Example 3 (Step 2).

(Step 2) N-(3-(4-amino-3-iodo-1H-pyrazolo[3,4-d]pyrimidin-1-yl)propyl)acrylamide 125 mg of the title compound was obtained as a pale yellow solid according to the procedure described in Step 3 of Example 65, from 240 mg of tert-butyl(3-(4-amino-3-iodo-1H-pyrazolo[3,4-d]pyrimidin-1-yl)propyl)carboxylate obtained in Step 1.

(Step 3) Synthesis of 1-(3-acrylamidopropyl)-4-amino-N-(benzo[d]oxazol-2-yl)-1H-pyrazolo[3,4-d]pyrimidine-3-carboxamide 3.2 mg of the title compound was obtained as a white slid according to the procedure described in Step 4 of Example 65, from 10 mg of N-(3-(4-amino-3-iodo-1H-pyrazolo[3,4-d]pyrimidin-1-yl)propyl)acrylamide obtained in Step 3.

Example 86

Synthesis of 1-(2-acrylamidoethyl)-4-amino-N-(benzo[d]oxazol-2-yl)-1H-pyrazolo[3,4-d]pyrimidine-3-carboxamide (Example Compound 86)

(Step 1) Synthesis of tert-butyl(2-(4-amino-3-iodo-1H-pyrazolo[3,4-d]pyrimidin-1-yl)ethyl)carboxylate 239 mg of the title compound was obtained as a pale yellow solid from 200 mg of 3-iodo-1H-pyrazolo[3,4-d]pyrimidin-4-amine and 257 mg of tert-butyl(2-bromoethyl)carboxylate according to the procedure described in Synthetic Example 3 (Step 2).

(Step 2) N-(2-(4-amino-3-iodo-1H-pyrazolo[3,4-d]pyrimidin-1-yl)ethyl)acrylamide 140 mg of the title compound was obtained as a pale yellow solid according to the procedure described in Step 3 of Example 65, from 239 mg of tert-butyl(2-(4-amino-3-iodo-1H-pyrazolo[3,4-d]pyrimidin-1-yl)ethyl)carboxylate obtained in Step 1.

(Step 3) Synthesis of 1-(2-acrylamidoethyl)-4-amino-N-(benzo[d]oxazol-2-yl)-1H-pyrazolo[3,4-d]pyrimidine-3-carboxamide 1.8 mg of the title compound was obtained as a white solid according to the procedure described in Step 4 of Example 65, from 10 mg of N-(2-(4-amino-3-iodo-1H-pyrazolo[3,4-d]pyrimidin-1-yl)ethyl)acrylamide obtained in Step 2.

Reference Example 1

Synthesis of (R)-1-(3-(4-amino-3-(4-phenoxyphenyl)-1H-pyrazolo[3,4-d]pyrimidin-1-yl)piperidin-1-yl)prop-2-en-1-one (Reference compound 1)

The title compound was obtained as a white solid by synthesizing the compound according to the procedure described in the method of WO 2008/121742.

Hereinafter, the structural formulas and physical property values of Example Compounds and Reference compound 1 are presented in Table 1 to Table 44.

TABLE 1

| Example No. | Structural Formula | NMR | mass |
|---|---|---|---|
| 1 | (structure: 4-amino-1-(1-acryloylpiperidin-3-yl)-N-(6-chlorobenzo[d]oxazol-2-yl)-1H-pyrazolo[3,4-d]pyrimidine-3-carboxamide) | $^1$H NMR (400 MHz, DMSO-d$_6$) δ ppm 1.59 (br. s., 1 H) 1.95 (s, 1 H) 2.16 (br. s., 1 H) 2.32 (br. s., 1 H) 2.91 (br. s., 0.5 H) 4.11 (br. s., 0.5 H) 4.31 (br. s., 1 H) 4.57 (br. s., 1 H) 4.73 (br. s., 1 H) 5.65 (br. s., 1 H) 5.71 (br. s., 1 H) 6.08-6.18 (m, 1 H) 6.72-6.93 (m, 1 H) 6.76 (br. s., 1 H) 6.79 (s, 1 H) 6.84 (d, J = 12.44 Hz, 1 H) 7.36 (d, J = 7.56 Hz, 1 H) 7.70 (d, J = 15.12 Hz, 1 H) 8.16-8.36 (m, 3 H) | 469.1 |
| 2 | (structure: 4-amino-1-(1-acryloylpiperidin-3-yl)-N-(5-bromobenzo[d]oxazol-2-yl)-1H-pyrazolo[3,4-d]pyrimidine-3-carboxamide) | $^1$H NMR (400 MHz, DMSO-d$_6$) δ ppm 1.44-1.68 (m, 1 H) 1.87 (d, J = 12.30 Hz, 1 H) 2.06 (br. s., 1 H) 2.22 (d, J = 9.57 Hz, 1 H) 3.05-3.32 (m, 1 H) 4.03-4.25 (m, 0.5 H) 4.29-4.46 (m, 1 H) 4.60 (d, J = 18.45 Hz, 0.5 H) 5.51-5.75 (m, 1 H) 6.09 (br. s., 1 H) 6.61-6.95 (m, 1 H) 7.12 (s, 1 H) 7.24 (br. s., 1 H) 7.85 (br. s., 1 H) 8.10 (br. s., 1 H) 8.29 (s, 2 H) 11.07 (br. s., 1 H) | 513.1 |

TABLE 2
| Example No. | Structural Formula | NMR | mass |
|---|---|---|---|
| 3 | 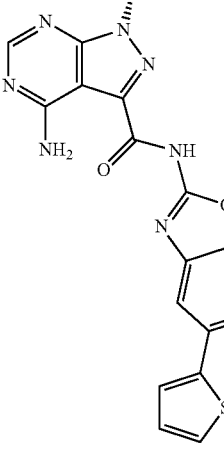 | $^1$H NMR (400 MHz, DMSO-d$_6$) δ ppm 1.33-1.46 (m, 1 H) 1.52-1.70 (m, 1 H) 1.90-2.03 (m, 1 H) 2.10-2.25 (m, 1 H) 2.85-2.98 (m, 1 H) 3.69-3.85 (m, 1 H) 4.05-4.43 (m, 2 H) 4.51-4.86 (m, 2 H) 5.61-5.77 (m, 1 H) 6.05-6.22 (m, 1 H) 6.71-6.95 (m, 1 H) 7.17 (d, J = 4.63 Hz, 1 H) 7.58 (d, J = 4.88 Hz, 2 H) 7.62-7.69 (m, 1 H) 7.70-7.78 (m, 1 H) 7.83-8.00 (m, 1 H) 8.16-8.27 (m, 1 H) 8.27-8.37 (m, 1 H) 8.32 (s, 2 H) | 515.2 |
| 4 | 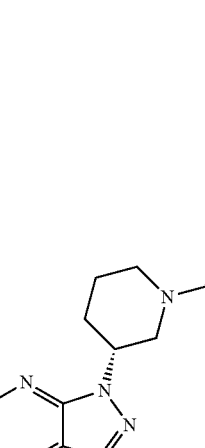 | $^1$H NMR(400 MHz, CHLOROFORM-d) δ ppm 1.73 (br. s., 1 H) 1.98 (br. s., 3 H) 2.27 (br. s., 2 H) 2.40 (d, J = 9.02 Hz, 1 H) 3.35-3.57 (m, 1 H) 3.64-4.14 (m, 2 H) 4.31 (br. s., 1 H) 4.94 (tt, J = 8.81, 4.24 Hz, 1 H) 5.09 (s, 1 H) 5.20 (br. s., 1 H) 6.58 (br. s., 1 H) 7.28-7.30 (m, 1 H) 7.45 (d, J = 8.78 Hz, 1 H) 7.68 (d, J = 1.95 Hz, 1 H) 8.34-8.42 (m, 2 H) 8.49 (br. s., 1 H) | 481.1 |

TABLE 3

| Example No. | Structural Formula | NMR | mass |
|---|---|---|---|
| 5 | | $^1$H NMR (400 MHz, DMSO-d$_6$) δ ppm 1.51 (br. s., 1 H) 1.75 (br. s., 1 H) 1.82 (br. s.,1 H) 2.05 (br. s., 1 H) 2.20 (d, J = 9.57 Hz, 1 H), 3.47 (s, 3 H) 4.09 (br. s., 3 H) 4.56 (br. s., 2 H) 6.37-6.74 (m, 1 H) 7.00 (d, J = 8.20 Hz, 1 H) 7.31 (d, J = 8.20 Hz, 1 H) 7.40 (s, 1 H) 7.79 (d, J = 4.10 Hz, 1 H) 8.09 (br. s., 1 H) 8.16 (s, 2 H) 10.89 (br. s., 2 H) | 481.2 |
| 6 | | $^1$H NMR (400 MHz, DMSO-d6) δ ppm 1.21-1.28 (m, 1 H) 1.63 (d, J = 12.93 Hz, 1 H) 1.90-1.98 (m, 1 H) 2.18 (br. s., 1 H) 2.27-2.44 (m, 1 H) 2.82-2.95 (m, 0.5 H) 3.17 (br. s., 0.5 H) 3.66-3.82 (m, 0.5 H) 4.13 (d, J = 12.68 Hz, 0.5 H) 4.32 (d, J = 15.37 Hz, 1 H) 4.62 (d, J = 11.95 Hz, 0.5 H) 4.74 (br. s., 1 H) 5.62-5.75 (m, 1 H) 6.09-6.24 (m, 1 H) 6.89 (dd, J = 16.59, 10.49 Hz, 1 H) 7.83 (dd, J = 8.41, 1.59 Hz, 1 H) 7.93 (d, J = 8.54 Hz, 1 H) 8.09-8.34 (m, 3 H) 12.24-12.68 (m, 1 H) | 459.2 |

TABLE 4
| Example No. | Structural Formula | NMR | mass |
| --- | --- | --- | --- |
| 7 | 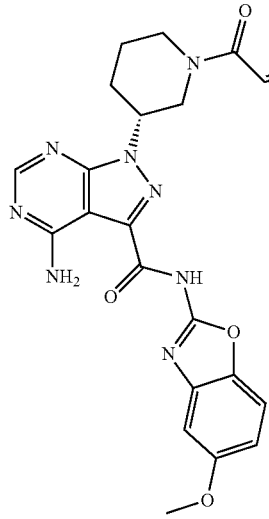 | $^1$H NMR (400 MHz, DMSO-d$_6$) δ ppm 1.49-1.74 (m, 1 H) 1.81-2.00 (m, 2 H) 2.09-2.40 (m, 2 H) 2.80-2.96 (m, 0.5 H) 3.07-3.23 (m, 0.5 H) 3.29-3.37 (m, 1 H) 3.69-3.84 (m, 4 H) 4.00-4.21 (m, 0.5 H) 4.21-4.43 (m, 1 H) 4.52-4.67 (m, 0.5 H) 4.64-4.84 (m, 1 H) 5.57-5.78 (m, 1 H) 6.04-6.24 (m, 1 H) 6.66-7.02 (m, 1 H) 7.74-7.96 (m, 1 H) 8.10-8.37 (m, 3 H) 12.37-12.62 (m, 1 H) | 464.0 |
| 8 | 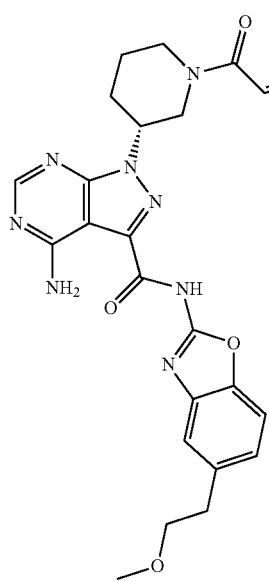 | $^1$H NMR (400 MHz, DMSO-d$_6$) δ ppm 1.49-1.75 (m, 1 H) 1.85-2.00 (m, 1 H) 2.08-2.24 (m, 1 H) 2.24-2.42 (m, 1 H) 2.92 (s, 2 H) 2.92 (t, J = 13.20 Hz, 2 H) 3.25 (s, 3 H) 3.24-3.27 (m, 1 H) 3.51-3.61 (m, 2 H) 3.92-4.46 (m, 3 H) 4.50-4.90 (m, 2 H) 5.54-5.81 (m, 1 H) 6.02-6.24 (m, 1 H) 6.64-6.98 (m, 2 H) 7.14-7.29 (m, 1 H) 7.41-7.69 (m, 1 H) 8.11-8.45 (m, 3 H) | 492.2 |

TABLE 5

| Example No. | Structural Formula | NMR | mass |
|---|---|---|---|
| 9 | | $^1$H NMR (400 MHz, DMSO-$d_6$) δ ppm 1.49-1.67 (m, 1 H) 1.86-2.13 (m, 2 H) 2.21-2.34 (m, 1 H) 2.74-2.86 (m, 0.5 H) 3.07-3.21 (m, 0.5 H) 3.55-3.67 (m, 0.5 H) 4.01-4.30 (m, 0.5 H) 4.37-4.49 (m, 1 H) 4.52-4.74 (m, 2 H) 5.59-5.76 (m, 1 H) 6.03-6.20 (m, 1 H) 6.73-6.94 (m, 1 H) 6.95-7.04 (m, 1 H) 7.59-7.68 (m, 1 H) 7.88 (br. s., 1 H) 8.10-8.15 (m, 2 H) 10.81-10.89 (m, 1 H) | 434.3 |
| 10 | | $^1$H NMR (400 MHz, DMSO-$d_6$) δ ppm 1.57 (br. s., 1 H) 1.83-1.98 (m, 1 H) 2.14 (br. s., 1 H) 2.23-2.38 (m, 1 H) 2.50 (s, 3H) 2.87 (br. s., 0.5 H) 3.71 (br. s., 0.5 H) 4.06 (br. s., 0.5 H) 4.28 (br. s., 0.5 H) 4.54 (br. s., 1 H) 4.72 (br. s., 1 H) 5.62 (br. s., 1 H) 5.67 (br. s., 1 H) 6.09 (s, 1 H) 6.14 (s, 1 H) 6.73 (br. s., 1 H) 6.84 (br. s., 1 H) 7.12-7.24 (m, 2 H) 7.45 (d, J = 7.52 Hz, 2 H) 8.09-8.21 (m, 2 H) 8.22-8.30 (m, 2 H) | 447.2 |

TABLE 6

| Example No. | Structural Formula | NMR | mass |
|---|---|---|---|
| 11 | | $^1$H NMR (400 MHz, DMSO-$d_6$) δ ppm 1.60 (d, J = 12.30 Hz, 1 H) 1.83 (br. s, 3H) 1.90 (br. s., 1 H) 2.13 (d, J = 8.20 Hz, 1 H) 2.32 (d, J = 10.25 Hz, 1 H) 3.88 (br. s., 1 H) 4.10 (br. s., 1 H) 4.41 (br. s., 1 H) 4.75 (br. s., 1 H) 5.01 (br. s., 1 H) 5.13 (br. s., 1 H) 7.12-7.19 (m, 1 H) 7.49 (d, J = 6.83 Hz, 1 H) 7.68 (dd, J = 8.88, 4.10 Hz, 1 H) 8.19 (br. s., 1 H) 8.26 (s, 1 H) 12.27 (br. s., 1 H) | 466.2 |

TABLE 6-continued

| Example No. | Structural Formula | NMR | mass |
|---|---|---|---|
| 12 | | $^1$H NMR (400 MHz, DMSO-d$^6$) δ ppm 1.50-1.69 (m, 1 H) 1.86-1.99 (m, 1 H) 2.09-2.26 (m, 1 H) 2.27-2.42 (m, 1 H) 2.84-2.97 (m, 0.5 H) 3.18 (t, J = 12.20 Hz, 0.5 H) 3.69-3.82 (m, 0.5 H) 4.11 (d, J = 13.17 Hz, 0.5 H) 4.22-4.39 (m, 1 H) 4.53-4.68 (m, 1 H) 4.72-4.76 (m, 0.5 H) 5.61-5.75 (m, 1 H) 6.07-6.19 (m, 1 H) 6.72-6.92 (m, 1 H) 7.20 (td, J = 9.39, 2.68 Hz, 1 H) 7.54 (d, J = 7.80 Hz, 1 H) 7.73 (dd, J = 8.78, 4.39 Hz, 1 H) 8.03-8.37 (m, 3 H) 12.29 (br. s., 1 H) | 451.2 |

TABLE 7

| Example No. | Structural Formula | NMR | mass |
|---|---|---|---|
| 13 | | $^1$H NMR (400 MHz, DMSO-d$_6$) δ ppm 1.52-1.69 (m, 1 H) 1.89-2.02 (m, 1 H) 2.09-2.25 (m, 1 H) 2.28-2.42 (m, 1 H) 2.83-2.98 (m, 0.5 H) 3.07-3.25 (m, 0.5 H) 3.23-3.37 (m, 0.5 H) 3.65-3.87 (m, 0.5 H) 4.06-4.17 (m, 0.5 H) 4.22-4.38 (m, 1 H) 4.56-4.65 (m, 0.5 H) 4.69-4.81 (m, 1 H) 5.55-5.81 (m, 1 H) 6.07-6.19 (m, 1 H) 6.73-6.92 (m, 1 H) 7.33-7.41 (m, 2 H) 7.59-7.76 (m, 2 H) 8.23 (br. s., 2 H) 8.30 (s, 1 H) 12.15 (br. s., 1H) | 433.0 |
| 14 | | $^1$H NMR (400 MHz, DMSO-d$_6$) δ ppm 1.14-1.52 (m, 1 H) 1.63-1.80 (m, 1 H) 1.91-2.00 (m, 1 H) 2.03 (br. s., 3 H) 2.08-2.19 (m, 1 H) 2.97 (br. s., 1 H) 3.45 (br. s., 1 H) 3.78 (br. s., 2 H) 4.58 (br. s., 1 H) 4.72-4.97 (m, 1 H) 5.50-5.89 (m, 1 H) 6.54-6.83 (m, 1 H) 7.65-8.10 (m, 1 H) 8.15-8.29 (m, 1 H) | 446.3 |

TABLE 8

| Example No. | Structural Formula | NMR | mass |
|---|---|---|---|
| 15 | | ¹H NMR (400 MHz, DMSO-d₆) δ ppm 1.53 (br. s., 2 H) 1.88 (d, J = 12.98 Hz, 2H) 2.09 (br. s., 3 H) 2.15 (br. s., 3H) 2.84 (br. s., 1 H) 2.96 (br. s., 1 H) 3.05 (br. s., 2 H) 3.13 (br. s., 2 H) 4.05 (br. s., 2 H) 4.14 (br. s., 3 H) 4.26 (br. s., 4 H) 4.61 (br. s., 6 H) 6.53 (br. s., 2 H) 6.62 (br. s., 2 H) 7.01 (d, J = 8.20 Hz, 1 H) 7.32 (d, J = 8.20 Hz, 1 H) 7.44 (s, 1 H) 7.83 (br. s., 2H) 8.09 (s, 1 H) 8.16 (s, 3 H) | 524.1 |
| 16 | | ¹H NMR (400 MHz, DMSO-d₆) δ ppm 0.91 (br. s., 3 H) 0.98 (br. s., 4 H) 1.54 (br. s., 2H) 1.88 (d, J = 12.30 Hz, 1 H) 2.09 (br. s., 3 H) 2.21 (br. s., 3 H) 2.34 (s, 3 H) 2.37 (s, 3 H) 3.05 (br. s., 2 H) 3.98-4.73 (m, 6 H) 6.53 (br. s., 2 H) 6.63 (br. s., 2 H) 7.01 (dd, J = 8.20, 2.05 Hz, 1 H) 7.33 (d, J = 8.20 Hz, 1 H) 7.45 (s, 1 H) 7.83 (br. s., 1 H) 8.09 (s, 1 H) 8.15 (s, 2 H) 10.82 (br. s., 1 H) | 538.2 |

TABLE 9

| Example No. | Structural Formula | NMR | mass |
|---|---|---|---|
| 17 | | ¹H NMR (400 MHz, DMSO-d₆) δ ppm 0.88 (br. s., 3 H) 0.95 (br. s., 3 H) 1.54 (br. s., 2 H) 1.89 (d, J = 11.62 Hz, 2 H) 2.06 (br. s., 2 H) 2.22 (br. s., 2 H) 2.63 (br. s., 1 H) 2.69 (br. s., 1 H) 4.10 (d, J = 15.72 Hz, 4 H) 4.26 (m, 3 H) 4.62 (m, 4 H) 6.56 (br. s., 2 H) 6.65 (br. s., 2 H) 7.01 (dd, J = 8.20, 2.05 Hz, 1 H) 7.33 (d, J = 8.20 Hz, 1 H) 7.45 (s, 1 H) 7.83 (d, J = 4.10 Hz, 2H) 8.09 (s, 1 H) 8.15 (s, 2 H) 10.82 (br. s., 1 H) | 552.3 |

TABLE 9-continued

| Example No. | Structural Formula | NMR | mass |
|---|---|---|---|
| 18 | 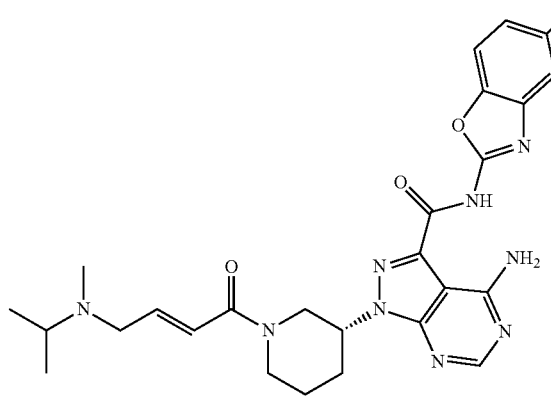 | ¹H NMR (400 MHz, DMSO-d₆) δ ppm 0.91 (s, 5 H) 0.95 (s, 5 H) 1.19-1.26 (m, 1 H) 1.53 (br. s., 1 H) 1.87 (br. s., 1 H) 2.08 (br. s., 4H) 2.13 (br. s., 3 H) 2.20 (br. s., 2 H) 2.72-2.94 (m, 3 H) 4.00-4.32 (m, 2 H) 4.41-4.70 (m, 4 H) 6.48-6.72 (m, 3 H) 7.00-7.04 (m, 1 H) 7.33 (d, J = 8.20 Hz, 1 H) 7.45 (s, 1 H) 7.84 (br. s., 2 H) 8.09-8.18 (m, 2 H) 10.79 (br. s., 1 H) | 552.3 |

TABLE 10

| Example No. | Structural Formula | NMR | mass |
|---|---|---|---|
| 19 | 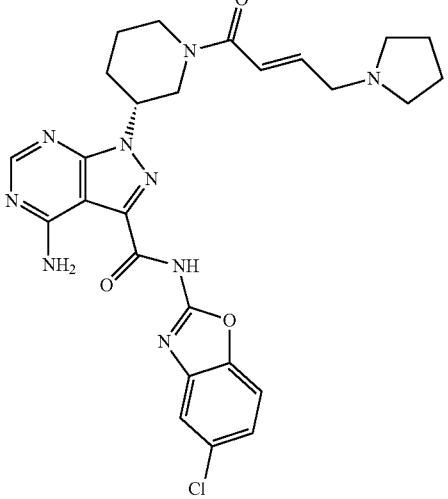 | ¹H NMR (400 MHz, DMSO-d₆) δ ppm 1.62 (br. s., 4 H) 1.67 (br. s., 3 H) 1.89 (d, J = 13.67 Hz, 2 H) 2.06 (br. s., 2 H) 2.22 (br. s., 2 H) 2.85 (br. s., 2 H) 3.13 (br. s., 2 H) 3.23 (br. s., 2 H) 3.97-4.33 (m, 4 H) 4.45-4.68 (m, 4 H) 6.53 (br. s., 1 H) 6.63 (br. s., 1 H) 7.01 (dd, J = 8.20, 2.05 Hz, 1 H) 7.32 (d, J = 8.20 Hz, 1 H) 7.45 (s, 1 H) 7.82 (d, J = 4.78 Hz, 1 H) 8.09 (s, 1 H) 8.18 (s, 2 H) 10.86 (br. s., 1 H) | 550.2 |
| 20 | 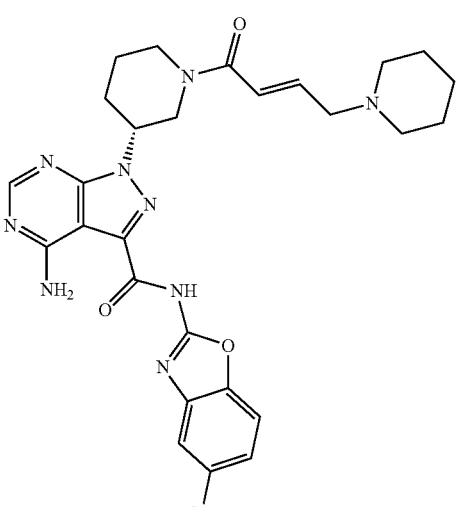 | ¹H NMR (400 MHz, DMSO-d₆) δ ppm 1.34 (br. s., 3 H) 1.40 (br. s., 3 H) 1.47 (br. s., 6 H) 1.88 (d, J = 13.67 Hz, 1 H) 2.05 (d, J = 8.20 Hz, 1 H) 2.25 (br. s., 4 H) 2.32 (br. s., 4 H) 2.85 (br. s., 1 H) 2.95 (br. s., 2 H) 4.00-4.37 (m, 4 H) 4.47-4.69 (m, 4 H) 6.50 (br. s., 1 H) 6.61 (br. s., 2 H) 7.01 (dd, J = 8.20, 2.05 Hz, 1 H) 7.32 (d, J = 8.20 Hz, 1 H) 7.45 (s, 1 H) 7.82 (d, J = 4.10 Hz, 1 H) 8.09 (s, 1 H) 8.17 (s, 2 H) 10.86 (br. s., 1 H) | 564.3 |

TABLE 11

| Example No. | Structural Formula | NMR | mass |
|---|---|---|---|
| 21 | | $^1$H NMR (400 MHz, DMSO-d$_6$) δ ppm 1.46-1.64 (m, 1 H) 1.82-1.94 (m, 1 H) 2.00-2.10 (m, 4 H) 2.13 (br. s., 3H) 2.17-2.27 (m, 1 H) 2.79-2.90 (m, 0.5 H) 3.06-3.12 (m, 0.5 H) 3.57-3.66 (m, 5 H) 3.99-4.35 (m, 4 H) 4.47-4.70 (m, 2 H) 6.48-6.68 (m, 2 H) 7.05-7.12 (m, 1 H) 7.29-7.40 (m, 2 H) 7.41-7.47 (m, 1 H) 7.68 (s, 1 H) 7.79-7.86 (m, 1 H) 8.09 (s, 2 H) 8.19 (s, 1 H) 10.95 (br. s., 1 H) | 469.2 |
| 22 | | $^1$H NMR (400 MHz, DMSO-d$_6$) δ ppm 1.42-1.77 (m, 1 H) 1.95-2.02 (m, 1 H) 2.06 (s, 3 H) 2.10-2.22 (m, 1 H) 2.23-2.40 (m, 1 H) 2.95-3.10 (m, 0.5 H) 3.83-3.95 (m, 0.5 H) 4.09-4.19 (m, 0.5 H) 4.22-4.35 (m, 1 H) 4.37-4.56 (m, 1 H) 4.61-4.93 (m, 1 H) 7.26-7.44 (m, 2 H) 7.55-7.76 (m, 2 H) 7.95-8.49 (m, 3 H) | 445.9 |

TABLE 12

| Example No. | Structural Formula | NMR | mass |
|---|---|---|---|
| 23 | | $^1$H NMR (400 MHz, DMSO-d$_6$) δ ppm 1.44-1.68 (m, 1 H) 1.87 (d, J = 12.30 Hz, 1 H) 2.06 (br. s., 1 H) 2.22 (d, J = 9.57 Hz, 8 H) 3.05-3.32 (m, 4 H) 4.03-4.25 (m, 3 H) 4.29-4.46 (m, 1 H) 4.60 (d, J = 18.45 Hz, 2 H) 5.51-5.75 (m, 1 H) 6.09 (br. s., 1 H) 6.61-6.95 (m, 1 H) 7.12 (s, 1 H) 7.24 (br. s., 1 H) 7.85 (br. s., 1 H) 8.10 (br. s., 1 H) 8.29 (s, 2 H) 11.07 (br. s., 1 H) | 461.2 |

TABLE 12-continued
| Example No. | Structural Formula | NMR | mass |
|---|---|---|---|
| 24 | 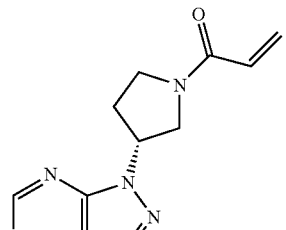 | $^1$H NMR (400 MHz, DMSO-d$_6$) δ ppm 2.35-2.46 (m, 2 H) 3.60 (br. s., 1 H) 3.78 (br. s., 1 H) 3.84 (br. s., 1 H) 3.93 (br. s., 1 H) 4.02 (br. s., 1 H) 4.11 (d, J = 5.47 Hz, 1 H) 5.39-5.76 (m, 2 H) 6.00-6.29 (m, 1 H) 6.11 (s, 1 H) 6.15 (s, 1 H) 6.50-6.68 (m, 1 H) 7.35 (d, J = 8.88 Hz, 1 H) 7.69 (d, J = 8.88 Hz, 2H) 8.11-8.38 (m, 2 H) 12.32 (br. s., 1 H) | 453.1 |
TABLE 13
| Example No. | Structural Formula | NMR | mass |
|---|---|---|---|
| 25 | | $^1$H NMR (400 MHz, DMSO-d$_6$) δ ppm 1.80 (dd, J = 15.72, 6.15 Hz, 5 H) 1.92 (br. s., 1 H) 2.28-2.42 (m, 1 H) 2.50 (br. s., 1 H) 3.37-3.61 (m, 5 H) 3.65-3.78 (m, 2 H) 3.78-3.99 (m, 4 H) 4.01-4.15 (m, 1 H) 5.43 (t, J = 5.81 Hz, 1 H) 5.48-5.56 (m, 1 H) 6.21-6.34 (m, 1 H) 6.63-6.73 (m, 1 H) 7.24 (br. s., 1 H) 7.61 (br. s., 3 H) 8.02-8.15 (m, 2H) 8.22 (s, 1 H) 12.38 (br. s., 1 H) | 469.2 |

TABLE 13-continued
| Example No. | Structural Formula | NMR | mass |
|---|---|---|---|
| 26 | 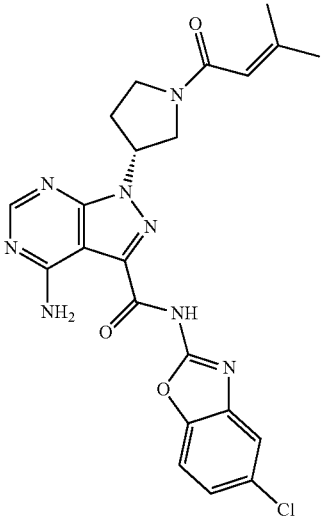 [SMILES: CC(C)=CC(=O)N1CC[C@@H](n2nc(C(=O)Nc3nc4cc(Cl)ccc4o3)c3c(N)ncnc32)C1] | $^1$H NMR (400 MHz, DMSO-d$_6$) δ ppm 1.80 (d, J = 19.80 Hz, 3 H) 1.94-2.01 (m, 3 H) 3.45-3.57 (m, 1 H) 3.59-3.71 (m, 1 H) 3.76-3.94 (m, 3 H) 3.95-4.07 (m, 1 H) 5.32-5.64 (m, 1 H) 5.82-6.02 (m, 1 H) 7.19-7.44 (m, 1 H) 7.51-7.80 (m, 2 H) 8.08-8.16 (m, 1 H) 8.19-8.35 (m, 2 H) | 483.2 |
TABLE 14
| Example No. | Structural Formula | NMR | mass |
|---|---|---|---|
| 27 | 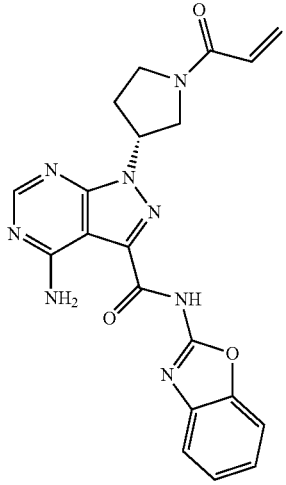 [SMILES: C=CC(=O)N1CC[C@@H](n2nc(C(=O)Nc3nc4ccccc4o3)c3c(N)ncnc32)C1] | $^1$H NMR (400 MHz, DMSO-d$_6$) δ ppm 2.39-2.52 (m, 2 H) 3.51-3.67 (m, 1 H) 3.70-3.86 (m, 3 H) 3.88-3.98 (m, 3 H) 4.03-4.16 (m, 1 H) 5.41-5.55 (m, 1 H) 5.65 (ddd, J = 17.77, 10.25, 2.05 Hz, 1 H) 6.10-6.17 (m, 1 H) 6.51-6.67 (m, 1 H) 7.09-7.21 (m, 2 H) 7.40-7.51 (m, 1 H) 7.95 (br. s., 2H) 8.11 (s, 1 H) 8.17 (s, 2 H) | 420.1 |

TABLE 14-continued
| Example No. | Structural Formula | NMR | mass |
|---|---|---|---|
| 28 | 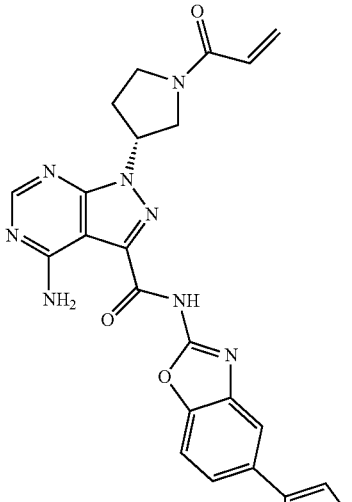 | $^1$H NMR (400 MHz, DMSO-d$_6$) δ ppm 2.23-2.39 (m, 3 H) 3.57-3.94 (m, 4 H) 3.99-4.16 (m, 2 H) 5.39-5.46 (m, 1 H) 5.48-5.55 (m, 1 H) 5.61-5.70 (m, 2 H) 6.10-6.17 (m, 2 H) 6.51-6.67 (m, 2 H) 7.07-7.10 (m, 1 H) 7.32-7.41 (m, 1 H) 7.45 (d, J = 4.78 Hz, 1 H) 7.72 (s, 2 H) 7.88 (br. s., 2 H) 8.13 (s, 1 H) 10.57-10.99 (m, 1 H) | 501.2 |
TABLE 15
| Example No. | Structural Formula | NMR | mass |
|---|---|---|---|
| 29 | 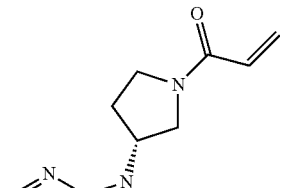 | $^1$H NMR (400 MHz, DMSO-d$_6$) δ ppm 2.37 (s, 3 H) 3.47 (s, 4 H) 3.51-3.66 (m, 1 H) 3.73-4.01 (m, 3 H) 4.05-4.15 (m, 1 H) 5.42-5.57 (m, 1 H) 5.65 (ddd, J = 17.08, 10.25, 2.05 Hz, 1 H) 6.13 (dd, J = 19.13, 5.47 Hz, 1 H) 6.13 (dd, J = 14.69, 5.81 Hz, 1 H) 6.51-6.67 (m, 1 H) 7.03 (d, J = 7.52 Hz, 1 H) 7.34 (br. s., 1 H) 7.41 (d, J = 8.20 Hz, 1 H) 8.06 (s, 1 H) 8.10 (s, 1 H) 8.22 (s, 2 H) | 433.2 |

TABLE 15-continued

| Example No. | Structural Formula | NMR | mass |
|---|---|---|---|
| 30 | | $^1$H NMR (400 MHz, DMSO-d$_6$) δ ppm 2.36 (dd, J = 12.98, 6.15 Hz, 1 H) 2.54 (d, J = 5.47 Hz, 2 H) 3.51-3.68 (m, 0.5 H) 3.73-4.11 (m, 4H) 5.45 (t, J = 6.15 Hz, 1 H) 5.54 (t, J = 6.15 Hz, 1 H) 5.65 (ddd, J = 17.08, 10.25, 2.05 Hz, 2 H) 6.09-6.17 (m, 1 H) 6.51-6.67 (m, 1 H) 7.02 (br. s., 2 H) 7.39 (br. s., 1 H) 7.54 (br. s., 1 H) 8.01-8.15 (m, 3 H) 8.21 (s, 1 H) | 437.1 |

TABLE 16

| Example No. | Structural Formula | NMR | mass |
|---|---|---|---|
| 31 | | $^1$H NMR (400 MHz, DMSO-d$_6$) δ ppm 2.20-2.42 (m, 2 H) 3.59 (br. s., 3 H) 3.64-4.00 (m, 4 H) 4.09 (d, J = 7.52 Hz, 1 H) 5.38-5.56 (m, 1 H) 5.58-5.75 (m, 1 H) 6.05-6.22 (m, 1 H) 6.46-6.71 (m, 1 H) 7.47 (d, J = 8.88 Hz, 2 H) 7.62-7.72 (m, 3 H) 7.77-7.89 (m, 1 H) 8.08-8.13 (m, 1 H) 8.30 (br. s., 2 H) 11.05-11.16 (m, 1 H) | 529.1 |
| 32 | | $^1$H NMR (400 MHz, DMSO-d$_6$) δ ppm 2.14 (s, 3 H) 2.17 (s, 3 H) 2.34 (br. s., 2 H) 2.43 (br. s., 2 H) 3.03-3.14 (m, 2 H) 3.88 (br. s., 5 H) 4.07 (br. s., 5 H) 5.41 (br. s., 1 H) 5.48 (br. s., 1 H) 6.33-6.45 (m, 1 H) 6.61 (d, J = 6.83 Hz, 1 H) 7.02 (d, J = 8.20 Hz, 1 H) 7.33 (d, J = 8.20 Hz, 1 H) 7.45 (br. s., 1 H) 7.85 (br. s., 1 H) 8.10-8.15 (m, 2 H) 10.76 (br. s., 2 H) | 510.1 |
| 33 | | $^1$H NMR (400 MHz, DMSO-d$_6$) δ ppm 0.91-0.99 (m, 3 H) 2.06-2.14 (m, 3 H) 2.28-2.38 (m, 3 H) 2.41 (d, J = 6.83 Hz, 2 H) 3.04-3.13 (m, 2 H) 4.07 (br. s., 4 H) 5.41 (br. s., 1 H) 5.49 (br. s., 1 H) 6.31-6.44 (m, 1 H) 6.62 (d, J = 6.15 Hz, 1 H) 7.01 (d, J = 8.88 Hz, 1 H) 7.32 (d, J = 8.20 Hz, 1 H) 7.48 (br. s., 1 H) 7.84 (br. s., 2 H) 8.11 (s, 1 H) 8.22 (s, 2 H) 10.94 (br. s., 2 H) | 524.1 |

TABLE 17

| Example No. | Structural Formula | NMR | mass |
|---|---|---|---|
| 34 | | $^1$H NMR (400 MHz, DMSO-d$_6$) δ ppm 0.92 (dt, J = 14.35, 7.18 Hz, 6 H) 2.38-2.44 (m, 5 H) 3.09-3.23 (m, 3 H) 3.96-4.23 (m, 3 H) 5.26-5.58 (m, 1 H) 6.28-6.50 (m, 1 H) 6.56-6.72 (m, 1 H) 6.96-7.06 (m, 1 H) 7.27-7.36 (m, 1 H) 7.43-7.51 (m, 1 H) 7.79-7.88 (m, 1 H) 8.03 (s, 1 H) 8.22 (s, 2 H) 10.85-11.00 (m, 1 H) | 538.1 |
| 35 | | $^1$H NMR (400 MHz, DMSO-d$_6$) δ ppm 2.07 (d, J = 15.03 Hz, 6 H) 2.33 (d, J = 7.52 Hz, 2 H) 2.60-2.91 (m, 1 H) 3.03-3.20 (m, 2 H) 4.00-4.14 (m, 1 H) 5.31-5.58 (m, 2 H) 6.25-6.46 (m, 2 H) 6.52-6.68 (m, 2 H) 6.95-7.06 (m, 1 H) 7.27-7.36 (m, 1 H) 7.41-7.53 (m, 1 H) 7.80-7.91 (m, 2 H) 8.03 (s, 1 H) 8.22 (s, 2 H) | 538.1 |

TABLE 18

| Example No. | Structural Formula | NMR | mass |
|---|---|---|---|
| 36 | | $^1$H NMR (400 MHz, DMSO-d$_6$) δ ppm 1.60-1.70 (m, 1 H) 1.65 (d, J = 12.30 Hz, 4H) 2.33 (d, J = 6.83 Hz, 2 H) 2.41 (br. s., 2 H) 3.12-3.25 (m, 2 H) 3.19 (d, J = 12.30 Hz, 2 H) 3.68-3.79 (m, 2 H) 3.79-3.96 (m, 2 H) 3.97-4.24 (m, 2 H) 4.02-4.15 (m, 1 H) 5.40 (br. s., 1 H) 5.49 (br. s., 1 H) 6.31-6.44 (m, 2 H) 6.62-6.68 (m, 2 H) 7.01 (d, J = 8.20 Hz, 2 H) 7.31 (d, J = 8.20 Hz, 2 H) 7.47 (s, 1 H) 7.79-7.90 (m, 1 H) 7.84 (br. s., 2 H) 8.07-8.13 (m, 1 H) 8.07-8.14 (m, 1 H) 8.03 (s, 1 H) 8.22 (s, 2 H) 10.93 (br. s., 1 H) | 536.1 |

TABLE 18-continued
| Example No. | Structural Formula | NMR | mass |
|---|---|---|---|
| 37 | 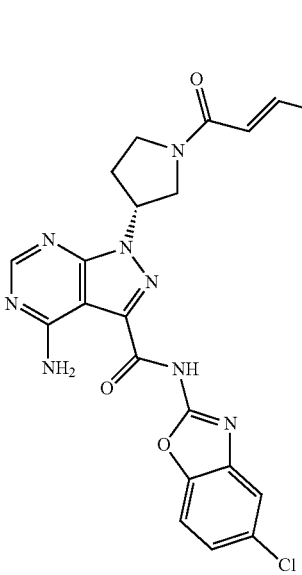 | $^1$H NMR (400 MHz, DMSO-d$_6$) δ ppm 1.34 (br. s., 2 H) 1.40-1.52 (m, 4 H) 2.33 (br. s., 4 H) 2.39-2.44 (m, 1 H) 2.93-3.20 (m, 2 H) 3.80-3.97 (m, 2 H) 4.06 (d, J = 7.52 Hz, 2 H) 5.40 (br. s., 1 H) 5.49 (br. s., 1 H) 6.31-6.44 (m, 1 H) 6.57-6.66 (m, 1 H) 7.01 (d, J = 8.20 Hz, 1 H) 7.32 (d, J = 8.20 Hz, 1 H) 7.45 (s, 1 H) 7.84 (br. s., 1 H) 8.03 (s, 1 H) 8.22 (s, 2 H) 10.81 (br. s., 1 H) | 550.1 |
TABLE 19
| Example No. | Structural Formula | NMR | mass |
|---|---|---|---|
| 38 | 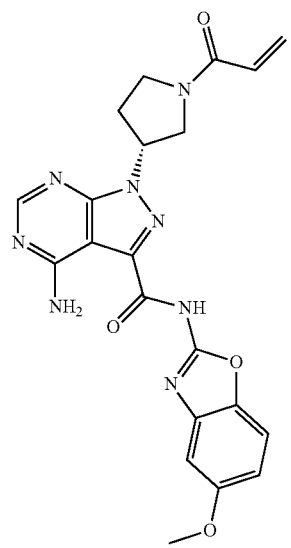 [SMILES: C=CC(=O)N1CC[C@@H](n2nc(C(=O)Nc3nc4cc(OC)ccc4o3)c3c(N)ncnc32)C1] | $^1$H NMR (400 MHz, DMSO-d$_6$) δ ppm 2.43 (d, J = 5.61 Hz, 1 H) 3.50-3.70 (m, 2 H) 3.74-3.88 (m, 2 H) 3.81 (s, 3 H) 3.96 (d, J = 7.07 Hz, 1 H) 4.05 (br. s., 1 H) 4.15 (d, J = 7.32 Hz, 1 H) 5.51 (d, J = 6.10 Hz, 1 H) 5.60 (s, 1 H) 5.69 (ddd, J = 15.98, 10.37, 2.44 Hz, 1 H) 6.17 (ddd, J = 16.65, 4.94, 2.32 Hz, 1 H) 6.55-6.71 (m, 1 H) 6.92 (dd, J = 8.90, 2.56 Hz, 1 H) 7.20 (br. s., 1 H) 7.59 (d, J = 9.02 Hz, 1 H) 8.33 (s, 2 H) | 450.2 |

TABLE 19-continued
| Example No. | Structural Formula | NMR | mass |
|---|---|---|---|
| 39 | 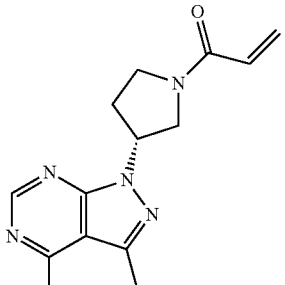 | $^1$H NMR (400 MHz, DMSO-$d_6$) δ ppm 2.33 (br. s., 1 H) 2.66-2.70 (m, 1 H) 3.35 (br. s., 2 H) 3.74-3.90 (m, 3 H) 3.94 (d, J = 7.80 Hz, 1 H) 4.14 (s, 1 H) 5.48 (s, 1 H) 5.56 (s, 1 H) 5.63-5.74 (m, 1 H) 6.11-6.20 (m, 1 H) 6.54-6.68 (m, 1 H) 7.61 (br. s., 1 H) 7.67 (br. s., 1 H) 7.98 (br. s., 1 H) 8.09-8.25 (m, 2 H) | 444.2 |
TABLE 20
| Example No. | Structural Formula | NMR | mass |
|---|---|---|---|
| 40 | 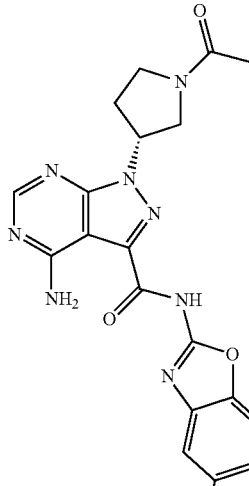 | $^1$H NMR (400 MHz, DMSO-$d_6$) δ ppm 2.39 (d, J = 6.83 Hz, 2 H) 2.89 (t, J = 6.49 Hz, 2 H) 3.22 (s, 3 H) 3.54 (t, J = 6.49 Hz, 2 H) 3.73-3.88 (m, 1 H) 3.93 (d, J = 6.15 Hz, 1 H) 4.01 (br. s., 1 H) 4.06-4.15 (m, 1 H) 5.45-5.70 (m, 2 H) 6.10-6.17 (m, 1 H) 6.51-6.67 (m, 1 H) 7.19 (m, J = 8.20 Hz, 1 H) 7.47 (br. s., 1 H) 7.54 (m, J = 8.20 Hz, 1 H) 8.20 (br. s., 2 H) 8.27 (br. s., 1 H) 12.13 (br. s., 1 H) | 477.2 |

TABLE 20-continued

| Example No. | Structural Formula | NMR | mass |
|---|---|---|---|
| 41 | | $^1$H NMR (400 MHz, DMSO-d$_6$) δ ppm 2.32-2.43 (m, 1 H) 3.52-3.63 (m, 1 H) 3.74-4.02 (m, 2 H) 4.06-4.16 (m, 1 H) 5.43-5.58 (m, 1 H) 5.62-5.70 (m, 2 H) 6.10-6.17 (m, 2 H) 6.51-6.67 (m, 1 H) 7.31-7.37 (m, 1 H) 7.41-7.54 (m, 3 H) 7.66 (d, J = 7.52 Hz, 3 H) 7.79 (br. s., 1 H) 8.00-8.16 (m, 2 H) 8.03 (s, 1 H) 8.22 (s, 2 H) | 496.1 |

TABLE 21

| Example No. | Structural Formula | NMR | mass |
|---|---|---|---|
| 42 | | $^1$H NMR (400 MHz, DMSO-d$_6$) δ ppm 2.11 (s, 3 H) 2.14 (s, 3 H) 2.34 (br. s., 3 H) 2.42 (d, J = 6.83 Hz, 1 H) 3.02 (dd, J = 16.40, 6.15 Hz, 3 H) 3.81-3.96 (m, 6 H) 3.97-4.23 (m, 4 H) 5.45 (dt, J = 33.50, 6.80 Hz, 1 H) 6.31-6.44 (m, 1 H) 6.57-6.64 (m, 1 H) 7.30 (d, J = 8.20 Hz, 3 H) 7.40 (d, J = 8.20 Hz, 3 H) 7.59 (br. s., 2 H) 7.72 (s, 1 H) 7.87 (br. s., 1 H) 8.03 (s, 1 H) 8.22 (s, 2 H) 10.86 (br. s., 1 H) | 552.1 |
| 43 | | $^1$H NMR (400 MHz, DMSO-d$_6$) δ ppm 2.41 (br. s., 1 H) 2.61 (br. s., 1 H) 3.62 (br. s., 2 H) 3.81 (br. s., 1 H) 3.87 (br. s., 1 H) 3.96 (br. s., 1 H) 4.06 (d, J = 10.25 Hz, 1 H) 4.16 (br. s., 1 H) 5.46-5.63 (m, 1 H) 5.63-5.74 (m, 1 H) 6.10-6.23 (m, 1 H) 6.55-6.70 (m, 1 H) 7.68 (d, J = 7.52 Hz, 1 H) 7.88 (d, J = 7.52 Hz, 1 H) 8.01 (br. s., 1 H) 8.20 (br. s., 1 H) 8.30 (br. s., 2 H) | 487.2 |

TABLE 22

| Example No. | Structural Formula | NMR | mass |
|---|---|---|---|
| 44 | | $^1$H NMR (400 MHz, DMSO-d$_6$) δ ppm 2.19 (s, 3 H) 2.22 (s, 3 H) 2.28-2.39 (m, 1 H) 2.85 (br. s., 1 H) 2.98-3.00 (m, 1 H) 3.55 (d, J = 11.62 Hz, 1 H) 3.63-3.82 (m, 5 H) 3.89 (dd, J = 12.30, 6.83 Hz, 3 H) 3.99-4.18 (m, 2 H) 5.39-5.52 (m, 1 H) 6.36-6.48 (m, 1 H) 6.57-6.66 (m, 1 H) 7.36 (d, J = 8.20 Hz, 1 H) 7.52 (d, J = 8.20 Hz, 1 H) 7.74 (s, 1 H) 7.87 (br. s., 1 H) 8.12 (d, J = 5.47 Hz, 1 H) 10.68 (br. s., 1 H) | 544.3 |
| 45 | | $^1$H NMR (400 MHz, DMSO-d$_6$) δ ppm 4.33 (d, J = 4.78 Hz, 1 H) 4.41 (d, J = 9.57 Hz, 1 H) 4.58 (br. s., 1 H) 4.72 (t, J = 8.54 Hz, 1 H) 5.70 (d, J = 10.25 Hz, 2 H) 6.14 (d, J = 17.08 Hz, 1 H) 6.37 (dd, J = 17.08, 10.25 Hz, 1 H) 6.96-7.02 (m, 1 H) 6.99 (d, J = 6.15 Hz, 1 H) 7.31 (d, J = 8.88 Hz, 1 H) 7.38 (s, 1 H) 7.85 (br. s., 1 H) 8.03 (s, 1 H) 8.22 (s, 2 H) 10.97 (br. s., 1 H) | 466.2 |

TABLE 23

| Example No. | Structural Formula | NMR | mass |
|---|---|---|---|
| 46 | | $^1$H NMR (400 MHz, DMSO-d$_6$) δ ppm 4.21-4.34 (m, 1 H) 4.42 (t, J = 9.23 Hz, 1 H) 4.61 (d, J = 5.47 Hz, 1 H) 4.65-4.74 (m, 1 H) 5.52 (d, J = 5.47 Hz, 1 H) 5.69 (dd, J = 10.25, 2.05 Hz, 1 H) 6.13 (dd, J = 17.08, 2.05 Hz, 1 H) 6.36 (dd, J = 17.08, 10.25 Hz, 1 H) 6.99 (d, J = 8.20 Hz, 1 H) 7.31 (d, J = 8.20 Hz, 1 H) 7.39 (s, 1 H) 7.98-8.05 (m, 1 H) 8.18 (br. s., 1 H) 8.22 (s, 2 H) | 438.2 |

TABLE 23-continued

| Example No. | Structural Formula | NMR | mass |
|---|---|---|---|
| 47 | | Cl $^1$H NMR (400 MHz, DMSO-d$_6$) δ ppm 2.10-2.17 (m, 6 H) 3.02 (d, J = 5.47 Hz, 2 H) 4.20-4.27 (m, 2 H) 4.40 (t, J = 9.23 Hz, 2 H) 4.57 (d, J = 5.47 Hz, 2 H) 4.69 (t, J = 8.54 Hz, 2 H) 5.52 (br. s., 1 H) 6.15 (d, J = 15.72 Hz, 1 H) 6.58-6.66 (m, 1 H) 7.04 (d, J = 8.20 Hz, 1 H) 7.35 (d, J = 8.20 Hz, 1 H) 7.43 (s, 1 H) 8.11 (br. s., 1 H) 8.18 (s, 2 H) | 495.2 |

TABLE 24

| Example No. | Structural Formula | NMR | mass |
|---|---|---|---|
| 48 | | $^1$H NMR (400 MHz, DMSO-d$_6$) δ ppm 2.25-2.43 (m, 2 H) 3.73-3.81 (m, 2 H) 3.86-3.97 (m, 2 H) 4.06-4.15 (m, 1 H) 5.23 (br. s., 1 H) 5.34 (d, J = 6.15Hz, 2 H) 5.63-5.73 (m, 3 H) 6.12-6.21 (m, 2 H) 6.55-6.67 (m, 2 H) 6.95 (d, J = 8.20 Hz, 2 H) 7.10 (br. s, 1 H) 7.25 (d, J = 8.20 Hz, 2 H) 7.39 (br. s., 2 H) 7.63 (s, 1 H) 7.67 (s, 2 H) 8.02 (s, 1 H) 8.27 (br. s., 4 H) 10.29 (br. s., 1 H) | 452.1 |
| 49 | | $^1$H NMR (400 MHz, DMSO-d$_6$) δ ppm 2.10 (s, 3 H) 2.15 (s, 3 H) 2.95-3.09 (m, 4 H) 3.02 (d, J = 17.77 Hz, 4 H) 3.13 (s, 17 H) 5.16-5.40 (m, 3 H) 6.26-6.51 (m, 1 H) 6.56-6.74 (m, 1 H) 6.90-7.06 (m, 1 H) 7.22-7.32 (m, 1 H) 7.36-7.48 (m, 1 H) 7.59-7.76 (m, 1 H) 7.96-8.09 (m, 1 H) 8.25 (s, 2 H) | 509.1 |

TABLE 25

| Example No. | Structural Formula | NMR | mass |
|---|---|---|---|
| 50 | | ¹H NMR (400 MHz, DMSO-d₆) δ ppm 0.95 (dt, J = 11.28, 7.00 Hz, 3 H) 2.11 (d, J = 12.98 Hz, 2 H) 2.27-2.45 (m, 2 H) 3.13 (m, 2 H) 3.87-3.97 (m, 1 H) 3.98-4.24 (m, 1 H) 5.12-5.42 (m, 1 H) 6.30-6.50 (m, 1 H) 6.58-6.73 (m, 1 H) 6.99-7.07 (m, 1 H) 7.31-7.38 (m, 1 H) 7.40-7.46 (m, 1 H) 7.77-7.85 (m, 1 H) 8.02-8.08 (m, 1 H) 8.19 (s, 2 H) | 523.2 |
| 51 | | ¹H NMR (400 MHz, DMSO-d₆) δ ppm 0.88-0.97 (m, 6 H) 2.38-2.52 (m, 4 H) 3.13-3.34 (m, 2 H) 3.70 (d, J = 6.83 Hz, 1 H) 3.78-3.96 (m, 1 H) 3.97-4.23 (m, 1 H) 5.14-5.41 (m, 1 H) 6.32-6.49 (m, 1 H) 6.67 (tt, J = 13.84, 7.00 Hz, 1 H) 6.99 (d, J = 8.20 Hz, 1 H) 7.30 (dd, J = 8.54, 2.39 Hz, 1 H) 7.41 (br. s., 1 H) 7.74 (d, J = 13.67 Hz, 1 H) 8.03 (s, 1 H) 8.21 (s, 2 H) | 537.2 |

TABLE 26

| Example No. | Structural Formula | NMR | mass |
|---|---|---|---|
| 52 | | ¹H NMR (400 MHz, DMSO-d₆) δ ppm 0.92 (dd, J = 11.28, 6.49 Hz, 6 H) 2.02-2.14 (m, 1 H) 2.08 (d, J = 13.67 Hz, 3 H) 2.76 (dt, J = 12.98, 6.49 Hz, 1 H) 3.14 (dd, J = 17.08, 6.15 Hz, 1 H) 3.71 (br. s., 1 H) 3.79-3.96 (m, 1 H) 3.97-4.26 (m, 1 H) 5.13-5.37 (m, 1 H) 6.30-6.47 (m, 1 H) 6.54-6.70 (m, 1 H) 6.94-7.06 (m, 1 H) 7.27-7.36 (m, 1 H) 7.39-7.45 (m, 1 H) 7.71-7.80 (m, 1 H) 8.04 (s, 1 H) 8.20 (s, 2 H) | 537.2 |
| 53 | | ¹H NMR (400 MHz, DMSO-d₆) δ ppm 1.61-1.72 (m, 4 H) 3.09-3.34 (m, 2 H) 3.86 (d, J = 6.83 Hz, 1 H) 3.95-4.22 (m, 1 H) 5.09-5.37 (m, 1 H) 6.30-6.48 (m, 1 H) 6.58-6.76 (m, 1 H) 6.89-7.01 (m, 1 H) 7.20-7.29 (m, 1 H) 7.38-7.44 (m, 1 H) 7.59-7.69 (m, 1 H) 7.98-8.06 (m, 1 H) 8.03 (s, 1 H) 8.22 (s, 2 H) | 535.2 |

TABLE 27

| Example No. | Structural Formula | NMR | mass |
|---|---|---|---|
| 54 | 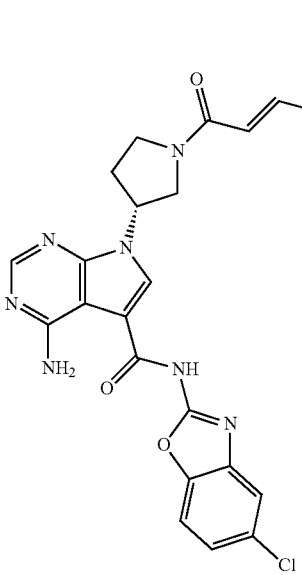 | ¹H NMR (400 MHz, DMSO-d₆) δ ppm 1.19-1.30 (m, 1 H) 1.33 (br. s., 3 H) 1.40-1.51 (m, 6 H) 2.24-2.36 (m, 7 H) 2.41-2.51 (m, 12 H) 3.04 (dd, J = 17.77, 6.15 Hz, 3 H) 3.13 (br. s., 2 H) 3.47 (br. s., 16 H) 3.71 (br. s., 11 H) 3.88 (dd, J = 12.64, 6.49 Hz, 10 H) 3.96-4.22 (m, 6 H) 5.09-5.46 (m, 1 H) 6.33-6.44 (m, 1 H) 6.52-6.78 (m, 1 H) 6.93-7.03 (m, 1 H) 7.22-7.34 (m, 1 H) 7.36-7.48 (m, 1 H) 7.72 (d, J = 15.03 Hz, 1 H) 8.03 (s, 1 H) 8.22 (s, 2 H) | 549.3 |
| 55 | 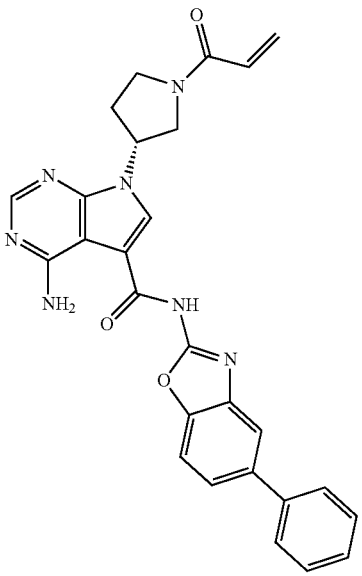 [SMILES: C=CC(=O)N1CC[C@@H](n2cc(C(=O)Nc3nc4cc(-c5ccccc5)ccc4o3)c3c(N)ncnc32)C1] | ¹H NMR (400 MHz, DMSO-d₆) δ ppm 2.36 (br. s., 1 H) 3.76 (br. s., 2 H) 3.91-4.09 (m 4 H) 5.26 (br. s., 1 H) 5.36 (br. s., 1 H) 5.64-5.73 (m, 2 H) 6.12-6.21 (m, 2 H) 6.62 (d, J = 9.57 Hz, 1 H) 7.29-7.38 (m, 3 H) 7.43 (d, J = 7.52 Hz, 6 H) 7.62 (d, J = 6.83 Hz, 4 H) 7.68 (br. s., 3 H) 7.90 (br. s., 2 H) 8.07 (s, 1 H) 8.21 (s, 2 H) | 494.3 |

TABLE 28

| Example No. | Structural Formula | NMR | mass |
|---|---|---|---|
| 56 | 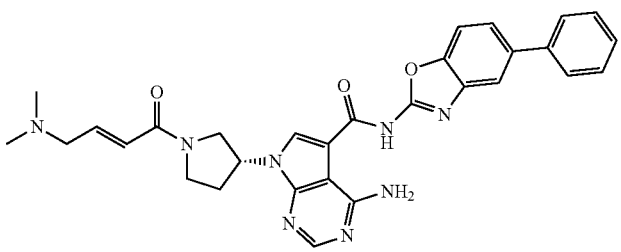 [SMILES: CN(C)C/C=C/C(=O)N1CC[C@@H](n2cc(C(=O)Nc3nc4cc(-c5ccccc5)ccc4o3)c3c(N)ncnc32)C1] | ¹H NMR (400 MHz, DMSO-d₆) δ ppm 2.11 (s, 3 H) 2.14 (s, 3 H) 2.35 (br. s., 1 H) 3.02 (dd, J = 17.08, 5.47 Hz, 2 H) 4.07 (br. s., 5 H) 5.14-5.41 (m, 1 H) 6.34-6.45 (m, 1 H) 6.56-6.72 (m, 1 H) 7.31 (br. s., 1 H) 7.43 (br. s., 2 H) 7.48 (br. s., 1 H) 7.63 (d, J = 5.47 Hz, 2 H) 7.71 (br. s., 1 H) 7.97 (br. s., 1 H) 8.06-8.11 (m, 1 H) 8.21 (s, 2 H) | 551.3 |

TABLE 28-continued

| Example No. | Structural Formula | NMR | mass |
|---|---|---|---|
| 57 | | ¹H NMR (400 MHz, DMSO-d₆) δ ppm 0.99 (dt, J = 10.93, 7.18 Hz, 3 H) 2.13 (s, 3 H) 2.29-2.45 (m, 2 H) 3.07-3.19 (m, 2 H) 4.10 (br. s., 1 H) 5.29 (br. s., 1 H) 5.38 (br. s., 1 H) 6.38-6.49 (m, 1 H) 6.64-6.74 (m, 1 H) 7.36 (d, J = 19.82 Hz, 2 H) 7.47 (br. s., 4 H) 7.65 (br. s., 2 H) 7.73 (br. s., 2 H) 7.93 (br. s., 1 H) 8.10 (s, 1 H) 8.26 (s, 2 H) | 565.3 |

TABLE 29

| Example No. | Structural Formula | NMR | mass |
|---|---|---|---|
| 58 | | ¹H NMR (400 MHz, DMSO-d₆) δ ppm 0.85-1.00 (m, 6 H) 2.35-2.45 (m, 4 H) 3.09-3.34 (m, 1 H) 3.17 (d, J = 10.93 Hz, 1 H) 4.06 (br. s., 1 H) 5.17-5.43 (m, 1 H) 6.36-6.47 (m, 1 H) 6.62-6.72 (m, 1 H) 7.27-7.38 (m, 1 H) 7.31 (s, 1 H) 7.36 (s, 1 H) 7.44 (br. s., 3 H) 7.62 (d, J = 6.15 Hz, 2 H) 7.70 (br. s., 1 H) 7.90 (br. s., 1 H) 8.07 (s, 1 H) 8.18-8.26 (m, 1 H) 8.22 (s, 2 H) | 579.3 |
| 59 | | ¹H NMR (400 MHz, DMSO-d₆) δ ppm 0.92 (dd, J = 11.28, 6.49 Hz, 6 H) 2.07 (d, J = 13.67 Hz, 3 H) 2.60-2.87 (m, 2 H) 3.13 (dd, J = 17.08, 5.47 Hz, 2 H) 4.06 (br. s., 1 H) 5.14-5.45 (m, 1 H) 6.28-6.50 (m, 1 H) 6.52-6.73 (m, 1 H) 7.29-7.39 (m, 3 H) 7.43 (br. s., 4 H) 7.62 (d, J = 6.83 Hz, 3 H) 7.70 (br. s., 2 H) 7.89 (br. s., 1 H) 8.07 (s, 1 H) 8.23 (s, 2 H) | 579.3 |

| Example No. | Structural Formula | NMR | mass |
|---|---|---|---|
| 60 | 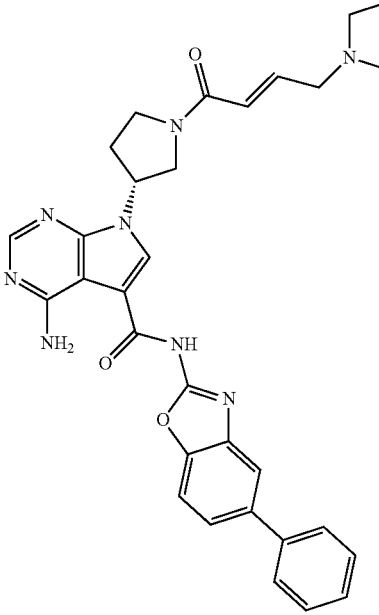 | $^1$H NMR (400 MHz, DMSO-d$_6$) δ ppm 1.60-1.72 (m, 4 H) 2.43 (d, J = 6.15 Hz, 4 H) 3.09-3.35 (m, 2 H) 4.07 (br. s., 1 H) 5.25 (br. s., 1 H) 5.34 (br. s., 1 H) 6.34-6.73 (m, 1 H) 7.31 (br. s., 1 H) 7.36 (br. s., 1 H) 7.43 (d, J = 6.83 Hz, 2 H) 7.61 (br. s., 2 H) 7.70 (br. s., 1 H) 7.91 (br. s., 1 H) 8.07 (s, 1 H) 8.22 (s, 2 H) | 577.3 |
| 61 | 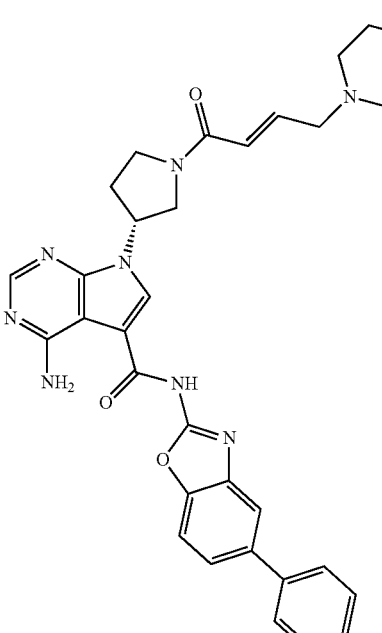 | $^1$H NMR (400 MHz, DMSO-d$_6$) δ ppm 1.34 (br. s., 2 H) 1.46 (br. s., 4 H) 2.29 (br. s., 4 H) 3.04 (dd, J = 17.43, 5.81 Hz, 2 H) 4.06 (br. s., 1 H) 5.20-5.40 (m, 1 H) 6.32-6.44 (m, 1 H) 6.59-6.68 (m, 1 H) 7.31 (br. s., 1 H) 7.37 (br. s., 1 H) 7.43 (d, J = 8.20 Hz, 2 H) 7.62 (d, J = 6.15 Hz, 2 H) 7.70 (br. s., 1 H) 7.92 (br. s., 1 H) 8.07 (s, 1 H) 8.22 (s, 2 H) | 591.4 |

TABLE 31

| Example No. | Structural Formula | NMR | mass |
|---|---|---|---|
| P-1 | (structure shown) | ¹H NMR (400 MHz, CHLOROFORM-d) δ ppm 1.19-1.46 (m, 1 H) 1.73 (br. s., 2 H) 1.98 (br. s., 3 H) 2.04 (s, 1 H) 2.27 (br. s., 2 H) 2.40 (d, J = 9.02 Hz, 1 H) 4.31 (br. s., 1 H) 4.94 (tt, J = 8.81, 4.24 Hz, 1 H) 5.09 (s, 1 H) 5.20 (br. s., 1 H) 6.58 (br. s., 1 H) 7.24-7.30 (m, 2 H) 7.45 (d, J = 8.78 Hz, 1 H) 7.68 (d, J = 1.95 Hz, 1 H) 8.34-8.42 (m, 1 H) 8.49 (br. s., 1 H) | |
| P-2 | (structure shown) | ¹H NMR (400 MHz, DMSO-d₆) δ ppm 0.04 (s, 1 H) 1.11-1.34 (m, 11 H) 1.39-1.61 (m, 9 H) 1.81-1.94 (m, 2 H) 1.95-2.08 (m, 5 H) 2.10-2.21 (m, 3 H) 2.54-2.58 (m, 3 H) 2.62-2.84 (m, 6 H) 3.47 (br. s., 6 H) 4.03-4.13 (m, 3 H) 4.22-4.30 (m, 2 H) 4.50-4.70 (m, 1 H) 6.33 (br. s., 1 H) 6.40 (br. s., 1 H) 6.46-6.70 (m, 2 H) 6.91-7.17 (m, 2 H) 7.29-7.41 (m, 2 H) 7.61-7.74 (m, 1 H) 7.80-7.93 (m, 1 H) 8.10-8.16 (m, 3 H) | 800.3 |

TABLE 32

| Example No. | Structural Formula | NMR | mass |
|---|---|---|---|
| Comparative Example Compound 1 | (structure shown) | ¹H NMR (400 MHz, DMSO-d₆) δ ppm 1.21-1.28 (m, 1 H) 1.42-1.71 (m, 1 H) 1.91 (br. s., 1H) 2.04-2.36 (m, 2 H) 2.91-3.10 (m, 1 H) 3.13-3.27 (m, 1 H) 3.59-3.76 (m, 1 H) 4.04-4.26 (m, 2 H) 4.47-4.80 (m, 2 H) 5.51-5.78 (m, 1 H) 5.96-6.21 (m, 1 H) 6.64-6.95 (m, 1 H) 7.14 (dd, J = 11.46, 8.54 Hz, 6 H) 7.40-7.47 7.63-7.70 (m, 2 H) 8.26 (s, 1 H) | 441.5 |

TABLE 33
| Example No. | Structural Formula | NMR | mass |
|---|---|---|---|
| 64 | | 1H NMR (400 MHz, DMSO-d6) δ ppm 1.87 (br. s., 2H), 2.04 (br. s., 2H), 2.18-2.33 (m, 2H), 3.88-4.75 (m, 4H), 4.61 (br. s., 2H), 5.63-5.73 (m, 1H), 5.71-5.72 (m, 1H), 6.04-6.15 (m, 2H), 6.69-6.93 (m, 1H), 7.00-7.12 (m, 1H), 7.02-7.09 (m, 3H), 8.23 (br. s., 3H), 10.79 (br. s., 2H) | 467.1 |
| 65 | | $^1$H NMR (400 MHz, DMSO-d$_6$) δ ppm 3.68-4.01 (m, 5H), 4.01-4.21 (m, 1H), 5.37-5.57 (m, 1H), 5.61-5.74 (m, 1H), 6.05-6.22 (m, 1H), 6.48-6.72 (m, 1H), 7.03-7.25 (m, 2H), 7.37-7.53 (m, 2H), 7.87-8.01 (m, 1H), 8.07-8.22 (m, 1H) | 419.2 |
TABLE 34
| Example No. | Structural Formula | NMR | mass |
|---|---|---|---|
| 66 | 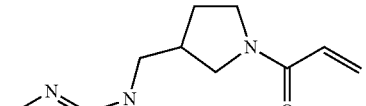 | 1H NMR (400 MHz, DMSO-d6) δ ppm 1.55-1.77 (m, 2H), 1.77-2.05 (m, 2H), 2.73-2.96 (m, 2H), 3.60-3.72 (m, 1H), 4.25-4.46 (m, 2H), 5.54-5.67 (m, 1H), 6.00-6.15 (m, 1H), 6.39-6.63 (m, 1H), 7.06-7.23 (m, 2H), 7.38-7.53 (m, 2H), 7.86-8.01 (m, 1H), 8.08-8.22 (m, 1H) | 433.2 |

TABLE 34-continued

| Example No. | Structural Formula | NMR | mass |
|---|---|---|---|
| 67 | | 1H NMR (400 MHz, DMSO-d6) δ ppm 1.12-1.36 (m, 2H), 1.50-1.77 (m, 2H), 1.99-2.21 (m, 1H), 3.79-3.90 (m, 2H), 3.94-4.17 (m, 2H), 4.19-4.35 (m, 2H), 5.50-5.66 (m, 1H), 5.92-6.08 (m, 1H), 6.58-6.81 (m, 1H), 6.98-7.22 (m, 2H), 7.29-7.50 (m, 2H), 7.76-7.91 (m, 1H), 8.05-8.20 (m, 2H) | 447.2 |

TABLE 35

| Example No. | Structural Formula | NMR | mass |
|---|---|---|---|
| 68 | | 1H NMR (400 MHz, DMSO-d6) δ ppm 1.00-1.26 (m, 2H), 1.42-1.60 (m, 2H), 2.13-2.32 (m, 1H), 2.51-2.68 (m, 1H), 2.90-3.03 (m, 1H), 3.91-4.09 (m, 1H), 4.16-4.27 (m, 2H), 4.28-4.42 (m, 1H), 5.55-5.67 (m, 1H), 5.97-6.09 (m, 1H), 6.66-6.85 (m, 1H), 7.00-7.17 (m, 2H), 7.31-7.45 (m, 2H), 7.74-7.88 (m, 1H), 8.03-8.22 (m, 2H) | 447.2 |
| 69 | | 1H NMR (400 MHz, DMSO-d6) δ ppm 1.86-2.08 (m, 4H), 2.79-2.94 (m, 1H), 4.13-4.28 (m, 1H), 4.45-4.58 (m, 1H), 4.88-5.05 (m, 1H), 5.62-5.73 (m, 1H), 6.07-6.17 (m, 1H), 6.75-6.95 (m, 1H), 6.97-7.15 (m, 2H), 7.28-7.46 (m, 2H), 7.74-7.83 (m, 1H), 8.06-8.16 (m, 1H), 8.16-8.25 (m, 1H) | 433.2 |

TABLE 36
| Example No. | Structural Formula | NMR | mass |
|---|---|---|---|
| 70 | 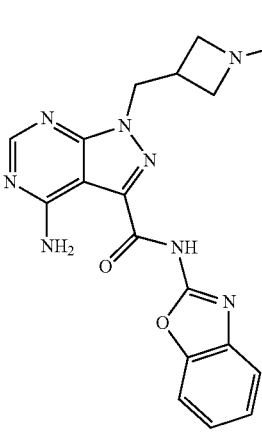 | 1H NMR (400 MHz, DMSO-d6) δ ppm 3.04-3.08 (m, 1H), 3.76-3.87 (m, 1H), 3.91-4.00 (m, 1H), 4.04-4.14 (m, 1H), 4.20-4.31 (m, 1H), 4.52-4.61 (m, 2H), 5.56-5.68 (m, 1H), 5.99-6.11 (m, 1H), 6.17-6.33 (m, 1H), 7.06-7.23 (m, 2H), 7.38-7.52 (m, 2H), 7.87-7.99 (m, 1H), 8.07-8.21 (m, 2H) | 419.3 |
| 71 | 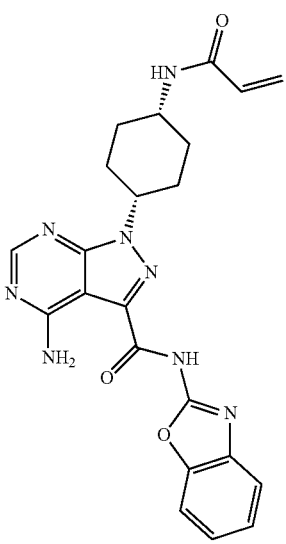 [SMILES: C=CC(=O)N[C@H]1CC[C@@H](n2nc(C(=O)Nc3nc4ccccc4o3)c3c(N)ncnc32)CC1] | 1H NMR (400 MHz, DMSO-d6) δ ppm 1.62-1.81 (m, 4H), 1.81-1.96 (m, 2H), 2.14-2.33 (m, 2H), 3.88-3.99 (m, 1H), 4.62-4.74 (m, 1H), 5.50-5.62 (m, 1H), 6.01-6.14 (m, 1H), 6.33-6.48 (m, 1H), 6.95-7.18 (m, 2H), 7.27-7.46 (m, 2H), 7.67-7.83 (m, 1H), 8.05-8.11 (m, 1H), 8.11-8.23 (m, 3H), 10.67-10.90 (m, 1H) | 447.2 |

TABLE 37
| Example No. | Structural Formula | NMR | mass |
|---|---|---|---|
| 72 | 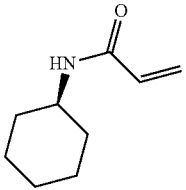 | 1H NMR (400 MHz, DMSO-d6) δ ppm 1.33-1.52 (m, 2H), 1.90-2.04 (m, 4H), 2.04-2.18 (m, 2H), 3.63-3.80 (m, 1H), 4.62-4.80 (m, 1H), 5.50-5.60 (m, 1H), 6.01-6.14 (m, 1H), 6.14-6.27 (m, 1H), 7.14-7.35 (m, 2H), 7.49-7.60 (m, 2H), 7.97-8.16 (m, 2H), 8.16-8.27 (m, 1H) | 447.2 |
| 73 | 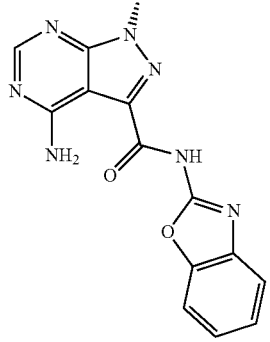 | 1H NMR (400 MHz, DMSO-d6) δ ppm 2.56-2.70 (m, 8H), 3.57-3.76 (m, 2H), 3.76-3.91 (m, 2H), 3.91-4.05 (m, 1H), 4.09-4.22 (m, 1H), 5.44-5.62 (m, 1H), 6.54-6.70 (m, 2H), 7.21-7.45 (m, 2H), 7.47-7.68 (m, 2H), 8.10 (s, 1H), 8.14-8.25 (m, 1H), 8.25-8.30 (m, 1H) | 476.3 |
TABLE 38
| Example No. | Structural Formula | NMR | mass |
|---|---|---|---|
| 74 | 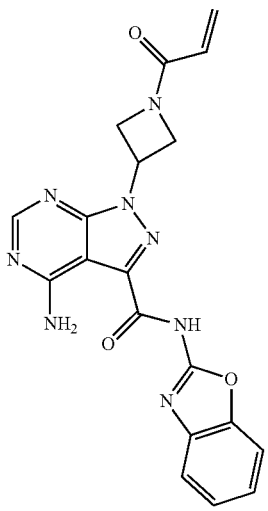 [SMILES: C=CC(=O)N1CC(n2nc(C(=O)Nc3nc4ccccc4o3)c3c(N)ncnc32)C1] | No data | 405.2 |

TABLE 38-continued

| Example No. | Structural Formula | NMR | mass |
|---|---|---|---|
| 75 | | 1H NMR (400 MHz, DMSO-d6) δ ppm 3.10-3.19 (m, 1H), 3.80-3.92 (m, 1H), 3.93-4.03 (m, 1H), 4.09-4.17 (m, 1H), 4.23-4.34 (m, 1H), 4.55-4.66 (m, 2H), 5.57-5.66 (m, 1H), 5.98-6.11 (m, 1H), 6.17-6.33 (m, 1H), 7.03-7.16 (m, 1H), 7.38-7.52 (m, 1H), 7.38-7.52 (m, 1H), 7.55-7.68 (m, 1H), 8.05-8.21 (m, 1H), 8.22-8.31 (m, 1H) | 437.2 |

TABLE 39

| Example No. | Structural Formula | NMR | mass |
|---|---|---|---|
| 76 | | 1H NMR (400 MHz, DMSO-d6) δ ppm 3.11-3.19 (m, 1H), 3.81-4.03 (m, 2H), 4.06-4.18 (m, 1H), 4.22-4.33 (m, 1H), 4.57-4.64 (m, 2H), 5.56-5.69 (m, 1H), 5.99-6.11 (m, 1H), 6.16-6.32 (m, 1H), 7.23-7.34 (m, 1H), 7.50-7.71 (m, 2H), 8.05-8.18 (m, 1H), 8.20-8.31 (m, 1H) | 453.2 |
| 77 | | 1H NMR (400 MHz, DMSO-d6) δ ppm 1.04-1.32 (m, 2H), 1.45-1.62 (m, 2H), 2.19-2.36 (m, 1H), 2.50-2.64 (m, 1H), 2.90-3.03 (m, 1H), 3.93-4.07 (m, 1H), 4.25-4.43 (m, 3H), 5.55-5.67 (m, 1H), 5.96-6.10 (m, 1H), 6.67-6.84 (m, 1H), 7.05-7.15 (m, 1H), 7.37-7.55 (m, 1H), 7.60-7.70 (m, 1H), 8.03-8.19 (m, 1H), 8.19-8.29 (m, 1H) | 465.3 |

TABLE 40
| Example No. | Structural Formula | NMR | mass |
| --- | --- | --- | --- |
| 78 | 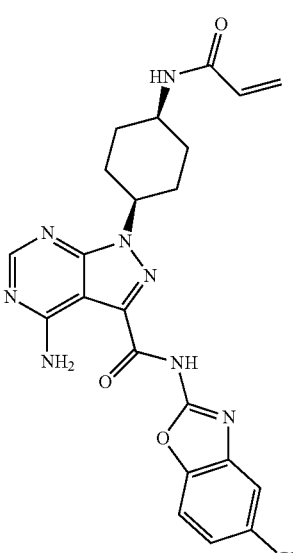 | 1H NMR (400 MHz, DMSO-d6) δ ppm 1.66-1.93 (m, 6H), 2.20-2.37 (m, 2H), 3.85-3.99 (m, 1H), 4.67-4.79 (m, 1H), 5.51-5.62 (m, 1H), 6.00-6.15 (m, 1H), 6.32-6.46 (m, 1H), 7.18-7.36 (m, 1H), 7.51-7.68 (m, 1H), 7.95-8.29 (m, 3H) | 481.2 |
| 79 | 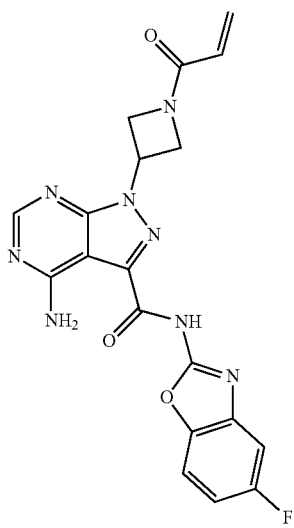 [SMILES: C=CC(=O)N1CC(n2nc(C(=O)Nc3nc4cc(F)ccc4o3)c3c(N)ncnc32)C1] | 1H NMR (400 MHz, DMSO-d6) δ ppm 4.35-4.60 (m, 2H), 4.63-4.81 (m, 2H), 5.63-5.81 (m, 2H), 6.09-6.20 (m, 1H), 6.28-6.44 (m, 1H), 6.93-7.15 (m, 1H), 7.34-7.50 (m, 1H), 7.54-7.66 (m, 1H), 8.07-8.28 (m, 2H) | 423.2 |

TABLE 41
| Example No. | Structural Formula | NMR | mass |
|---|---|---|---|
| 80 | 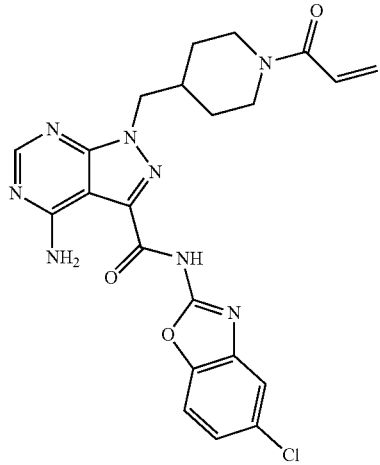 [SMILES: C=CC(=O)N1CCC(Cn2nc(C(=O)Nc3nc4cc(Cl)ccc4o3)c3c(N)ncnc32)CC1] | 1H NMR (400 MHz, DMSO-d6) δ ppm 1.00-1.37 (m, 2H), 1.41-1.64 (m, 2H), 2.18-2.32 (m, 1H), 2.53-2.65 (m, 1H), 2.90-3.02 (m, 1H), 3.93-4.06 (m, 1H), 4.23-4.39 (m, 3H), 5.54-5.67 (m, 1H), 5.95-6.10 (m, 1H), 6.62-6.79 (m, 1H), 7.21-7.32 (m, 1H), 7.55-7.70 (m, 2H), 8.01-8.15 (m, 1H), 8.15-8.23 (m, 1H) | 481.2 |
| 81 | 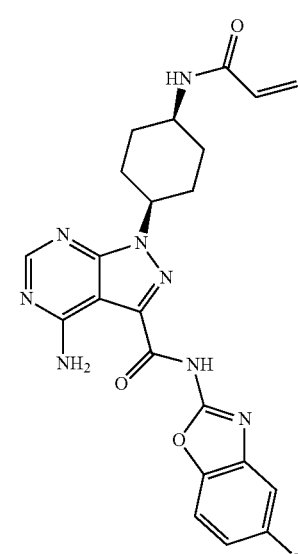 | 1H NMR (400 MHz, DMSO-d6) δ ppm 1.63-1.96 (m, 6H), 2.19-2.38 (m, 2H), 3.87-3.97 (m, 1H), 4.68-4.78 (m, 1H), 5.51-5.59 (m, 1H), 6.01-6.13 (m, 1H), 6.32-6.45 (m, 1H), 6.93-7.09 (m, 1H), 7.30-7.45 (m, 1H), 7.48-7.63 (m, 1H), 7.90-8.07 (m, 1H), 8.08-8.14 (m, 1H), 8.14-8.22 (m, 1H) | 465.2 |

TABLE 42
| Example No. | Structural Formula | NMR | mass |
|---|---|---|---|
| 82 | 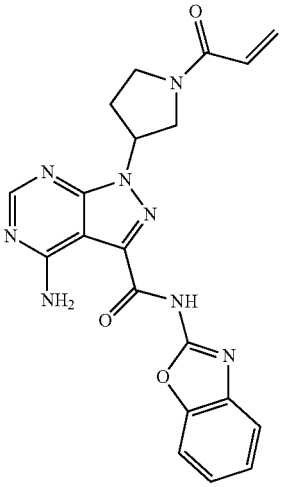 [SMILES: C=CC(=O)N1CCC(n2nc(C(=O)Nc3nc4ccccc4o3)c3c(N)ncnc32)C1] | 1H NMR (400 MHz, DMSO-d6) δ ppm 2.30-2.41 (m, 1H), 2.50-2.58 (m, 1H), 3.53-3.69 (m, 1H), 3.69-4.17 (m, 4H), 5.40-5.58 (m, 1H), 5.58-5.72 (m, 1H), 6.06-6.21 (m, 1H), 6.47-6.69 (m, 1H), 7.14-7.31 (m, 2H), 7.45-7.62 (m, 2H), 7.93-8.12 (m, 1H), 8.17-8.23 (m, 1H) | 419.2 |
| 83 | 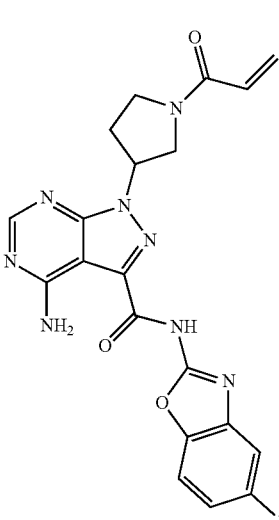 | 1H NMR (400 MHz, DMSO-d6) δ ppm 2.25-2.39 (m, 1H), 2.52-2.62 (m, 1H), 3.51-3.66 (m, 1H), 3.68-4.19 (m, 5H), 5.40-5.58 (m, 1H), 5.58-5.73 (m, 1H), 6.07-6.20 (m, 1H), 6.49-6.72 (m, 1H), 6.96-7.14 (m, 1H), 7.29-7.45 (m, 1H), 7.45-7.64 (m, 1H), 7.98-8.13 (m, 1H), 8.17-8.29 (m, 1H) | 437.2 |

… 145 146

TABLE 43

| Example No. | Structural Formula | NMR | mass |
| --- | --- | --- | --- |
| 84 | | 1H NMR (400 MHz, DMSO-d6) δ ppm 2.26-2.41 (m, 1H), 2.50-2.58 (m, 1H), 3.52-3.65 (m, 1H), 3.68-4.20 (m, 4H), 5.36-5.58 (m, 1H), 5.58-5.74 (m, 1H), 6.07-6.17 (m, 1H), 6.47-6.71 (m, 1H), 7.06-7.21 (m, 1H), 7.44-7.63 (m, 2H), 7.95-8.07 (m, 1H), 8.07-8.14 (m, 1H), 8.14-8.23 (m, 1H) | 453.3 |
| 85 | | 1H NMR (400 MHz, DMSO-d6) δ ppm 1.97-2.11 (m, 2H), 3.06-3.19 (m, 2H), 4.04-4.14 (m, 1H), 4.34-4.45 (m, 2H), 5.50-5.60 (m, 1H), 6.00-6.10 (m, 1H), 6.13-6.24 (m, 1H), 7.18-7.34 (m, 2H), 7.50-7.63 (m, 2H), 7.99-8.26 (m, 3H) | 407.2 |

TABLE 44

| Example No. | Structural Formula | NMR | mass |
| --- | --- | --- | --- |
| 86 | | 1H NMR (400 MHz, DMSO-d6) δ ppm 3.55-3.65 (m, 2H), 4.29-4.43 (m, 2H), 5.46-5.58 (m, 1H), 5.93-6.16 (m, 2H), 7.00-7.15 (m, 2H), 7.29-7.48 (m, 2H), 7.72-7.87 (m, 1H), 8.03-8.30 (m, 3H) | 393.2 |

Test Example 1

Measurement of BTK Inhibitory Activity (In Vitro)

With regard to the setting of the conditions for a method for measuring the inhibitory activity of a compound against BTK kinase activity in vitro, it is described in the consumable reagent supplies price list for LabChip (registered trademark) series of PerkinElmer, Inc. that FL-PEPTIDE 2 corresponds to a substrate peptide for the measurement of BTK kinase activity. Therefore, FL-PEPTIDE 2 was used as a substrate. The purified recombinant human BTK protein used in the test was purchased from Carna Biosciences, Inc.

With regard to the measurement of the inhibitory activity of the compounds, firstly, the compounds of the present invention were diluted stepwise with dimethyl sulfoxide (DMSO). Subsequently, BTK protein, a substrate peptide (final concentration was 1 μM), magnesium chloride (final concentration was 10 mM), ATP (final concentration was 45 μM), and a DMSO solution of the compounds of the present invention (final concentration of DMSO was 5%) were added to a buffer solution for kinase reaction (20 mM HEPES (pH 7.5), 2 mM dithiotheitol, 0.01% Triton X-100), and after the solution was incubated for 40 minutes at 25° C., a kinase reaction was carried out. The reaction was terminated by adding EDTA thereto in order to obtain a final concentration of 30 mM. Finally, a substrate peptide that was not phosphorylated (S) and a phosphorylated peptide (P) were separated and detected by microchannel capillary electrophoresis using a LabChip EZ Reader II (PerkinElmer, Inc.). The amounts of phosphorylation reaction were determined from the respective peak heights of S and P, and the compound concentration at which the phosphorylation reaction could be suppressed in 50% was defined as the IC50 value (nM). The results are indicated in the following tables.

TABLE 45

| Example No. | BTK inhibitory activity IC50 value (nM) |
|---|---|
| 1 | 0.415 |
| 2 | 0.464 |
| 3 | 0.443 |
| 4 | 0.888 |
| 5 | 1.253 |
| 6 | 0.738 |
| 7 | 0.457 |
| 8 | 1.266 |
| 9 | 1.37 |
| 10 | 2.384 |
| 11 | 2.143 |
| 12 | 0.433 |
| 13 | 0.813 |
| 14 | 14.141 |
| 15 | 0.786 |
| 16 | 0.733 |
| 17 | 0.811 |
| 18 | 0.788 |
| 19 | 0.69 |
| 20 | 0.801 |
| 21 | 0.777 |
| 22 | 14.209 |
| 23 | 1.583 |
| 24 | 0.591 |
| 25 | 1.166 |
| 26 | 2.788 |
| 27 | 1.433 |
| 28 | 0.559 |
| 29 | 0.485 |
| 30 | 0.566 |
| 31 | 1.671 |
| 32 | 0.634 |
| 33 | 0.887 |
| 34 | 0.79 |
| 35 | 0.792 |
| 36 | 0.867 |
| 37 | 0.786 |
| 38 | 0.888 |
| 39 | 1.12 |
| 40 | 2.087 |

TABLE 46

| Example No. | BTK inhibitory activity IC50 value (nM) |
|---|---|
| 41 | 0.442 |
| 42 | 0.771 |
| 43 | 0.546 |
| 44 | 0.877 |
| 45 | 1.249 |
| 46 | 3.272 |
| 47 | 7.345 |
| 48 | 0.836 |
| 49 | 1.529 |
| 50 | 1.407 |
| 51 | 1.48 |
| 52 | 1.195 |
| 53 | 1.675 |
| 54 | 1.436 |
| 55 | 0.799 |
| 56 | 1.337 |
| 57 | 1.507 |
| 58 | 1.844 |
| 59 | 1.507 |
| 60 | 1.88 |
| 61 | 2.341 |
| P-1 | 31.36 |
| P-2 | 43.882 |
| 64 | 8.09 |
| 65 | 79.03 |
| 66 | 16.98 |
| 67 | 14.04 |
| 68 | 13.16 |
| 69 | 161.78 |
| 70 | 3.17 |
| 71 | 5.89 |
| 72 | 28.11 |
| 73 | 258.63 |
| 74 | 21.4 |

From these test results, it was found that the compounds of the present invention have an inhibitory activity against BTK in vitro.

Test Example 2

BTK Inhibition Selectivity Compared with EGFR Kinase Inhibitory Activity (In Vitro)

1) Measurement of BTK Inhibitory Activity

The BTK inhibitory activity was measured in the same manner as in Test Example 1.

2) Measurement of EGFR Inhibitory Activity

With regard to the setting of the conditions for a method for measuring the inhibitory activity of a compound against EGFR kinase activity in vitro, it is described in the consumable reagent supplies price list for LabChip (registered trademark) series of PerkinElmer, Inc. that FL-PEPTIDE 22 corresponds to a substrate peptide for the measurement of EGFR kinase activity. Therefore, a biotinated peptide (biotin-EEPLYWSFPAKKK) was produced by referring to the amino acid sequence of the peptide. The purified recombinant human EGFR protein used in the test was purchased from Carna Biosciences, Inc.

With regard to the measurement of the inhibitory activity of the compounds, firstly, the compounds of the present invention were diluted stepwise with dimethyl sulfoxide (DMSO). Subsequently, EGFR protein, a substrate peptide (final concentration was 250 nM), magnesium chloride (final concentration was 10 mM), manganese chloride (final concentration was 10 mM), ATP (final concentration was 1.5 μM), and a DMSO solution of the compound of the present invention (final concentration of DMSO was 2.5%) were added to a buffer solution for kinase reaction (20 mM HEPES (pH 7.5), 2 mM dithiotheitol, 0.01% Triton X-100), and after the solution was incubated for 120 minutes at 25° C., a kinase reaction was carried out. The reaction was terminated by adding EDTA thereto in order to obtain a final concentration of 24 mM. Subsequently, a detection liquid containing Eu-labeled anti-phosphorylated tyrosine antibody PT66 (PerkinElmer, Inc.) and SURELIGHT APC-SA (PerkinElmer, Inc.) was added thereto, and the system was left to stand for 2 hours or longer at room temperature. Finally, the amount of fluorescence upon irradiation of excitation light having a wavelength of 337 nm was measured at two wavelengths of 620 nm and 665 nm, using a PHERAstar FS (BMG Labtech GmbH). The amount of phosphorylation reaction was determined from the ratio of the amounts of fluorescence at the two wavelengths, and the compound concentration at which the phosphorylation reaction could be suppressed in 50% was defined as the IC50 value (nM).

3) BTK Inhibition Selectivity

The "EGFR inhibitory activity IC50 value (nM)/BTK inhibitory activity IC50 value (nM)" was calculated based on the results obtained in the above sections 1) and 2), and thereby the BTK inhibition selectivity of the test compound was identified.

TABLE 47

| Example No. | EGFR inhibitory activity IC50 value (nM)/ BTK inhibitory activity IC50 value (nM) |
|---|---|
| 4 | 929.2 |
| 5 | 241.0 |
| 6 | 33.3 |
| 8 | 22.9 |
| 9 | 28.4 |
| 11 | 1294.6 |
| 12 | 84.2 |
| 13 | 28.8 |
| 14 | 128.1 |
| 15 | 145.0 |
| 16 | 158.1 |
| 17 | 157.2 |
| 18 | 121.3 |
| 19 | 144.8 |
| 20 | 138.2 |
| 21 | 147.4 |
| 22 | 260.1 |
| 25 | 173.7 |
| 26 | 642.8 |
| 30 | 21.3 |
| 32 | 43.1 |
| 33 | 43.4 |
| 34 | 79.3 |
| 35 | 35.1 |
| 36 | 59.8 |
| 37 | 70.5 |
| 39 | 37.5 |
| 40 | 10.0 |
| 42 | 19.4 |
| 44 | 17.1 |
| 47 | 20.4 |
| 49 | 24.8 |
| 50 | 22.1 |
| 51 | 31.1 |
| 52 | 20.6 |
| 53 | 25.5 |
| 54 | 37.1 |
| 56 | 17.6 |
| 57 | 19.3 |
| 58 | 23.5 |
| 59 | 16.3 |
| 60 | 32.4 |
| 61 | 67.5 |
| 67 | 18.0 |
| 68 | 11.4 |

TABLE 48

| Example No. | EGFR inhibitory activity IC50 value (nM)/ BTK inhibitory activity IC50 value (nM) |
|---|---|
| 70 | 12.2 |
| 71 | 42.0 |
| 72 | 12.4 |
| 73 | 11.2 |
| 75 | 58.2 |
| 76 | 11.4 |
| 77 | 203.7 |
| 78 | 100.7 |
| 79 | 20.6 |
| 80 | 75.4 |
| 81 | 204.9 |
| 82 | 10.9 |
| 83 | 39.6 |
| 85 | 11.0 |
| Comparative Example Compound 1 | 1.3 |

From these test results, it was made clear that the selectivity of the compound of the present invention to BTK inhibition over EGFR kinase in vitro was about 7.5 times or more compared with that of the Reference compound 1, and the compounds of the present invention have an excellent BTK inhibition selectivity. From these results, it was revealed that the compounds of the present invention could have reduced side effects compared with existing BTK inhibitors.

Test Example 3 Test for Measuring Proliferation Inhibitory Activity Against Cell Lines Expressing BTK and EGFR (In Vitro), and Comparison of its Selectivity TMD8 cells, which are of a diffuse large B-cell lymphoma cell line expressing BTK, were suspended in RPMI1640 medium (manufactured by Life Technologies Corp.) containing 10% fetal bovine serum. A431 cells, which are of an EGFR-overexpressing, highly activated human epidermoid carcinoma cell line, were suspended in DMEM, high glucose medium (manufactured by Life Technologies Corp.) containing 10% fetal bovine serum. The cell suspensions were inoculated into each well of 384-well flat-bottomed microplates, and the cells were cultured for 1 day at 37° C. in an incubator containing 5% carbon dioxide gas. The compounds of the present invention and Reference compound 1 were respectively dissolved in DMSO, and the solutions were diluted to a concentration of 500 times the final concentration of the test compound using DMSO. A DMSO solution of the test compounds was diluted with the medium used in the suspension of the each cells, and this was added to each of the wells of the cell culture plates such that the final concentration of DMSO would be 0.2%. The cells were further cultured for 3 days at 37° C. in an incubator containing 5% carbon dioxide gas. Counting of the number of cells before the addition of the compounds and after the culture for 3 days in the presence of the compounds, was carried out using a CELLTITER GLO (manufactured by Promega Corp.) based on the protocol recommended by Promega Corp. The proliferation inhibition ratio was calculated by the following formula, and the concentration of the test compound inhibiting 50% (GI50 (nM)) was determined.

Proliferation inhibition ratio (%)=$(C-T)/(C-C0)\times 100$

T: Luminescence intensity of a well in which the test compound was added

C: Luminescence intensity of a well in which the test compound was not added

C0: Luminescence intensity of a well measured before the addition of the test compound When a comparison is made between the cell proliferation inhibitory activity against A431 cells that depends on the EGFR proliferation signaling and the cell proliferation inhibitory activity against TMD8 cells that depends on the BTK proliferation signaling, the influence of the respective kinases at a cellular level is able to be evaluated. That is, when the "A431 cell proliferation inhibition ratio/TMD8 cell proliferation inhibition ratio" is calculated, it is contemplated that as the value of the ratio is larger, the selectivity to BTK over EGFR in the cells is higher. The values of "A431 cell proliferation inhibition ratio/TMD8 cell proliferation inhibition ratio" are indicated in Table 49 and Table 50.

TABLE 49

| Example No. | A431 cell proliferation inhibition ratio/TMD8 cell proliferation inhibitio ratio |
|---|---|
| 1 | 1062.9 |
| 2 | >1033.6 |
| 6 | 2786.0 |
| 7 | 5440.9 |
| 8 | 25303.8 |
| 9 | 8196.7 |
| 10 | 5860.5 |
| 12 | 3077.4 |
| 13 | 4872.2 |
| 14 | >1400.6 |
| 15 | 16442.0 |
| 16 | >16313.2 |
| 17 | >12345.7 |
| 18 | >15625.0 |
| 19 | >17825.3 |
| 20 | >19120.5 |
| 21 | 4909.1 |
| 22 | >12468.8 |
| 23 | >10680 |
| 24 | 3266.5 |
| 25 | 2793.0 |
| 27 | 4155.9 |
| 28 | 2040.3 |
| 29 | 1243.4 |
| 30 | 5164.3 |
| 32 | >11123.5 |
| 33 | >18281.5 |
| 34 | >22471.9 |
| 35 | >18691.6 |
| 38 | 2868.1 |
| 39 | >3510.0 |

TABLE 50

| Example No. | A431 cell proliferation inhibition ratio/TMD8 cell proliferation inhibitio ratio |
|---|---|
| 40 | >3159.6 |
| 41 | 1667.7 |
| 42 | 3934.1 |
| 44 | 10905.1 |
| 46 | 7662.2 |
| 48 | 2496.4 |
| 49 | >3260.5 |
| 50 | >2767.8 |
| 51 | >2044.6 |
| 52 | >3617.9 |
| 53 | >1535.4 |
| 54 | >2675.9 |
| 66 | >1205.7 |
| 67 | >2168.7 |
| 68 | >4785.8 |
| 70 | >8369.4 |
| 71 | >7657.0 |
| 72 | >2802.7 |
| 75 | >1643.7 |
| 76 | >2345.8 |
| 77 | >6793.5 |
| 78 | >23596.7 |
| 80 | 14348.9 |
| 81 | 8346.7 |
| 82 | 8143.0 |
| 83 | >18797.0 |
| 84 | >7132.7 |
| Comparative Example Compound 1 | 117.9 |

From these test results, it was made clear that the BTK inhibition selectivity of the compounds of the present invention over EGFR kinase in the cell proliferation inhibition ratio (in vitro) is about 8.5 times or more compared with the Reference compound 1, and the compounds of the present invention also have an excellent BTK inhibition selectivity not only in kinase levels but also in celler levels. From these results, it is revealed that the compounds of the present invention can have reduced side effects compared with existing BTK inhibitors.

Test Example 4

Antitumor Effect and Evaluation of Body Weight Change Ratio

Human B cell lymphoma-derived cell line TMD8 was subcutaneously transplanted into SCID mice. At the time point when the volume of engrafted tumors reached 100 to 200 mm$^3$, the mice were divided into groups, with 5 animals in each group, by a random classification method (Day 1) such that the tumor volumes in the various groups would be uniform, and oral administration was initiated. Group 1: Reference compound 1 (100 mg/kg) was orally administered once a day, Group 2: a compound of the present invention (Example compound 13) (50 mg/kg) was orally administered once a day, Group 3: a compound of the present invention (Example Compound 12) (50 mg/kg) was orally administered once a day, and Group 4: a compound of the present invention (Example Compound 6) (50 mg/kg) was orally administered once a day. In order to compare the antitumor effect caused by the drug administration, the relative tumor volume (RTV), which was the proliferation ratio of tumor when the tumor volume at the time of grouping was set as one, was determined by the following formula.

RTV=(Tumor volume on the day of tumor volume measurement)/(tumor volume at the time of grouping)

The average RTV values on 17 days after the administration in the control group and the compound-administered groups (Groups 1 to 4) are described in Table 51.

The body weight change (BWC) was used as an index indicating the systemic toxicity caused by drug administration. The BWC was calculated by the following formula, and the average BWC values are indicated in Table 38.

BWC (%)=([(mice body weight on the day of weight measurement)−(mice body weight at the time of grouping)]/(mice body weight at the time of grouping))×100 (Mathematical Formula 1)

TABLE 51

| Administered compound | Dose (mg/kg) | Day 17 RTV | BWC |
|---|---|---|---|
| Control | — | 9.36 | 8.5 |
| Group 1 | 100 | 3.21 | 2.0 |
| Group 2 | 50 | 4.24 | 3.8 |
| Group 3 | 50 | 0.13 | 6.0 |
| Group 4 | 50 | 1.99 | −0.6 |

As a result, the compounds of the present invention in a 50 mg/kg-administered group exhibited an antitumor effect equal to or higher than that of the group in which the Reference compound 1 was administered at a dose of 100 mg/kg. In addition, toxicity such as a decrease in body weight was not recognized in the groups administered these compounds.

Therefore, it is clear that the compounds of the present invention are compounds, which exhibit an excellent antitumor effect at lower doses compared with the Reference compound 1 and are highly safe.

Test Example 5

Influence on Body Weight of SD Rat by Repeated Administration with the Compounds of the Present Invention (In Vivo)

The influence on the increase in the body weight of SD rats by repeated administration with Reference compound 1 and the compounds of the present invention for two weeks, was compared with that of a vehicle-administered group. The rats were grouped as follows, with four animals in each group, by a random classification method such that the average body weights of the each groups would be almost uniform (Day 1).

Group 1: Reference compound 1 (280 mg/kg) was orally administered once a day, Group 2: a compound of the present invention (Example Compound 12) (750 mg/kg) was orally administered once a day, and Group 3: a compound of the present invention (Example Compound 13) (750 mg/kg) was orally administered once a day.

The body weight change (BWC) was used as an index indicating the systemic toxicity caused by drug administration. The BWC was calculated by the following formula.

BWC (%)=[[(Rat body weight on 14 days after the administration)−(rat body weight at the time of grouping)]/(rat body weight at the time of grouping))×100

The relative body weight change ratios in the each compound-administered groups were calculated by the following formula when the BWC in the vehicle-administered group was set as 1, and the results are indicated in Table 52.

Relative body weight change ratio (%)=(BWC in the compound-administered group)/(BWC in the vehicle-administered group)×100

TABLE 52

| Group | Dose (mg/kg) | Relative body weight ratio (%) |
|---|---|---|
| Group 1 | 280 | 30.9 |
| Group 2 | 750 | 91.2 |
| Group 3 | 750 | 79.1 |

According to the results, the width of rat body weight increase was very small in Group 1, which was the Reference compound 1-administered group compared with the vehicle-administered group. Whereas in Groups 2 and 3, which were the groups administered the compounds of the present invention, the increase of the rat body weight was hardly affected. The compounds of the present invention were administered with a 2.5-fold or more the amount of the Reference compound 1 (an approximately 5-fold amount in terms of $AUC_{0-24}$ (μM: hr)). Furthermore, in Group 1, individuals suffering from loose bowel were recognized; however, in Groups 2 and 3, no such individuals were recognized. Therefore, the compounds of the present invention have an excellent effect that the level of side effects is low despite that the amount of exposure is far larger than that of the Reference compound 1.

As described above, it was made clear that the compounds of the present invention are compounds having superior profiles with reduced toxicity compared with the Reference compound 1.

Test Example 6

Detection by BTK Labeling Using Fluorescent Labeling Compound (In Vitro)

The human B-cell lymphoma-derived cell line, Ramos cells were suspended in RPMI1640 medium containing 10% bovine serum, and then the cells were inoculated in a culture plate at a concentration of $2.0 \times 10^6$ (cells/well). The cells were cultured in a $CO_2$ incubator (Sanyo Electric Biomedical Co., Ltd.) at 37° C. for 24 hours. Example Compound P-1 and fluorescent labeled compounds which is a derivative of Reference compound 1(PCI-33380, Non-Patent Document 2) (10 mM stock) were respectively diluted with DMSO. Each of the dilutions was added to the plate inoculated cells, and the cells were cultured in a $CO_2$ incubator for 1 hour. Thereafter, the cells were harvested, and 50 μl of (a cell extract (NP-40; Invitrogen, Inc.) containing 1× protease inhibitor (Hoffmann-La Roche AG) and 1× phosphatase cocktail (Sigma-Aldrich Co.)) was added to the cell pellets. The cell pellets were left to stand for 10 minutes on ice. The amount of protein in the collected cell extract was quantitatively analyzed by a DC protein assay (Bio-Rad Laboratories, Inc.), and 20 μg of proteins per lane was applied to a SDS-concentration gradient gel (4% to 20%) (Wako Pure Chemical Industries, Ltd.). After electrophoresis was performed, images of electrophoretic gels were taken using a Molecular Dynamics Typhoon Scanner (GE Healthcare, Inc.). Thereafter, Western blotting was performed using an i-Blot (Invitrogen, Inc.), and BTK protein was detected with a LAS4000 (GE Healthcare, Inc.) using a BTK antibody (Abcam) (FIG. 1).

As shown in FIG. 1, it was made clear that the probe according to the present invention is a useful tool for detecting BTK in an in vitro test.

The invention claimed is:

1. A compound of formula (I):

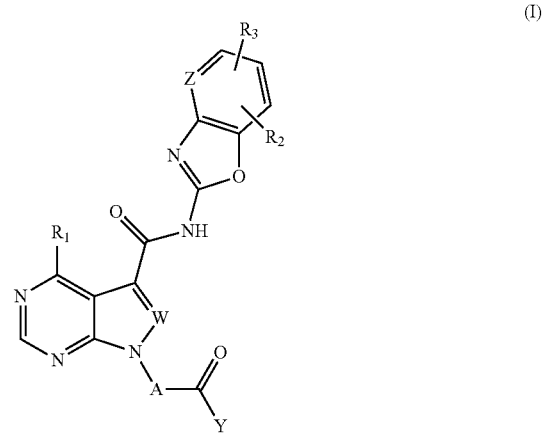

wherein A is —(CH$_2$)$_n$—X—, —(CH$_2$)$_m$—NH—, or —(C3-C7 cycloalkylene)-NH—;

n is an integer from 0 to 2;

m is an integer from 1 to 4;

X is a nitrogen-containing C3-C10 heterocycloalkylene which optionally has one or more substituents;

Y is —C(R$_4$)=C(R$_5$)(R$_6$) or —C≡C—R$_7$;

W and Z is each independently N or CH;

R$_1$ is an amino group;

R$_2$ and R$_3$, which are identical or different, each represent a hydrogen atom, a halogen atom, a C1-C6 alkyl group which optionally has one or more substituents, a C1-C6 alkoxy group which optionally has one or more substituents, a C3-C7 cycloalkyl group which optionally has one or more substituents, a C6-C14 aromatic hydrocarbon group which optionally has one or more substituents, a 4-membered to 10-membered monocyclic or polycyclic unsaturated heterocyclic group containing 1 to 3 heteroatoms of the same kind or different kinds selected from a nitrogen atom, an oxygen atom and a sulfur atom, which optionally has one or more substituents, or a cyano group; and R$_4$, R$_5$, R$_6$ and R$_7$, which are identical or different, each represent a hydrogen atom, or a C1-C6 alkyl group which optionally has one or more substituents, or a salt thereof.

2. The compound of claim 1, wherein in the formula (I),

A is —(CH$_2$)$_n$—X—;

n is 0; and

X is a nitrogen-containing C3-C10 heterocycloalkylene, or a salt thereof.

3. The compound of claim 1, wherein in the formula (I),

A is —(CH$_2$)$_n$—X—;

n is 0; and

X is azetidinylene, pyrrolidinylene, or piperidinylene, or a salt thereof.

4. The compound of claim 1, wherein in the formula (I),

A is —(CH$_2$)$_n$—X—;

n is 0;

X is azetidinylene, pyrrolidinylene, or piperidinylene;

one of R$_2$ and R$_3$ is a hydrogen atom or a C1-C6 alkyl group, and the other is a hydrogen atom, a halogen atom, a C1-C6 alkyl group, a halogeno-C1-C6 alkyl group, a C1-C4 alkoxy-substituted C1-C6 alkyl group, a C1-C6 alkoxy group, a phenyl group which optionally has one or more substituents with a halogen atom, a 4-membered to 6-membered monocyclic unsaturated heterocyclic group containing one sulfur atom, or a cyano group;

R$_4$, R$_5$ and R$_6$, which are identical or different, each represent a hydrogen atom, a C1-C6 alkyl group, a C1-C6 alkyl group that is substituted with an amino group substituted with two C1-C6 alkyl groups, where the C1-C6 alkyl groups optionally form a 4-membered to 8-membered heterocycloalkyl group together with the nitrogen atom to which the C1-C6 alkyl groups are bonded; and R$_7$ is a hydrogen atom or a C1-C6 alkyl group, or a salt thereof.

5. The compound of claim 1, wherein in the formula (I),

A is —(CH$_2$)$_n$—X—;

n is 0;

X is 1,3-azetidinylene, 1,3-pyrrolidinylene, or 1,3-piperidinylene;

Z is N and W is N, or Z is CH and W is N or CH;

one of R$_2$ and R$_3$ is a hydrogen atom or a C1-C4 alkyl group, and the other is a hydrogen atom, a halogen atom, a C1-C4 alkyl group, a halogeno-C1-C4 alkyl group, a C1-C4 alkoxy-substituted C1-C4 alkyl group, a C1-C4 alkoxy group, a phenyl group optionally has one or more substituents with a halogen atom, a 4-membered to 6-membered monocyclic unsaturated heterocyclic group containing one sulfur atom, or a cyano group;

R$_4$, R$_5$ and R$_6$, which are identical or different, each represent a hydrogen atom, a C1-C6 alkyl group, a C1-C6 alkyl group that is substituted with an amino group substituted with two C1-C6 alkyl groups, where the C1-C6 alkyl groups optionally form a 4-membered to 8-membered heterocycloalkyl group together with the nitrogen atom to which the C1-C6 alkyl groups are bonded; and R$_7$ is a hydrogen atom or a C1-C4 alkyl group, or a salt thereof.

6. The compound of claim 1, wherein in the formula (I),

A is —(CH$_2$)$_n$—X—;

n is 0;

X is 1,3-azetidinylene, 1,3-pyrrolidinylene, or 1,3-piperidinylene;

Z is N and W is N, or Z is CH and W is N or CH;

one of R$_2$ and R$_3$ is a hydrogen atom or a methyl group, and the other is a hydrogen atom, a halogen atom, a methyl group, a trifluoromethyl group, a methoxyethyl group, a methoxy group, a phenyl group, a 4-chlorophenyl group, a 2-thienyl group, or a cyano group;

R$_4$, R$_5$ and R$_6$, which are identical or different, each represent a hydrogen atom, a methyl group, a dimethylaminomethyl group, a methylethylaminomethyl group, a diethylaminomethyl group, a methylisopropylaminomethyl group, a 1-piperidinylmethyl group, or a 1-pyrrolidinylmethyl group; and R$_7$ represents a methyl group, or a salt thereof.

7. The compound of claim 1, wherein in the formula (I),

A is —(CH$_2$)$_n$—X—;

n is 0, one of R$_2$ and R$_3$ is a hydrogen atom or a methyl group, and the other is a hydrogen atom, a halogen atom, a trifluoromethyl group, a methoxyethyl group, a phenyl group, a 2-thienyl group, or a cyano group; and (1) Z is N, W is N, X is 1,3-piperidinylene, and Y is a vinyl group;

(2) Z is CH, W is N, X is 1,3-pyrrolidinylene or 1,3-piperidinylene, and Y is —C(R$_4$)=C(R$_5$)(R$_6$) or —C≡C—(R$_7$), where R$_4$, R$_5$ and R$_6$, which are identical or different, each represent a hydrogen atom, a methyl group, a dimethylaminomethyl group, a methyl ethyl aminomethyl group, a diethylaminomethyl group, a methylisopropylaminomethyl group, a 1-piperidinylmethyl group, or a 1-pyrrolidinylmethyl group, and R$_7$ is a methyl group; or (3) Z is CH, W is CH, X is 1,3-azetidinylene or 1,3-pyrrolidinylene, and Y is —C(R$_4$)=C(R$_5$)(R$_6$), where R$_4$, R$_5$ and R$_6$, which are identical or different, each represent a hydrogen atom, a dimethylaminomethyl group, a methylethylaminomethyl group, a diethylaminomethyl group, a methylisopropylaminomethyl group, a 1-piperidinylmethyl group, or a 1-pyrrolidinylmethyl group, or a salt thereof.

8. The compound of claim 1, wherein in the formula (I),

A is —(CH$_2$)$_n$—X—;

n is 0;

X is 1,3-piperidinylene;

Y is a vinyl group;

Z is CH;
W is N; and
one of R₂ and R₃ is a hydrogen atom, and the other is a hydrogen atom, a halogen atom, or a cyano group, or a salt thereof.

9. The compound of claim 1, wherein the compound of the formula (I) is selected from the group consisting of:
(1) (R)-1-(1-acryloylpiperidin-3-yl)-4-amino-N-(5-chlorobenzo[d]oxazol-2-yl)-1H-pyrazolo[3,4-d]pyrimidine-3-carboxamide,
(2) (R)-1-(1-acryloylpiperidin-3-yl)-4-amino-N-(5-bromobenzo[d]oxazol-2-yl)-1H-pyrazolo[3,4-d]pyrimidine-3-carboxamide,
(3) (R)-1-(1-acryloylpiperidin-3-yl)-4-amino-N-(5-(thiophen-2-yl)benzo[d]oxazol-2-yl)-1H-pyrazolo[3,4-d]pyrimidine-3-carboxamide,
(4) (R)-4-amino-N-(5-chlorobenzo[d]oxazol-2-yl)-1-(1-methacryloylpiperidin-3-yl)-1H-pyrazolo[3,4-d]pyrimidine-3-carboxamide,
(5) (R,E)-4-amino-N-(5-chlorobenzo[d]oxazol-2-yl)-1-(1-(but-2-enoyl)piperidin-3-yl)-1H-pyrazolo[3,4-d]pyrimidine-3-carboxamide,
(6) (R)-1-(1-acryloylpiperidin-3-yl)-4-amino-N-(5-cyanobenzo[d]oxazol-2-yl)-1H-pyrazolo[3,4-d]pyrimidine-3-carboxamide,
(7) (R)-1-(1-acryloylpiperidin-3-yl)-4-amino-N-(5-methoxybenzo[d]oxazol-2-yl)-1H-pyrazolo[3,4-d]pyrimidine-3-carboxamide,
(8) (R)-1-(1-acryloylpiperidin-3-yl)-4-amino-N-(5-(2-methoxyethyl)benzo[d]oxazol-2-yl)-1H-pyrazolo[3,4-d]pyrimidine-3-carboxamide,
(9) (R)-1-(1-acryloylpiperidin-3-yl)-4-amino-N-(oxazolo[4,5-b]pyridin-2-yl)-1H-pyrazolo[3,4-d]pyrimidine-3-carboxamide,
(10) (R)-1-(1-acryloylpiperidin-3-yl)-4-amino-N-(4-methylbenzo[d]oxazol-2-yl)-1H-pyrazolo[3,4-d]pyrimidine-3-carboxamide,
(11) (R)-4-amino-N-(5-fluorobenzo[d]oxazol-2-yl)-1-(1-methacryloylpiperidin-3-yl)-1H-pyrazolo[3,4-d]pyrimidine-3-carboxamide,
(12) (R)-1-(1-acryloylpiperidin-3-yl)-4-amino-N-(5-fluorobenzo[d]oxazol-2-yl)-1H-pyrazolo[3,4-d]pyrimidine-3-carboxamide,
(13) (R)-1-(1-acryloylpiperidin-3-yl)-4-amino-N-(benzo[d]oxazol-2-yl)-1H-pyrazolo[3,4-d]pyrimidine-3-carboxamide,
(14) (R,E)-4-amino-N-(benzo[d]oxazol-2-yl)-1-(1-(but-2-enoyl)piperidin-3-yl)-1H-pyrazolo[3,4-d]pyrimidine-3-carboxamide,
(15) (R,E)-4-amino-N-(5-chlorobenzo[d]oxazol-2-yl)-1-(1-(4-(dimethylamino)but-2-enoyl)piperidin-3-yl)-1H-pyrazolo[3,4-d]pyrimidine-3-carboxamide,
(16) (R,E)-4-amino-N-(5-chlorobenzo[d]oxazol-2-yl)-1-(1-(4-(ethyl(methyl)amino)but-2-enoyl)piperidin-3-yl)-1H-pyrazolo[3,4-d]pyrimidine-3-carboxamide,
(17) (R,E)-4-amino-N-(5-chlorobenzo[d]oxazol-2-yl)-1-(1-(4-(diethylamino)but-2-enoyl)piperidin-3-yl)-1H-pyrazolo[3,4-d]pyrimidine-3-carboxamide,
(18) (R,E)-4-amino-N-(5-chlorobenzo[d]oxazol-2-yl)-1-(1-(4-(isopropyl(methyl)amino)but-2-enoyl)piperidin-3-yl)-1H-pyrazolo[3,4-d]pyrimidine-3-carboxamide,
(19) (R,E)-4-amino-N-(5-chlorobenzo[d]oxazol-2-yl)-1-(1-(4-(pyrrolidin-1-yl)but-2-enoyl)piperidin-3-yl)-1H-pyrazolo[3,4-d]pyrimidine-3-carboxamide,
(20) (R,E)-4-amino-N-(5-chlorobenzo[d]oxazol-2-yl)-1-(1-(4-(piperidin-1-yl)but-2-enoyl)piperidin-3-yl)-1H-pyrazolo[3,4-d]pyrimidine-3-carboxamide,
(21) (R,E)-4-amino-N-(5-(thiophen-2-yl)benzo[d]oxazol-2-yl)-1-(1-(4-(dimethylamino)but-2-enoyl)piperidin-3-yl)-1H-pyrazolo[3,4-d]pyrimidine-3-carboxamide,
(22) (R)-4-amino-N-(benzo[d]oxazol-2-yl)-1-(1-(but-2-ynoyl)piperidin-3-yl)-1H-pyrazolo[3,4-d]pyrimidine-3-carboxamide,
(23) (R)-1-(1-acryloylpiperidin-3-yl)-4-amino-N-(5,6-dimethylbenzo[d]oxazol-2-yl)-1H-pyrazolo[3,4-d]pyrimidine-3-carboxamide,
(24) (R)-1-(1-acryloylpyrrolidin-3-yl)-4-amino-N-(5-chlorobenzo[d]oxazol-2-yl)-1H-pyrazolo[3,4-d]pyrimidine-3-carboxamide,
(25) (R,E)-4-amino-N-(5-chlorobenzo[d]oxazol-2-yl)-1-(1-(but-2-enoyl)pyrrolidin-3-yl)-1H-pyrazolo[3,4-d]pyrimidine-3-carboxamide,
(26) (R,E)-4-amino-N-(5-chlorobenzo[d]oxazol-2-yl)-1-(1-(3-methylbut-2-enoyl)pyrrolidin-3-yl)-1H-pyrazolo[3,4-d]pyrimidine-3-carboxamide,
(27) (R)-1-(1-acryloylpyrrolidin-3-yl)-4-amino-N-(benzo[d]oxazol-2-yl)-1H-pyrazolo[3,4-d]pyrimidine-3-carboxamide,
(28) (R)-1-(1-acryloylpyrrolidin-3-yl)-4-amino-N-(5-(thiophen-2-yl)benzo[d]oxazol-2-yl)-1H-pyrazolo[3,4-d]pyrimidine-3-carboxamide,
(29) (R)-1-(1-acryloylpyrrolidin-3-yl)-4-amino-N-(5-methylbenzo[d]oxazol-2-yl)-1H-pyrazolo[3,4-d]pyrimidine-3-carboxamide,
(30) (R)-1-(1-acryloylpyrrolidin-3-yl)-4-amino-N-(5-fluorobenzo[d]oxazol-2-yl)-1H-pyrazolo[3,4-d]pyrimidine-3-carboxamide,
(31) (R)-1-(1-acryloylpyrrolidin-3-yl)-4-amino-N-(5-(4-chlorophenyl)benzo[d]oxazol-2-yl)-1H-pyrazolo[3,4-d]pyrimidine-3-carboxamide,
(32) (R,E)-4-amino-N-(5-chlorobenzo[d]oxazol-2-yl)-1-(1-(4-(dimethylamino)but-2-enoyl)pyrrolidin-3-yl)-1H-pyrazolo[3,4-d]pyrimidine-3-carboxamide,
(33) (R,E)-4-amino-N-(5-chlorobenzo[d]oxazol-2-yl)-1-(1-(4-(ethyl(methyl)amino)but-2-enoyl)pyrrolidin-3-yl)-1H-pyrazolo[3,4-d]pyrimidine-3-carboxamide,
(34) (R,E)-4-amino-N-(5-chlorobenzo[d]oxazol-2-yl)-1-(1-(4-(diethylamino)but-2-enoyl) pyrrolidin-3-yl)-1H-pyrazolo[3,4-d]pyrimidine-3-carboxamide,
(35) (R,E)-4-amino-N-(5-chlorobenzo[d]oxazol-2-yl)-1-(1-(4-(isopropyl(methyl)amino)but-2-enoyl)pyrrolidin-3-yl)-1H-pyrazolo[3,4-d]pyrimidine-3-carboxamide,
(36) (R,E)-4-amino-N-(5-chlorobenzo[d]oxazol-2-yl)-1-(1-(4-(pyrrolidin-1-yl)but-2-enoyl)pyrrolidin-3-yl)-1H-pyrazolo[3,4-d]pyrimidine-3-carboxamide,
(37) (R,E)-4-amino-N-(5-chlorobenzo[d]oxazol-2-yl)-1-(1-(4-(piperidin-1-yl)but-2-enoyl)pyrrolidin-3-yl)-1H-pyrazolo[3,4-d]pyrimidine-3-carboxamide,
(38) (R)-1-(1-acryloylpyrrolidin-3-yl)-4-amino-N-(5-methoxybenzo[d]oxazol-2-yl)-1H-pyrazolo[3,4-d]pyrimidine-3-carboxamide,
(39) (R)-1-(1-acryloylpyrrolidin-3-yl)-4-amino-N-(5-cyanobenzo[d]oxazol-2-yl)-1H-pyrazolo[3,4-d]pyrimidine-3-carboxamide,
(40) (R)-1-(1-acryloylpyrrolidin-3-yl)-4-amino-N-(5-(2-methoxyethyl)benzo[d]oxazol-2-yl)-1H-pyrazolo[3,4-d]pyrimidine-3-carboxamide,
(41) (R)-1-(1-acryloylpyrrolidin-3-yl)-4-amino-N-(5-phenylbenzo[d]oxazol-2-yl)-1H-pyrazolo[3,4-d]pyrimidine-3-carboxamide,
(42) (R,E)-4-amino-N-(5-phenylbenzo[d]oxazol-2-yl)-1-(1-(4-(dimethylamino)but-2-enoyl)pyrrolidin-3-yl)-1H-pyrazolo[3,4-d]pyrimidine-3-carboxamide,
(43) (R)-1-(1-acryloylpyrrolidin-3-yl)-4-amino-N-(5-(trifluoromethyl)benzo[d]oxazol-2-yl)-1H-pyrazolo[3,4-d]pyrimidine-3-carboxamide,

(44) (R,E)-4-amino-N-(5-(trifluoromethyl)benzo[d]oxazol-2-yl)-1-(1-(4-(dimethylamino)but-2-enoyl)pyrrolidin-3-yl)-1H-pyrazolo[3,4-d]pyrimidine-3-carboxamide,
(45) 1-(1-acryloylazetidin-3-yl)-4-amino-N-(5-chlorobenzo[d]oxazol-2-yl)-1H-pyrazolo[3,4-d]pyrimidine-3-carboxamide,
(46) 7-(1-acryloylazetidin-3-yl)-4-amino-N-(5-chlorobenzo[d]oxazol-2-yl)-7H-pyrrolo[2,3-d]pyrimidine-5-carboxamide,
(47) (E)-4-amino-N-(5-chlorobenzo[d]oxazol-2-yl)-7-(1-(4-(dimethylamino)but-2-enoyl)azetidin-3-yl) 7H-pyrrolo[2,3-d]pyrimidine-5-carboxamide,
(48) (R)-7-(1-acryloylpyrrolidin-3-yl)-4-amino-N-(5-chlorobenzo[d]oxazol-2-yl)-7H-pyrrolo[2,3-d]pyrimidine-5-carboxamide,
(49) (R,E)-4-amino-N-(5-chlorobenzo[d]oxazol-2-yl)-7-(1-(4-(dimethylamino)but-2-enoyl)pyrrolidin-3-yl) 7H-pyrrolo[2,3-d]pyrimidine-5-carboxamide,
(50) (R,E)-4-amino-N-(5-chlorobenzo[d]oxazol-2-yl)-7-(1-(4-(ethyl(methyl)amino)but-2-enoyl)pyrrolidin-3-yl) 7H-pyrrolo[2,3-d]pyrimidine-5-carboxamide,
(51) (R,E)-4-amino-N-(5-chlorobenzo[d]oxazol-2-yl)-7-(1-(4-(diethylamino)but-2-enoyl)pyrrolidin-3-yl) 7H-pyrrolo[2,3-d]pyrimidine-5-carboxamide,
(52) (R,E)-4-amino-N-(5-chlorobenzo[d]oxazol-2-yl)-7-(1-(4-(isopropyl(methyl)amino)but-2-enoyl)pyrrolidin-3-yl) 7H-pyrrolo[2,3-d]pyrimidine-5-carboxamide,
(53) (R,E)-4-amino-N-(5-chlorobenzo[d]oxazol-2-yl)-7-(1-(4-(pyrrolidin-1-yl)but-2-enoyl)pyrrolidin-3-yl) 7H-pyrrolo[2,3-d]pyrimidine-5-carboxamide,
(54) (R,E)-4-amino-N-(5-chlorobenzo[d]oxazol-2-yl)-7-(1-(4-(piperidin-1-yl)but-2-enoyl)pyrrolidin-3-yl) 7H-pyrrolo[2,3-d]pyrimidine-5-carboxamide,
(55) (R)-7-(1-acryloylpyrrolidin-3-yl)-4-amino-N-(5-phenylbenzo[d]oxazol-2-yl)-7H-pyrrolo[2,3-d]pyrimidine-5-carboxamide,
(56) (R,E)-4-amino-N-(5-phenylbenzo[d]oxazol-2-yl)-7-(1-(4-(dimethylamino)but-2-enoyl)pyrrolidin-3-yl) 7H-pyrrolo[2,3-d]pyrimidine-5-carboxamide,
(57) (R,E)-4-amino-N-(5-phenylbenzo[d]oxazol-2-yl)-7-(1-(4-(ethyl(methyl)amino)but-2-enoyl)pyrrolidin-3-yl) 7H-pyrrolo[2,3-d]pyrimidine-5-carboxamide,
(58) (R,E)-4-amino-N-(5-phenylbenzo[d]oxazol-2-yl)-7-(1-(4-(diethylamino)but-2-enoyl)pyrrolidin-3-yl) 7H-pyrrolo[2,3-d]pyrimidine-5-carboxamide,
(59) (R,E)-4-amino-N-(5-phenylbenzo[d]oxazol-2-yl)-7-(1-(4-(isopropyl(methyl)amino)but-2-enoyl)pyrrolidin-3-yl) 7H-pyrrolo[2,3-d]pyrimidine-5-carboxamide,
(60) (R,E)-4-amino-N-(5-phenylbenzo[d]oxazol-2-yl)-7-(1-(4-(pyrrolidin-1-yl)but-2-enoyl)pyrrolidin-3-yl) 7H-pyrrolo[2,3-d]pyrimidine-5-carboxamide,
(61) (R,E)-4-amino-N-(5-phenylbenzo[d]oxazol-2-yl)-7-(1-(4-(piperidin-1-yl)but-2-enoyl)pyrrolidin-3-yl) 7H-pyrrolo[2,3-d]pyrimidine-5-carboxamide,
(64) (R)-1-(1-acryloylpiperidin-3-yl)-4-amino-N-(7-chlorobenzo[d]oxazol-2-yl)-1H-pyrazolo[3,4-d]pyrimidine-3-carboxamide,
(65) (S)-1-(1-acryloylpyrrolidin-3-yl)-4-amino-N-(benzo[d]oxazol-2-yl)-1H-pyrazolo[3,4-d]pyrimidine-3-carboxamide,
(66) 1-((1-acryloylpyrrolidin-3-yl)methyl)-4-amino-N-(benzo[d]oxazol-2-yl)-1H-pyrazolo[3,4-d]pyrimidine-3-carboxamide,
(67) 1-((1-acryloylpiperidin-3-yl)methyl)-4-amino-N-(benzo[d]oxazol-2-yl)-1H-pyrazolo[3,4-d]pyrimidine-3-carboxamide,
(68) 1-((1-acryloylpiperidin-4-yl)methyl)-4-amino-N-(benzo[d]oxazol-2-yl)-1H-pyrazolo[3,4-d]pyrimidine-3-carboxamide,
(69) 1-(1-acryloylpiperidin-4-yl)-4-amino-N-(benzo[d]oxazol-2-yl)-1H-pyrazolo[3,4-d]pyrimidine-3-carboxamide,
(70) 1-((1-acryloylazetidin-3-yl)methyl)-4-amino-N-(benzo[d]oxazol-2-yl)-1H-pyrazolo[3,4-d]pyrimidine-3-carboxamide,
(71) 1-((1S,4S)-4-acrylamidocyclohexyl)-4-amino-N-(benzo[d]oxazol-2-yl)-1H-pyrazolo[3,4-d]pyrimidine-3-carboxamide,
(72) 1-((1R,4R)-4-acrylamidocyclohexyl)-4-amino-N-(benzo[d]oxazol-2-yl)-1H-pyrazolo[3,4-d]pyrimidine-3-carboxamide,
(73) (S,E)-4-amino-N-(benzo[d]oxazol-2-yl)-1-(1-(4-(dimethylamino)but-2-enoyl)pyrrolidin-3-yl)-1H-pyrazolo[3,4-d]pyrimidine-3-carboxamide,
(74) 1-(1-acryloylazetidin-3-yl)-4-amino-N-(benzo[d]oxazol-2-yl)-1H-pyrazolo[3,4-d]pyrimidine-3-carboxamide,
(75) 1-((1-acryloylazetidin-3-yl)methyl)-4-amino-N-(5-fluorobenzo[d]oxazol-2-yl)-1H-pyrazolo[3,4-d]pyrimidine-3-carboxamide,
(76) 1-((1-acryloylazetidin-3-yl)methyl)-4-amino-N-(5-chlorobenzo[d]oxazol-2-yl)-1H-pyrazolo[3,4-d]pyrimidine-3-carboxamide,
(77) 1-((1-acryloylpiperidin-4-yl)methyl)-4-amino-N-(5-fluorobenzo[d]oxazol-2-yl)-1H-pyrazolo[3,4-d]pyrimidine-3-carboxamide,
(78) 1-((1S,4S)-4-acrylamidocyclohexyl)-4-amino-N-(5-chlorobenzo[d]oxazol-2-yl)-1H-pyrazolo[3,4-d]pyrimidine-3-carboxamide,
(79) 1-(1-acryloylazetidin-3-yl)-4-amino-N-(5-fluorobenzo[d]oxazol-2-yl)-1H-pyrazolo[3,4-d]pyrimidine-3-carboxamide,
(80) 1-((1-acryloylpiperidin-4-yl)methyl)-4-amino-N-(5-chlorobenzo[d]oxazol-2-yl)-1H-pyrazolo[3,4-d]pyrimidine-3-carboxamide,
(81) 1-((1S,4S)-4-acrylamidocyclohexyl)-4-amino-N-(5-fluorobenzo[d]oxazol-2-yl)-1H-pyrazolo[3,4-d]pyrimidine-3-carboxamide,
(82) 1-(1-acryloylpyrrolidin-3-yl)-4-amino-N-(benzo[d]oxazol-2-yl)-1H-pyrazolo[3,4-d]pyrimidine-3-carboxamide,
(83) 1-(1-acryloylpyrrolidin-3-yl)-4-amino-N-(5-fluorobenzo[d]oxazol-2-yl)-1H-pyrazolo[3,4-d]pyrimidine-3-carboxamide,
(84) 1-(1-acryloylpyrrolidin-3-yl)-4-amino-N-(5-chlorobenzo[d]oxazol-2-yl)-1H-pyrazolo[3,4-d]pyrimidine-3-carboxamide,
(85) 1-(3-acrylamidopropyl)-4-amino-N-(benzo[d]oxazol-2-yl)-1H-pyrazolo[3,4-d]pyrimidine-3-carboxamide, and
(86) 1-(2-acrylamidoethyl)-4-amino-N-(benzo[d]oxazol-2-yl)-1H-pyrazolo[3,4-d]pyrimidine-3-carboxamide,
or a salt thereof.

10. A pharmaceutical composition, comprising:
the compound of claim 1 or a salt thereof; and
a pharmaceutical carrier.

11. The pharmaceutical composition of claim 10, wherein the pharmaceutical carrier is at least one selected from the group consisting of an excipient, a binder, a disintegrant, a lubricant, a coating agent, a solvent, a dissolution aid, a suspending agent, an isotonic agent, a pH adjusting agent, a buffering agent, an analgesic agent, an antiseptic, an antioxidant, a colorant, a flavoring agent, a savoring agent, and a stabilizer.

12. A pharmaceutical composition, comprising:
the compound of claim 2 or a salt thereof; and
a pharmaceutical carrier.

13. A pharmaceutical composition, comprising: the compound of claim 3 or a salt thereof; and a pharmaceutical carrier.

14. A pharmaceutical composition, comprising: the compound of claim 4 or a salt thereof; and a pharmaceutical carrier.

15. A pharmaceutical composition, comprising: the compound of claim 5 or a salt thereof; and a pharmaceutical carrier.

16. A pharmaceutical composition, comprising: the compound of claim 6 or a salt thereof; and a pharmaceutical carrier.

17. A pharmaceutical composition, comprising: the compound of claim 7 or a salt thereof; and a pharmaceutical carrier.

18. A pharmaceutical composition, comprising: the compound of claim 8 or a salt thereof; and a pharmaceutical carrier.

19. A pharmaceutical composition, comprising: the compound of claim 9 or a salt thereof; and a pharmaceutical carrier.

20. The pharmaceutical composition of claim 19, wherein the pharmaceutical carrier is at least one selected from the group consisting of an excipient, a binder, a disintegrant, a lubricant, a coating agent, a solvent, a dissolution aid, a suspending agent, an isotonic agent, a pH adjusting agent, a buffering agent, an analgesic agent, an antiseptic, an anti-oxidant, a colorant, a flavoring agent, a savoring agent, and a stabilizer.

21. A method for inhibiting BTK, comprising: administering the compound of claim 1 or a salt thereof to a subject in need thereof.

22. A method for treating a tumor, comprising: administering the compound of claim 1 or a salt thereof to a subject in need thereof.

23. A method for treating a tumor, comprising: administering the pharmaceutical composition of claim 10 to a subject in need thereof.

24. A probe, comprising:
the compound of claim 1 or a salt thereof;
a detectable label ot affinity tag; and
a linker,
wherein the linker links the compound with the detectable label or the affinity tag.

* * * * *